United States Patent
Potter et al.

(10) Patent No.: US 10,526,583 B2
(45) Date of Patent: Jan. 7, 2020

(54) COMPOSITIONS AND METHODS FOR PURIFYING RECOMBINANT ADENO-ASSOCIATED VIRUS

(71) Applicant: University of Florida Research Foundation, Inc., Gainesville, FL (US)

(72) Inventors: Mark R. Potter, Gainesville, FL (US); Barry John Byrne, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/322,809

(22) PCT Filed: Jul. 2, 2015

(86) PCT No.: PCT/US2015/039005
§ 371 (c)(1),
(2) Date: Dec. 29, 2016

(87) PCT Pub. No.: WO2016/004319
PCT Pub. Date: Jan. 7, 2016

(65) Prior Publication Data
US 2017/0130208 A1    May 11, 2017

Related U.S. Application Data

(60) Provisional application No. 62/020,315, filed on Jul. 2, 2014.

(51) Int. Cl.
| | | |
|---|---|---|
| C12N 7/02 | (2006.01) |
| A61K 35/76 | (2015.01) |
| A61K 48/00 | (2006.01) |
| C12N 15/864 | (2006.01) |
| C12N 7/00 | (2006.01) |

(52) U.S. Cl.
CPC ............... *C12N 7/00* (2013.01); *A61K 35/76* (2013.01); *C12N 2750/14132* (2013.01); *C12N 2750/14143* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 2002/0127582 A1* | 9/2002 | Atkinson | A61K 48/0091 435/6.11 |
| 2003/0134404 A1 | 7/2003 | Lochrie et al. | |
| 2011/0076744 A1 | 3/2011 | Wright et al. | |
| 2012/0135515 A1 | 5/2012 | Qu et al. | |

\* cited by examiner

*Primary Examiner* — Maria Marvich
(74) *Attorney, Agent, or Firm* — Wolf, Greenfield & Sacks, P.C.

(57) ABSTRACT

Provided herein are compositions and methods related to purification of recombinant adeno-associated virus (rAAV) particles.

15 Claims, 14 Drawing Sheets
Specification includes a Sequence Listing.

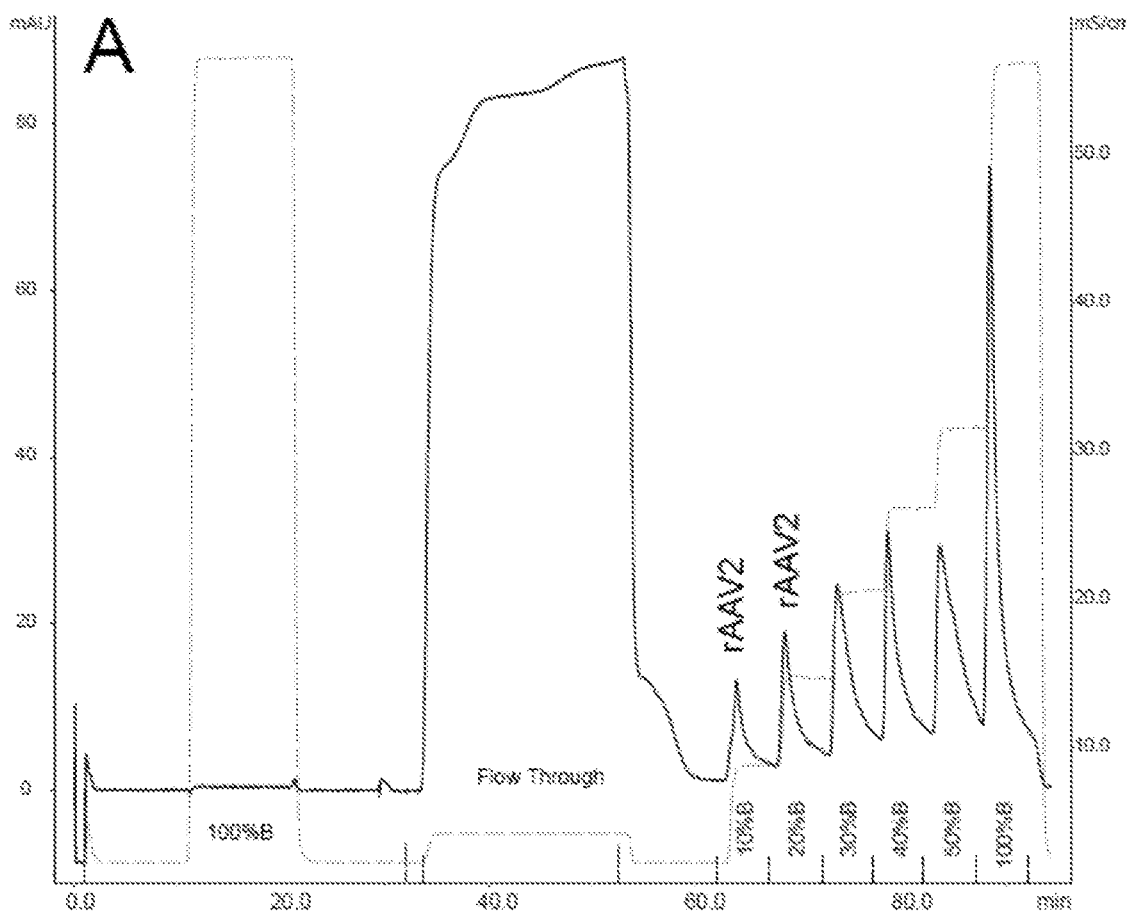
FIG. 4A
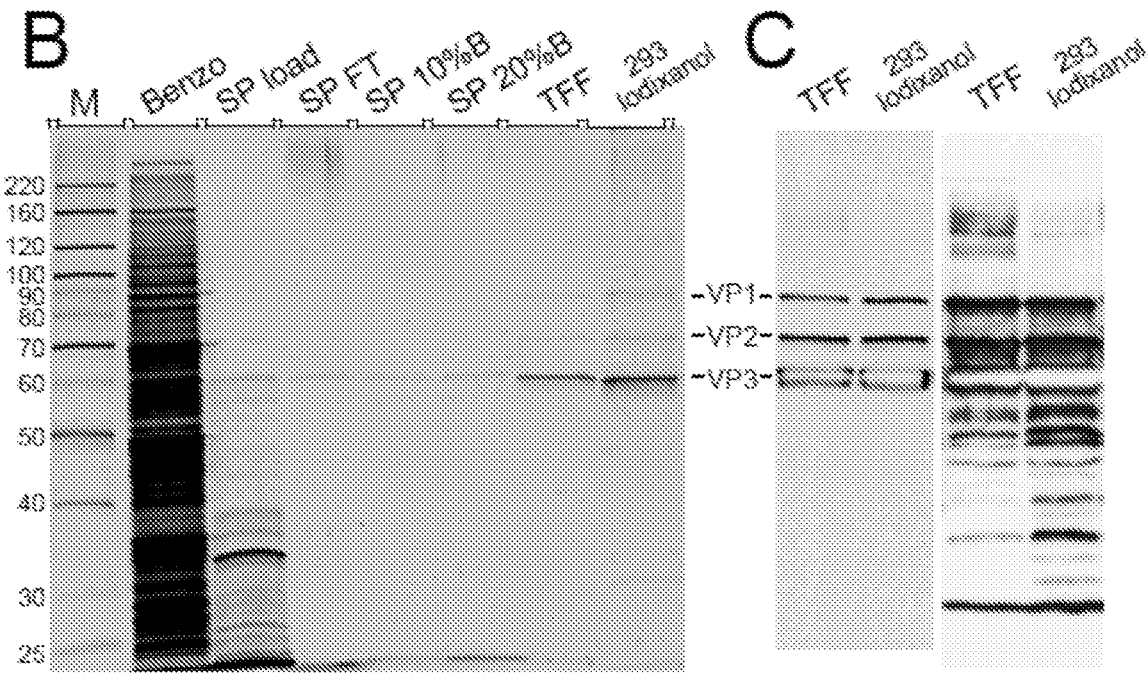
FIG. 4B
FIG. 4C

SEQUENCE LISTING

<160> NUMBER OF SEQ ID NOS: 3

<210> SEQ ID NO 1
<211> LENGTH: 7200
<212> TYPE: DNA
<213> ORGANISM: Artificial Sequence
<220> FEATURE:
<223> OTHER INFORMATION: Synthetic Polynucleotide

<400> SEQUENCE: 1

```
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtac     180
cctagttatt aatagtaatc aattacgggg tcattagttc atagcccata tatggagttc     240
cgcgttacat aacttacggt aaatggcccg cctggctgac cgcccaacga cccccgccca     300
ttgacgtcaa taatgacgta tgttcccata gtaacgccaa tagggacttt ccattgacgt     360
caatgggtgg actatttacg gtaaactgcc cacttggcag tacatcaagt gtatcatatg     420
ccaagtacgc cccctattga cgtcaatgac ggtaaatggc ccgcctggca ttatgcccag     480
tacatgacct tatgggactt tcctacttgg cagtacatct acgtattagt catcgctatt     540
accatggtcg aggtgagccc cacgttctgc ttcactctcc ccatctcccc ccctcccca     600 cccccaattt tgtatttatt tattttttaa ttattttgtg cagcgatggg ggcggggggg     660
gggggggggc gcgcgccagg cggggcgggg cggggcgagg ggcggggcgg ggcgaggcgg     720
agaggtgcgg cggcagccaa tcagagcggc gcgctccgaa agtttccttt tatggcgagg     780
cggcggcggc ggcggcccta taaaaagcga agcgcgcggc gggcgggagt cgctgcgacg     840
ctgccttcgc cccgtgcccc gctccgccgc cgcctcgcgc cgcccgcccc ggctctgact     900
gaccgcgtta ctcccacagg tgagcgggcg ggacggccct tctcctccgg gctgtaatta     960
gcgcttggtt taatgacggc ttgtttcttt tctgtggctg cgtgaaagcc ttgaggggct    1020
ccgggagggc cctttgtgcg ggggggagcg gctcgggggg tgcgtgcgtg tgtgtgtgcg    1080
tggggagcgc cgcgtgcggc ccgcgctgcc cggcggctgt gagcgctgcg ggcgcggcgc    1140
ggggctttgt gcgctccgca gtgtgcgcga ggggagcgcg gccgggggcg gtgccccgcg    1200
gtgcgggggg ggctgcgagg ggaacaaagg ctgcgtgcgg ggtgtgtgcg tggggggtg     1260 agcagggggt gtgggcgcgg cggtcgggct gtaaccccc cctgcacccc cctccccgag    1320
ttgctgagca cggcccggct tcgggtgcgg ggctccgtac ggggcgtggc gcggggctcg    1380
ccgtgccggg cggggggtgg cggcaggtgg gggtgccggg cggggcgggg ccgcctcggg    1440
ccggggaggg ctcgggggag gggcgcggcg gccccggag cgccggcggc tgtcgaggcg     1500
cggcgagccg cagccattgc cttttatggt aatcgtgcga gagggcgcag ggacttcctt    1560
tgtcccaaat ctgtgcggag ccgaaatctg ggaggcgccg ccgcacccc tctagcgggc    1620
```

```
gcggggcgaa gcggtgcggc gccggcagga aggaaatggg cggggagggc cttcgtgcgt    1680
cgccgcgccg ccgtcccctt ctccctctcc agcctcgggg ctgtccgcgg ggggacggct    1740
gccttcgggg gggacggggc agggcggggt tcggcttctg gcgtgtgacc ggcggctcta    1800
gagcctctgc taaccatgtt catgccttct tcttttccct acagctcctg ggcaacgtgc    1860
tggttattgt gctgtctcat cattttggca aagaattcct cgaagatcta ggcctgcagg    1920
cggccgccgc caccatgagc aagggcgagg aactgttcac tggcgtggtc ccaattctcg    1980
tggaactgga tggcgatgtg aatgggcaca aattttctgt cagcggagag ggtgaaggtg    2040
atgccacata cggaaagctc accctgaaat tcatctgcac cactggaaag ctccctgtgc    2100
catggccaac actggtcact accctgacct atggcgtgca gtgcttttcc agatacccag    2160
accatatgaa gcagcatgac ttttttcaaga gcgccatgcc cgagggctat gtgcaggaga    2220
gaaccatctt tttcaaagat gacgggaact acaagacccg cgctgaagtc aagttcgaag    2280
gtgacaccct ggtgaataga atcgagctga agggcattga ctttaaggag gatggaaaca    2340
ttctcggcca caagctggaa tacaactata actcccacaa tgtgtacatc atggccgaca    2400
agcaaaagaa tggcatcaag gtcaacttca gatcagaca  caacattgag gatggatccg    2460
tgcagctggc cgaccattat caacagaaca ctccaatcgg cgacggccct gtgctcctcc    2520
cagacaacca ttacctgtcc acccagtctg ccctgtctaa agatcccaac gaaaagagag    2580
accacatggt cctgctggag tttgtgaccg ctgctgggat cacacatggc atggacgagc    2640
tgtacaagtg agcggccgcg gggatccaga catgataaga tacattgatg agtttggaca    2700
aaccacaact agaatgcagt gaaaaaaatg ctttatttgt gaaatttgtg atgctattgc    2760
tttatttgta accattataa gctgcaataa acaagttaac aacaacaatt gcattcattt    2820
tatgtttcag gttcaggggg aggtgtggga ggttttttag tcgacctcga gcagtgtggt    2880
tttgcaagag gaagcaaaaa gcctctccac ccaggcctgg aatgtttcca cccaagtcga    2940
aggcagtgtg gttttgcaag aggaagcaaa aagcctctcc acccaggcct ggaatgtttc    3000
cacccaatgt cgagcaaccc cgcccagcgt cttgtcattg gcgaattcga acacgcagat    3060
gcagtcgggg cggcgcggtc ccaggtccac ttcgcatatt aaggtgacgc gtgtggcctc    3120
gaacaccgag cgaccctgca gccaatatgg gatcggccat tgaacaagat ggattgcacg    3180
caggttctcc ggccgcttgg gtggagaggc tattcggcta tgactgggca acagacaa     3240
tcggctgctc tgatgccgcc gtgttccggc tgtcagcgca ggggcgcccg gttcttttg     3300
tcaagaccga cctgtccggt gccctgaatg aactgcagga cgaggcagcg cggctatcgt    3360
ggctggccac gacgggcgtt ccttgcgcag ctgtgctcga cgttgtcact gaagcgggaa    3420
gggactggct gctattgggc gaagtgccgg ggcaggatct cctgtcatct caccttgctc    3480
ctgccgagaa agtatccatc atggctgatg caatgcggcg gctgcatacg cttgatccgg    3540
ctacctgccc attcgaccac caagcgaaac atcgcatcga gcgagcacgt actcggatgg    3600
aagccggtct tgtcgatcag gatgatctgg acgaagagca tcaggggctc gcgccagccg    3660
aactgttcgc caggctcaag gcgcgcatgc ccgacggcga ggatctcgtc gtgacccatg    3720
gcgatgcctg cttgccgaat atcatggtgg aaaatggccg cttttctgga ttcatcgact    3780
gtggccggct gggtgtggcg gaccgctatc aggacatagc gttggctacc cgtgatattg    3840
ctgaagagct tggcggcgaa tgggctgacc gcttcctcgt gctttacggt atcgccgctc    3900
ccgattcgca gcgcatcgcc ttctatcgcc ttcttgacga gttcttctga ggggatccgt    3960
cgactagagc tcgctgatca gcctcgactg tgccttctag ttgccagcca tctgttgttt    4020
```

```
gcccctcccc cgtgccttcc ttgaccctgg aaggtgccac tcccactgtc ctttcctaat    4080
aaaatgagga aattgcatcg cattgtctga gtaggtgtca ttctattctg gggggtgggg    4140
tggggcagga cagcaagggg gaggattggg aagacaatag caggcatgct ggggagagat    4200
ctaggaaccc ctagtgatgg agttggccac tccctctctg cgcgctcgct cgctcactga    4260
ggccgcccgg gcaaagcccg ggcgtcgggc gacctttggt cgcccggcct cagtgagcga    4320
gcgagcgcgc agagagggag tggccaaccc cccccccccc cccctgcag ccctgcatta    4380
atgaatcggc caacgcgcgg ggagaggcgg tttgcgtatt gggcgctctt ccgcttcctc    4440
gctcactgac tcgctgcgct cggtcgttcg gctgcggcga gcggtatcag ctcactcaaa    4500
ggcggtaata cggttatcca cagaatcagg ggataacgca ggaaagaaca tgtgagcaaa    4560
aggccagcaa aaggccagga accgtaaaaa ggccgcgttg ctggcgtttt tccataggct    4620
ccgcccccct gacgagcatc acaaaaatcg acgctcaagt cagaggtggc gaaacccgac    4680
aggactataa agataccagg cgtttccccc tggaagctcc ctcgtgcgct ctcctgttcc    4740
gaccctgccg cttaccggat acctgtccgc ctttctccct tcgggaagcg tggcgctttc    4800
tcaatgctca cgctgtaggt atctcagttc ggtgtaggtc gttcgctcca agctgggctg    4860
tgtgcacgaa ccccccgttc agcccgaccg ctgcgcctta tccggtaact atcgtcttga    4920
gtccaacccg gtaagacacg acttatcgcc actggcagca gccactggta acaggattag    4980
cagagcgagg tatgtaggcg gtgctacaga gttcttgaag tggtggccta actacggcta    5040
cactagaagg acagtatttg gtatctgcgc tctgctgaag ccagttacct tcggaaaaag    5100
agttggtagc tcttgatccg gcaaacaaac caccgctggt agcggtggtt tttttgtttg    5160
caagcagcag attacgcgca gaaaaaaagg atcctttga tctttctac    5220
ggggtctgac gctcagtgga acgaaaactc acgttaaggg attttggtca tgagattatc    5280
aaaaaggatc ttcacctaga tccttttaaa ttaaaaatga gttttaaat caatctaaag    5340
tatatatgag taaacttggt ctgacagtta ccaatgctta atcagtgagg cacctatctc    5400
agcgatctgt ctatttcgtt catccatagt tgcctgactc cccgtcgtgt agataactac    5460
gatacgggag ggcttaccat ctggccccag tgctgcaatg ataccgcgag acccacgctc    5520
accggctcca gatttatcag caataaacca gccagccgga agggccgagc gcagaagtgg    5580
tcctgcaact ttatccgcct ccatccagtc tattaattgt tgccgggaag ctagagtaag    5640
tagttcgcca gttaatagtt tgcgcaacgt tgttgccatt gctacaggca tcgtggtgtc    5700
acgctcgtcg tttggtatgg cttcattcag ctccggttcc caacgatcaa ggcgagttac    5760
atgatccccc atgttgtgca aaaaagcggt tagctccttc ggtcctccga tcgttgtcag    5820
aagtaagttg gccgcagtgt tatcactcat ggttatggca gcactgcata attctcttac    5880
tgtcatgcca tccgtaagat gcttttctgt gactggtgag tactcaacca agtcattctg    5940
agaatagtgt atgcggcgac cgagttgctc ttgcccggcg tcaatacggg ataataccgc    6000
gccacatagc agaactttaa aagtgctcat cattggaaaa cgttcttcgg ggcgaaaact    6060
ctcaaggatc ttaccgctgt tgagatccag ttcgatgtaa cccactcgtg cacccaactg    6120
atcttcagca tcttttactt tcaccagcgt ttctgggtgc gcaaaacag gaaggcaaaa    6180
tgccgcaaaa aagggaataa gggcgacacg gaaatgttga atactcatac tcttcctttt    6240
tcaatattat tgaagcattt atcagggtta ttgtctcatg agcggataca tatttgaatg    6300
tatttagaaa aataaacaaa tagggggttcc gcgcacattt ccccgaaaag tgccacctga    6360
```

| | |
|---|---|
| cgtctaagaa accattatta tcatgacatt aacctataaa aataggcgta tcacgaggcc | 6420 |
| ctttcgtctc gcgcgtttcg gtgatgacgg tgaaaacctc tgacacatgc agctcccgga | 6480 |
| gacggtcaca gcttgtctgt aagcggatgc cgggagcaga caagcccgtc agggcgcgtc | 6540 |
| agcgggtgtt ggcgggtgtc ggggctggct taactatgcg gcatcagagc agattgtact | 6600 |
| gagagtgcac catatgcggt gtgaaatacc gcacagatgc gtaaggagaa ataccgcat | 6660 |
| caggaaattg taaacgttaa tattttgtta aaattcgcgt taaattttg ttaaatcagc | 6720 |
| tcatttttta accaataggc cgaaatcggc aaaatccctt ataaatcaaa agaatagacc | 6780 |
| gagatagggt tgagtgttgt tccagtttgg aacaagagtc cactattaaa gaacgtggac | 6840 |
| tccaacgtca agggcgaaa aaccgtctat cagggcgatg gcccactacg tgaaccatca | 6900 |
| ccctaatcaa ttttttggg gtcgaggtgc cgtaaagcac taaatcggaa ccctaaaggg | 6960 |
| agcccccgat ttagagcttg acggggaaag ccggcgaacg tggcgagaaa ggaagggaag | 7020 |
| aaagcgaaag gagcgggcgc tagggcgctg gcaagtgtag cggtcacgct gcgcgtaacc | 7080 |
| accacacccg ccgcgcttaa tgcgccgcta cagggcgcgt cgcgccattc gccattcagg | 7140 |
| ctacgcaact gttgggaagg gcgatcggtg cgggcctctt cgctattacg ccaggctgca | 7200 |

<210> SEQ ID NO 2
<211> LENGTH: 18664
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---|
| cgggccccc ctcgaggtcg acagaagcac catgtccttg ggtccggcct gctgaatgcg | 60 |
| caggcggtcg gccatgcccc aggcttcgtt ttgacatcgg cgcaggtctt tgtagtagtc | 120 |
| ttgcatgagc ctttctaccg gcacttcttc ttctccttcc tcttgtcctg catctcttgc | 180 |
| atctatcgct gcggcggcgg cggagtttgg ccgtaggtgg cgccctcttc ctcccatgcg | 240 |
| tgtgaccccg aagcccctca tcggctgaag cagggctagg tcggcgacaa cgcgctcggc | 300 |
| taatatggcc tgctgcacct gcgtgagggt agactggaag tcatccatgt ccacaaagcg | 360 |
| gtggtatgcg cccgtgttga tggtgtaagt gcagttggcc ataacggacc agttaacggt | 420 |
| ctggtgaccc ggctgcgaga gctcggtgta cctgagacgc gagtaagccc tcgagtcaaa | 480 |
| tacgtagtcg ttgcaagtcc gcaccaggta ctggtatccc accaaaaagt gcggcggcgg | 540 |
| ctggcggtag aggggccagc gtagggtggc cgggctccg ggggcgagat cttccaacat | 600 |
| aaggcgatga tatccgtaga tgtacctgga catccaggtg atgccggcgg cggtggtgga | 660 |
| ggcgcgcgga aagtcgcgga cgcggttcca gatgttgcgc agcggcaaaa agtgctccat | 720 |
| ggtcgggacg ctctggccgg tcaggcgcgc gcaatcgttg acgctctacc gtgcaaaagg | 780 |
| agagcctgta agcgggcact cttccgtggt ctggtggata aattcgcaag ggtatcatgg | 840 |
| cggacgaccg gggttcgagc cccgtatccg gccgtccgcc gtgatccatg cggttaccgc | 900 |
| ccgcgtgtcg aacccaggtg tgcgacgtca gacaacgggg gagtgctcct tttggcttcc | 960 |
| ttccaggcgc ggcggctgct gcgctagctt ttttggccac tggccgcgcg cagcgtaagc | 1020 |
| ggttaggctg gaaagcgaaa gcattaagtg gctcgctccc tgtagccgga gggttatttt | 1080 |
| ccaagggttg agtcgcggga ccccggttc gagtctcgga ccggccggac tgcggcgaac | 1140 |
| gggggtttgc ctccccgtca tgcaagaccc cgcttgcaaa ttcctccgga aacagggacg | 1200 |
| agccccttt ttgcttttcc cagatgcatc cggtgctgcg gcagatgcgc cccctcctc | 1260 |

```
agcagcggca agagcaagag cagcggcaga catgcagggc accctcccct cctcctaccg    1320
cgtcaggagg ggcgacatcc gcggttgacg cggcagcaga tggtgattac gaaccccgc     1380 ggcgccgggc ccggcactac ctggacttgg aggagggcga gggcctggcg cggctaggag    1440
cgccctctcc tgagcggtac ccaagggtgc agctgaagcg tgatacgcgt gaggcgtacg    1500
tgccgcggca gaacctgttt cgcgaccgcg agggagagga gcccgaggag atgcgggatc    1560
gaaagttcca cgcagggcgc gagctgcggc atggcctgaa tcgcgagcgg ttgctgcgcg    1620
aggaggactt tgagcccgac gcgcgaaccg ggattagtcc cgcgcgcgca cacgtggcgg    1680
ccgccgacct ggtaaccgca tacgagcaga cggtgaacca ggagattaac tttcaaaaaa    1740
gctttaacaa ccacgtgcgt acgcttgtgg cgcgcgagga ggtggctata ggactgatgc    1800
atctgtggga ctttgtaagc gcgctggagc aaaacccaaa tagcaagccg ctcatggcgc    1860
agctgttcct tatagtgcag cacagcaggg acaacgaggc attcagggat gcgctgctaa    1920
acatagtaga gcccgagggc cgctggctgc tcgatttgat aaacatcctg cagagcatag    1980
tggtgcagga gcgcagcttg agcctggctg acaaggtggc cgccatcaac tattccatgc    2040
ttagcctggg caagttttac gcccgcaaga tataccatac cccttacgtt cccatagaca    2100
aggaggtaaa gatcgagggg ttctacatgc gcatggcgct gaaggtgctt accttgagcg    2160
acgacctggg cgtttatcgc aacgagcgca tccacaaggc cgtgagcgtg agccggcggc    2220
gcgagctcag cgaccgcgag ctgatgcaca gcctgcaaag ggccctggct ggcacgggca    2280
gcggcgatag agaggccgag tcctactttg acgcgggcgc tgacctgcgc tgggccccaa    2340
gccgacgcgc cctggaggca gctggggccg gacctgggct ggcggtggca cccgcgcgcg    2400
ctggcaacgt cggcggcgtg gaggaatatg acgaggacga tgagtacgag ccagaggacg    2460
gcgagtacta agcggtgatg tttctgatca gatgatgcaa gacgcaacgg acccggcggt    2520
gcgggcggcg ctgcagagcc agccgtccgg ccttaactcc acggacgact ggcgccaggt    2580
catggaccgc atcatgtcgc tgactgcgcg caatcctgac gcgttccggc agcagccgca    2640
ggccaaccgg ctctccgcaa ttctggaagc ggtggtcccg gcgcgcgcaa accccacgca    2700
cgagaaggtg ctggcgatcg taaacgcgct ggccgaaaac agggccatcc ggcccgacga    2760
ggccggcctg gtctacgacg cgctgcttca gcgcgtggct cgttacaaca gcggcaacgt    2820
gcagaccaac ctgaccggc tggtggggga tgtgcgcgag gccgtggcgc agcgtgagcg    2880
cgcgcagcag cagggcaacc tgggctccat ggttgcacta aacgccttcc tgagtacaca    2940
gcccgccaac gtgccgcggg gacaggagga ctacaccaac tttgtgagcg cactgcggct    3000
aatggtgact gagacaccgc aaagtgaggt gtaccagtct gggccagact attttttcca    3060
gaccagtaga caaggcctgc agaccgtaaa cctgagccag gctttcaaaa acttgcaggg    3120
gctgtggggg gtgcgggctc ccacaggcga ccgcgcgacc gtgtctagct tgctgacgcc    3180
caactcgcgc ctgttgctgc tgctaatagc cccttcacg gacagtggca gcgtgtcccg    3240
ggacacatac ctaggtcact tgctgacact gtaccgcgag gccataggtc aggcgcatgt    3300
ggacgagcat actttccagg agattacaag tgtcagccgc gcgctggggc aggaggacac    3360
gggcagcctg gaggcaaccc taaactacct gctgaccaac cggcggcaga agatcccctc    3420
gttgcacagt ttcgcaccct ttggcgcatc ccattctcca gtaactttat gtccatgggc    3480
gcactcacag acctgggcca aaaccttctc tacgccaact ccgcccacgc gctagacatg    3540
acttttgagg tggatcccat ggacgagccc acccttcttt atgttttgtt tgaagtcttt    3600
```

```
gacgtggtcc gtgtgcaccg gccgcaccgc ggcgtcatcg aaaccgtgta cctgcgcacg    3660
cccttctcgg ccggcaacgc cacaacataa agaagcaagc aacatcaaca acagctgccg    3720
ccatgggctc cagtgagcag gaactgaaag ccattgtcaa agatcttggt tgtgggccat    3780 atttttggg cacctatgac aagcgctttc caggctttgt ttctccacac aagctcgcct    3840
gcgccatagt caatacggcc ggtcgcgaga ctggggcgt acactggatg gccttgcct     3900 ggaacccgca ctcaaaaaca tgctacctct ttgagccctt tggcttttct gaccagcgac    3960
tcaagcaggt ttaccagttt gagtacgagt cactcctgcg ccgtagcgcc attgcttctt    4020
cccccgaccg ctgtataacg ctggaaaagt ccacccaaag cgtacagggg cccaactcgg    4080
ccgcctgtgg actattctgc tgcatgtttc tccacgcctt tgccaactgg ccccaaactc    4140
ccatggatca caaccccacc atgaaccta ttaccggggt acccaactcc atgctcaaca     4200
gtccccaggt acagcccacc ctgcgtcgca accaggaaca gctctacagc ttcctggagc    4260
gccactcgcc ctacttccgc agccacagtg cgcagattag gagcgccact tctttttgtc    4320
acttgaaaaa catgtaaaaa taatgtacta gagacacttt caataaaggc aaatgctttt    4380
atttgtacac tctcgggtga ttatttaccc ccacccttgc cgtctgcgcc gtttaaaaat    4440 caaagggggtt ctgccgcgca tcgctatgcg ccactggcag ggacacgttg cgatactggt    4500
gtttagtgct ccacttaaac tcaggcacaa ccatccgcgg cagctcggtg aagttttcac    4560
tccacaggct gcgcaccatc accaacgcgt ttagcaggtc gggcgccgat atcttgaagt    4620
cgcagttggg gcctccgccc tgcgcgcgcg agttgcgata cacagggttg cagcactgga    4680
acactatcag cgccgggtgg tgcacgctgg ccagcacgct cttgtcggag atcagatccg    4740
cgtccaggtc ctccgcgttg ctcagggcga acggagtcaa cttggtagc tgccttccca    4800 aaagggcgc gtgcccaggc tttgagttgc actcgcaccg tagtggcatc aaaggtgac    4860 cgtgccggt ctgggcgtta ggatacagcg cctgcataaa agccttgatc tgcttaaaag     4920
ccacctgagc ctttgcgcct tcagagaaga acatgccgca agacttgccg gaaaactgat    4980
tggccggaca ggccgcgtcg tgcacgcagc accttgcgtc ggtgttggag atctgcacca    5040
catttcggcc ccaccggttc ttcacgatct tggccttgct agactgctcc ttcagcgcgc    5100
gctgcccgtt ttcgctcgtc acatccattt caatcacgtg ctccttattt atcataatgc    5160
ttccgtgtag acacttaagc tcgccttcga tctcagcgca gcggtgcagc cacaacgcgc    5220
agcccgtggg ctcgtgatgc ttgtaggtca cctctgcaaa cgactgcagg tacgcctgca    5280
ggaatcgccc catcatcgtc acaaaggtct tgttgctggt gaaggtcagc tgcaacccgc    5340
ggtgctcctc gttcagccag gtcttgcata cggccgccag agcttccact tggtcaggca    5400
gtagtttgaa gttcgccttt agatcgttat ccacgtggta cttgtccatc agcgcgcgcg    5460
cagcctccat gcccttctcc cacgcagaca cgatcggcac actcagcggg ttcatcaccg    5520
taatttcact ttccgcttcg ctgggctctt cctcttcctc ttgcgtccgc ataccacgcg    5580
ccactgggtc gtcttcattc agccgccgca ctgtgcgctt acctcctttg ccatgcttga    5640
ttagcaccgg tgggttgctg aaacccacca tttgtagcgc cacatcttct ctttcttcct    5700
cgctgtccac gattacctct ggtgatgcg ggcgctcggg cttgggagaa gggcgcttct    5760
ttttcttctt gggcgcaatg gccaaatccg ccgccgaggt cgatggccgc gggctgggtg    5820
tgcgcggcac cagcgcgtct tgtgatgagt cttcctcgtc ctcggactcg atacgccgcc    5880
tcatccgctt ttttgggggc gcccggggag gcggcggcga cggggacggg gacgacacgt    5940
cctccatggt tggggacgt cgcgccgcac cgcgtccgcg ctcgggggtg gtttcgcgct    6000
```

```
gctcctcttc ccgactggcc atttccttct cctataggca gaaaaagatc atggagtcag      6060
tcgagaagaa ggacagccta accgccccct ctgagttcgc caccaccgcc tccaccgatg      6120
ccgccaacgc gcctaccacc ttccccgtcg aggcaccccc gcttgaggag gaggaagtga      6180
ttatcgagca ggacccaggt tttgtaagcg aagacgacga ggaccgctca gtaccaacag      6240
aggataaaaa gcaagaccag gacaacgcag aggcaaacga ggaacaagtc gggcggggg       6300 acgaaaggca tggcgactac ctagatgtgg gagacgacgt gctgttgaag catctgcagc      6360
gccagtgcgc cattatctgc gacgcgttgc aagagcgcag cgatgtgccc ctcgccatag      6420
cggatgtcag ccttgcctac gaacgccacc tattctcacc gcgcgtaccc cccaaacgcc      6480
aagaaaacgg cacatgcgag cccaacccgc gcctcaactt ctaccccgta tttgccgtgc      6540
cagaggtgct tgccacctat cacatctttt tccaaaactg caagataccc ctatcctgcc      6600
gtgccaaccg cagccgagcg gacaagcagc tggccttgcg gcagggcgct gtcatacctg      6660
atatcgcctc gctcaacgaa gtgccaaaaa tctttgaggg tcttggacgc gacgagaagc      6720
gcgcggcaaa cgctctgcaa caggaaaaca gcgaaaatga aagtcactct ggagtgttgg      6780
tggaactcga gggtgacaac gcgcgcctag ccgtactaaa acgcagcatc gaggtcaccc      6840
actttgccta cccggcactt aacctacccc ccaaggtcat gagcacagtc atgagtgagc      6900
tgatcgtgcg ccgtgcgcag cccctggaga gggatgcaaa tttgcaagaa caaacagagg      6960
agggcctacc cgcagttggc gacgagcagc tagcgcgctg gcttcaaacg cgcgagcctg      7020
ccgacttgga ggagcgacgc aaactaatga tggccgcagt gctcgttacc gtggagcttg      7080
agtgcatgca gcggttcttt gctgacccgg agatgcagcg caagctagag gaaacattgc      7140
actacacctt tcgacagggc tacgtacgcc aggcctgcaa gatctccaac gtggagctct      7200
gcaacctggt ctcctacctt ggaattttgc acgaaaaccg ccttgggcaa aacgtgcttc      7260
attccacgct caagggcgag gcgcgccgcg actacgtccg cgactgcgtt tacttatttc      7320
tatgctacac ctggcagacg gccatgggcg tttggcagca gtgcttggag gagtgcaacc      7380
tcaaggagct gcagaaactg ctaaagcaaa acttgaagga cctatggacg gccttcaacg      7440
agcgctccgt ggccgcgcac ctggcggaca tcatttttcc cgaacgcctg cttaaaaccc      7500
tgcaacaggg tctgccagac ttcaccagtc aaagcatgtt gcagaacttt aggaacttta      7560
tcctagagcg ctcaggaatc ttgcccgcca cctgctgtgc acttcctagc gactttgtgc      7620
ccattaagta ccgcgaatgc cctccgccgc tttggggcca ctgctacctt ctgcagctag      7680
ccaactacct tgcctaccac tctgacataa tggaagacgt gagcggtgac ggtctactgg      7740
agtgtcactg tcgctgcaac ctatgcaccc cgcaccgctc cctggtttgc aattcgcagc      7800
tgcttaacga aagtcaaatt atcggtacct ttgagctgca gggtccctcg cctgacgaaa      7860
agtccgcggc tccggggttg aaactcactc cggggctgtg gacgtcggct taccttcgca      7920
aatttgtacc tgaggactac cacgcccacg agattaggtt ctacgaagac caatcccgcc      7980
cgccaaatgc ggagcttacc gcctgcgtca ttacccaggg ccacattctt ggccaattgc      8040
aagccatcaa caaagcccgc caagagtttc tgctacgaaa gggacggggg gtttacttgg      8100 accccagtc cggcgaggag ctcaacccaa tcccccgcc gccgcagccc tatcagcagc      8160
agccgcgggc ccttgcttcc caggatggca cccaaaaaga agctgcagct gccgccgcca      8220 cccacgacg aggaggaata ctgggacagt caggcagagg aggttttgga cgaggaggag      8280
gaggacatga tggaagactg ggagagccta gacgaggaag cttccgaggt cgaagaggtg      8340
```

```
tcagacgaaa caccgtcacc ctcggtcgca ttccccctcgc cggcgcccca gaaatcggca    8400
accggttcca gcatggctac aacctccgct cctcaggcgc cgccggcact gcccgttcgc    8460
cgacccaacc gtagatggga caccactgga accagggccg gtaagtccaa gcagccgccg    8520
ccgttagccc aagagcaaca acagcgccaa ggctaccgct catggcgcgg gcacaagaac    8580
gccatagttg cttgcttgca agactgtggg ggcaacatct ccttcgcccg ccgctttctt    8640
ctctaccatc acggcgtggc cttcccccgt aacatcctgc attactaccg tcatctctac    8700
agcccatact gcaccggcgg cagcggcagc ggcagcaaca gcagcggcca cacagaagca    8760
aaggcgaccg gatagcaaga ctctgacaaa gcccaagaaa tccacagcgg cggcagcagc    8820
aggaggagga gcgctgcgtc tggcgcccaa cgaacccgta tcgacccgcg agcttagaaa    8880
caggattttt cccactctgt atgctatatt tcaacagagc aggggccaag aacaagagct    8940
gaaaataaaa aacaggtctc tgcgatccct caccccgcagc tgcctgtatc acaaaagcga    9000
agatcagctt cggcgcacgc tggaagacgc ggaggctctc ttcagtaaat actgcgcgct    9060
gactcttaag gactagtttc gcgcccttttc tcaaatttaa gcgcgaaaac tacgtcatct    9120
ccagcggcca caccccggcgc cagcacctgt cgtcagcgcc attatgagca aggaaattcc    9180
cacgccctac atgtggagtt accagccaca aatgggactt gcggctggag ctgcccaaga    9240
ctactcaacc cgaataaact acatgagcgc gggaccccac atgatatccc gggtcaacgg    9300
aatccgcgcc caccgaaacc gaattctctt ggaacaggcg gctattacca ccacacctcg    9360
taataacctt aatccccgta gttggcccgc tgccctggtg taccaggaaa gtcccgctcc    9420
caccactgtg gtacttccca gagacgccca ggccgaagtt cagatgacta actcaggggc    9480
gcagcttgcg ggcggctttc gtcacagggt gcggtcgccc gggcagggta taactcacct    9540
gacaatcaga gggcgaggta ttcagctcaa cgacagagtcg gtgagctcct cgcttggtct    9600
ccgtccggac gggacatttc agatcggcgg cgccggccgt ccttcattca cgcctcgtca    9660
ggcaatccta actctgcaga cctcgtcctc tgagccgcgc tctggaggca ttggaactct    9720
gcaatttatt gaggagtttg tgccatcggt ctactttaac cccttctcgg gacctcccgg    9780
ccactatccg gatcaattta ttcctaactt tgacgcggta aaggactcgg cggacggcta    9840
cgactgaatg ttaagtggag aggcagagca actgcgcctg aaacacctgg tccactgtcg    9900
ccgccacaag tgctttgccc gcgactccgg tgagttttgc tactttgaat tgcccgagga    9960
tcatatcgag ggcccggcgc acggcgtccg gcttaccgcc cagggagagc ttgcccgtag    10020
cctgattcgg gagtttaccc agcgcccccct gctagttgag cgggacaggg gaccctgtgt    10080
tctcactgtg atttgcaact gtcctaacct tggattacat caagatcctc tagttaatta    10140
actagagtac ccggggatct tattcccttt aactaataaa aaaaataat aaagcatcac    10200 ttacttaaaa tcagttagca aatttctgtc cagtttattc agcagcacct ccttgccctc    10260
ctcccagctc tggtattgca gcttcctcct ggctgcaaac tttctccaca atctaaatgg    10320
aatgtcagtt tcctcctgtt cctgtccatc cgcacccact atcttcatgt tgttgcagat    10380
gaagcgcgca agaccgtctg aagataccttt caaccccgtg tatccatatg acacggaaac    10440
cggtcctcca actgtgcctt ttcttactcc tccctttgta tccccaatg gtttcaaga    10500 gagtcccct ggggtactct ctttgcgcct atccgaacct ctagttacct ccaatggcat    10560
gcttgcgctc aaaatgggca acggcctctc tctggacgag gccggcaacc ttacctccca    10620
aaatgtaacc actgtgagcc cacctctcaa aaaaccaag tcaaacataa acctggaaat    10680
atctgcaccc ctcacagtta cctcagaagc cctaactgtg gctgccgccg cacctctaat    10740
```

```
ggtcgcgggc aacacactca ccatgcaatc acaggccccg ctaaccgtgc acgactccaa    10800
acttagcatt gccacccaag gacccctcac agtgtcagaa ggaaagctag ccctgcaaac    10860
atcaggcccc ctcaccacca ccgatagcag taccctta ct atcactgcct cacccc ctct    10920 aactactgcc actggtagct tgggcattga cttgaaagag cccatttata cacaaaatgg    10980
aaaactagga ctaaagtacg gggctccttt gcatgtaaca gacgacctaa acactttgac    11040
cgtagcaact ggtccaggtg tgactattaa taatacttcc ttgcaaacta agttactgg    11100 agccttgggt tttgattcac aaggcaatat gcaacttaat gtagcaggag gactaaggat    11160
tgattctcaa aacagacgcc ttatacttga tgttagttat ccgtttgatg ctcaaaacca    11220
actaaatcta agactaggac agggccctct ttttataaac tcagcccaca acttggatat    11280
taactacaac aaaggccttt acttgtttac agcttcaaac aattccaaaa agcttgaggt    11340
taacctaagc actgccaagg ggttgatgtt tgacgctaca gccatagcca ttaatgcagg    11400
agatgggctt gaatttggtt cacctaatgc accaaacaca aatcccctca aaacaaaaat    11460
tggccatggc ctagaatttg attcaaacaa ggctatggtt cctaaactag gaactggcct    11520
tagttttgac agcacaggtg ccattacagt aggaaacaaa aataatgata agctaacttt    11580
gtggaccaca ccagctccat ctcctaactg tagactaaat gcagagaaag atgctaaaact    11640 cactttggtc ttaacaaaat gtggcagtca aatacttgct acagtttcag ttttggctgt    11700
taaaggcagt ttggctccaa tatctggaac agttcaaagt gctcatctta ttataagatt    11760
tgacgaaaat ggagtgctac taaacaattc cttcctggac ccagaatatt ggaactttag    11820
aaatggagat cttactgaag gcacagccta tacaaacgct gttggattta tgcctaacct    11880
atcagcttat ccaaaatctc acggtaaaac tgccaaaagt aacattgtca gtcaagttta    11940
cttaaacgga gacaaaacta aacctgtaac actaaccatt acactaaacg gtacacagga    12000
aacaggagac acaactccaa gtgcatactc tatgtcattt tcatgggact ggtctggcca    12060
caactacatt aatgaaatat ttgccacatc ctcttacact ttttcataca ttgcccaaga    12120
ataaagaatc gtttgtgtta tgtttcaacg tgtttatttt tcaattgcag aaaatttcaa    12180 gtcattttc attcagtagt atagccccac caccacatag cttatacaga tcaccgtacc    12240
ttaatcaaac tcacagaacc ctagtattca acctgccacc tccctcccaa cacacagagt    12300
acacagtcct ttctccccgg ctggccttaa aaagcatcat atcatgggta acagacatat    12360
tcttaggtgt tatattccac acggtttcct gtcgagccaa acgctcatca gtgatattaa    12420
taaactcccc gggcagctca cttaagttca tgtcgctgtc cagctgctga gccacaggct    12480
gctgtccaac ttgcggttgc ttaacgggcg gcgaaggaga agtccacgcc tacatggggg    12540
tagagtcata atcgtgcatc aggataggc ggtggtgctg cagcagcgcg cgaataaact    12600
gctgccgccg ccgctccgtc ctgcaggaat acaacatggc agtggtctcc tcagcgatga    12660
ttcgcaccgc ccgcagcata aggcgccttg tcctccgggc acagcagcgc accctgatct    12720
cacttaaatc agcacagtaa ctgcagcaca gcaccacaat attgttcaaa atcccacagt    12780
gcaaggcgct gtatccaaag ctcatggcgg ggaccacaga acccacgtgg ccatcatacc    12840
acaagcgcag gtagattaag tggcgacccc tcataaacac gctggacata aacattacct    12900
cttttggcat gttgtaattc accacctccc ggtaccatat aaacctctga ttaaacatgg    12960
cgccatccac caccatccta aaccagctgg ccaaaacctg cccgccggct atacactgca    13020
gggaaccggg actggaacaa tgacagtgga gagcccagga ctcgtaacca tggatcatca    13080
```

```
tgctcgtcat gatatcaatg ttggcacaac acaggcacac gtgcatacac ttcctcagga   13140
ttacaagctc ctcccgcgtt agaaccatat cccagggaac aacccattcc tgaatcagcg   13200
taaatcccac actgcaggga agacctcgca cgtaactcac gttgtgcatt gtcaaagtgt   13260
tacattcggg cagcagcgga tgatcctcca gtatggtagc gcgggtttct gtctcaaaag   13320
gaggtagacg atccctactg tacggagtgc gccgagacaa ccgagatcgt gttggtcgta   13380
gtgtcatgcc aaatggaacg ccggacgtag tcatatttcc tgaagcaaaa ccaggtgcgg   13440
gcgtgacaaa cagatctgcg tctccggtct cgccgcttag atcgctctgt gtagtagttg   13500
tagtatatcc actctctcaa agcatccagg cgcccctgg cttcgggttc tatgtaaact    13560
ccttcatgcg ccgctgccct gataacatcc accaccgcag aataagccac acccagccaa   13620
cctacacatt cgttctgcga gtcacacacg ggaggagcgg gaagagctgg aagaaccatg   13680
tttttttttt tattccaaaa gattatccaa aacctcaaaa tgaagatcta ttaagtgaac   13740
gcgctcccct ccggtggcgt ggtcaaactc tacagccaaa gaacagataa tggcatttgt   13800
aagatgttgc acaatggctt ccaaaaggca aacggccctc acgtccaagt ggacgtaaag   13860
gctaaaccct tcagggtgaa tctcctctat aaacattcca gcaccttcaa ccatgcccaa   13920
ataattctca tctcgccacc ttctcaatat atctctaagc aaatcccgaa tattaagtcc   13980
ggccattgta aaaatctgct ccagagcgcc ctccaccttc agcctcaagc agcgaatcat   14040
gattgcaaaa attcaggttc ctcacagacc tgtataagat tcaaaagcgg aacattaaca   14100
aaaataccgc gatcccgtag gtcccttcgc agggccagct gaacataatc gtgcaggtct   14160
gcacggacca gcgcggccac ttccccgcca ggaaccttga caaagaacc cacactgatt    14220 atgacacgca tactcggagc tatgctaacc agcgtagccc cgatgtaagc tttgttgcat   14280
gggcggcgat ataaaatgca aggtgctgct caaaaaatca ggcaaagcct cgcgcaaaaa   14340
agaaagcaca tcgtagtcat gctcatgcag ataaaggcag gtaagctccg gaaccaccac   14400
agaaaaagac accattttc tctcaaacat gtctgcgggt ttctgcataa acacaaaata    14460
aaataacaaa aaaacattta acattagaa gcctgtctta caacaggaaa acaacccctt    14520
ataagcataa gacggactac ggccatgccg gcgtgaccgt aaaaaactg gtcaccgtga    14580 ttaaaaagca ccaccgacag ctcctcggtc atgtccggag tcataatgta agactcggta   14640
aacacatcag gttgattcat cggtcagtgc taaaaagcga ccgaaatagc ccgggggaat   14700
acatacccgc aggcgtagag acaacattac agcccccata ggaggtataa caaaattaat   14760
aggagagaaa aacacataaa cacctgaaaa accctcctgc ctaggcaaaa tagcaccctc   14820
ccgctccaga acaacataca gcgcttcaca gcggcagcct aacagtcagc cttaccagta   14880
aaaaagaaaa cctattaaaa aaacaccact cgacacggca ccagctcaat cagtcacagt   14940
gtaaaaaagg gccaagtgca gagcgagtat atataggact aaaaaatgac gtaacggtta   15000
aagtccacaa aaaacaccca gaaaaccgca cgcgaaccta cgcccagaaa cgaaagccaa   15060
aaaacccaca acttcctcaa atcgtcactt ccgttttccc acgttacgta acttcccatt   15120
ttaagaaaac tacaattccg tcacaaactc cacccctca ttatcatatt ggcttcaatc     15180
caaaataagg tatattattg atgatttatt ttggattgaa gccaatatga taatgagggg   15240
gtggagtttg tgacgtggcg cggggcgtgg gaacggggcg ggtgacgtag tagtgtggcg   15300
gaagtgtgat gttgcaagtg tggcggaaca catgtaagcg acggatgtgg caaaagtgac   15360 gttttggtg tgcgccggat ccacaggacg ggtgtggtcg ccatgatcgc gtagtcgata    15420
gtggctccaa gtagcgaagc gagcaggact gggcggcggc caaagcggtc ggacagtgct   15480
```

```
ccgagaacgg gtgcgcatag aaattgcatc aacgcatata gcgctagcag cacgccatag    15540
tgactggcga tgctgtcgga atggacgata tcccgcaaga ggcccggcag taccggcata    15600
accaagccta tgcctacagc atccagggtg acggtgccga ggatgacgat gagcgcattg    15660
ttagatttca tacacggtgc ctgactgcgt tagcaattta actgtgataa actaccgcat    15720
taaagcttat cgataagctt gatatcgaat tcctgcagcc cggggatcc actagttcta     15780 gagcggccgc caccgcggtg gagctccaat tcgccctata gtgagtcgta ttacgcgcgc    15840
tcactggccg tcgttttaca acgtcgtgac tgggaaaacc ctggcgttac ccaacttaat    15900
cgccttgcag cacatccccc tttcgccagc tggcgtaata gcgaagaggc ccgcaccgat    15960
cgcccttccc aacagttgcg cagcctgaat ggcgaatgga aattgtaagc gttaatattt    16020
tgttaaaatt cgcgttaaat ttttgttaaa tcagctcatt ttttaaccaa taggccgaaa    16080
tcggcaaaat cccttataaa tcaaaagaat agaccgagat agggttgagt gttgttccag    16140
tttggaacaa gagtccacta ttaaagaacg tggactccaa cgtcaaaggg cgaaaaaccg    16200
tctatcaggg cgatggccca ctacgtgaac catcacccta atcaagtttt tggggtcga    16260 ggtgccgtaa agcactaaat cggaacccta aagggagccc ccgatttaga gcttgacggg    16320
gaaagccggc gaacgtggcg agaaaggaag ggaagaaagc gaaaggagcg gcgctaggg    16380 cgctggcaag tgtagcggtc acgctgcgcg taaccaccac acccgccgcg cttaatgcgc    16440
cgctacaggg cgcgtcaggt ggcactttc ggggaaatgt gcgcggaacc cctatttgtt    16500
tatttttcta aatacattca aatatgtatc cgctcatgag acaataaccc tgataaatgc    16560
ttcaataata ttgaaaaagg aagagtatga gtattcaaca tttccgtgtc gcccttattc    16620
ccttttttgc ggcattttgc cttcctgttt ttgctcaccc agaaacgctg gtgaaagtaa    16680
aagatgctga agatcagttg ggtgcacgag tgggttacat cgaactggat ctcaacagcg    16740
gtaagatcct tgagagtttt cgccccgaag aacgttttcc aatgatgagc acttttaaag    16800
ttctgctatg tggcgcggta ttatcccgta ttgacgccgg gcaagagcaa ctcggtcgcc    16860
gcatacacta ttctcagaat gacttggttg agtactcacc agtcacagaa aagcatctta    16920
cggatggcat gacagtaaga gaattatgca gtgctgccat aaccatgagt gataacactg    16980
cggccaactt acttctgaca acgatcggag gaccgaagga gctaaccgct tttttgcaca    17040
acatggggga tcatgtaact cgccttgatc gttgggaacc ggagctgaat gaagccatac    17100
caaacgacga gcgtgacacc acgatgcctg tagcaatggc aacaacgttg cgcaaactat    17160
taactggcga actacttact ctagcttccc ggcaacaatt aatagactgg atggaggcgg    17220
ataaagttgc aggaccactt ctgcgctcgg cccttccggc tggctggttt attgctgata    17280
aatctggagc cggtgagcgt gggtctcgcg gtatcattgc agcactgggg ccagatggta    17340
agccctcccg tatcgtagtt atctacacga cggggagtca ggcaactatg gatgaacgaa    17400
atagacagat cgctgagata ggtgcctcac tgattaagca ttggtaactg tcagaccaag    17460
tttactcata tatactttag attgatttaa aacttcattt ttaatttaaa aggatctagg    17520
tgaagatcct ttttgataat ctcatgacca aaatccctta acgtgagttt tcgttccact    17580
gagcgtcaga ccccgtagaa aagatcaaag gatcttcttg agatcctttt tttctgcgcg    17640
taatctgctg cttgcaaaca aaaaaaccac cgctaccagc ggtggtttgt ttgccggatc    17700
aagagctacc aactcttttt ccgaaggtaa ctggcttcag cagagcgcag ataccaaata    17760
ctgtccttct agtgtagccg tagttaggcc accacttcaa gaactctgta gcaccgccta    17820
```

| | |
|---|---:|
| catacctcgc tctgctaatc ctgttaccag tggctgctgc cagtggcgat aagtcgtgtc | 17880 |
| ttaccgggtt ggactcaaga cgatagttac cggataaggc gcagcggtcg ggctgaacgg | 17940 |
| ggggttcgtg cacacagccc agcttggagc gaacgaccta caccgaactg agatacctac | 18000 |
| agcgtgagct atgagaaagc gccacgcttc ccgaagggag aaaggcggac aggtatccgg | 18060 |
| taagcggcag ggtcggaaca ggagagcgca cgagggagct tccaggggga aacgcctggt | 18120 |
| atctttatag tcctgtcggg tttcgccacc tctgacttga gcgtcgattt ttgtgatgct | 18180 |
| cgtcagggg gcggagccta tggaaaaacg ccagcaacgc ggccttttta cggttcctgg | 18240 |
| ccttttgctg gccttttgct cacatgttct ttcctgcgtt atccctgat tctgtggata | 18300 |
| accgtattac cgcctttgag tgagctgata ccgctcgccg cagccgaacg accgagcgca | 18360 |
| gcgagtcagt gagcgaggaa gcggaagagc gcccaatacg caaaccgcct ctccccgcgc | 18420 |
| gttggccgat tcattaatgc agctggcacg acaggtttcc cgactggaaa gcgggcagtg | 18480 |
| agcgcaacgc aattaatgtg agttagctca ctcattaggc acccaggct ttacactta | 18540 |
| tgcttccggc tcgtatgttg tgtggaattg tgagcggata acaatttcac acaggaaaca | 18600 |
| gctatgacca tgattacgcc aagcgcgcaa ttaaccctca ctaaagggaa caaaagctgg | 18660 |
| gtac | 18664 |

<210> SEQ ID NO 3
<211> LENGTH: 7389
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---:|
| tcgaggacaa ccttagtgaa ggaattcgcg agtggtgggc tttgaaacct ggagcccctc | 60 |
| aacccaaggc aaatcaacaa catcaagaca acgctcgagg tcttgtgctt ccgggttaca | 120 |
| aataccttgg acccggcaac ggactcgaca aggggagcc ggtcaacgca gcagacgcgg | 180 |
| cggccctcga gcacgacaag gcctacgacc agcagctcaa ggccggagac aacccgtacc | 240 |
| tcaagtacaa ccacgccgac gccgagttcc aggagcggct caaagaagat acgtcttttg | 300 |
| ggggcaacct cgggcgagca gtcttccagg ccaaaaagag gcttcttgaa cctcttggtc | 360 |
| tggttgagga agcggctaag acggctcctg gaaagaagag gcctgtagag cagtctcctc | 420 |
| aggaaccgga ctcctccgcg ggtattggca atcgggtgc acagcccgct aaaaagagac | 480 |
| tcaatttcgg tcagactggc gacacagagt cagtcccaga ccctcaacca atcggagaac | 540 |
| ctcccgcagc cccctcaggt gtgggatctc ttacaatggc ttcaggtggt ggcgcaccag | 600 |
| tggcagacaa taacgaaggt gccgatgag tgggtagttc ctcgggaaat tggcattgcg | 660 |
| attcccaatg gctgggggac agagtcatca ccaccagcac ccgaacctgg gccctgccca | 720 |
| cctacaacaa tcacctctac aagcaaatct ccaacagcac atctggagga tcttcaaatg | 780 |
| acaacgccta cttcggctac agcaccccct ggggtattt tgacttcaac agattccact | 840 |
| gccacttctc accacgtgac tggcagcgac tcatcaacaa caactgggga ttccggccta | 900 |
| agcgactcaa cttcaagctc ttcaacattc aggtcaaaga ggttacggac aacaatggag | 960 |
| tcaagaccat cgccaataac cttaccagca cggtccaggt cttcacggac tcagactatc | 1020 |
| agctcccgta cgtgctcggg tcggctcacg agggctgcct cccgccgttc ccagcggacg | 1080 |
| ttttcatgat tcctcagtac gggtatctga cgcttaatga tggaagccag gccgtgggtc | 1140 |
| gttcgtcctt ttactgcctg gaatatttcc cgtcgcaaat gctaagaacg ggtaacaact | 1200 |

```
tccagttcag ctacgagttt gagaacgtac cttccatag cagctacgct cacagccaaa    1260
gcctggaccg actaatgaat ccactcatcg accaatactt gtactatctc tcaaagacta    1320
ttaacggttc tggacagaat caacaaacgc taaaattcag tgtggccgga cccagcaaca    1380
tggctgtcca gggaagaaac tacatacctg gacccagcta ccgacaacaa cgtgtctcaa    1440
ccactgtgac tcaaaacaac aacagcgaat ttgcttggcc tggagcttct tcttgggctc    1500
tcaatggacg taatagcttg atgaatcctg acctgctat ggccagccac aaagaaggag    1560
aggaccgttt ctttcctttg tctggatctt taattttgg caaacaagga actggaagag    1620
acaacgtgga tgcggacaaa gtcatgataa ccaacgaaga agaaattaaa actactaacc    1680
cggtagcaac ggagtcctat ggacaagtgg ccacaaacca ccagagtgcc caagcacagg    1740
cgcagaccgg ctgggttcaa aaccaaggaa tacttccggg tatggtttgg caggacagag    1800
atgtgtacct gcaaggaccc atttgggcca aaattcctca cacggacggc aactttcacc    1860
cttctccgct gatgggaggg tttgaatga agcacccgcc tcctcagatc ctcatcaaaa    1920
acacacctgt acctgcggat cctccaacgg ccttcaacaa ggacaagctg aactctttca    1980
tcacccagta ttctactggc caagtcagcg tggagatcga gtgggagctg cagaaggaaa    2040
acagcaagcg ctggaacccg gagatccagt acacttccaa ctattacaag tctaataatg    2100
ttgaatttgc tgttaatact gaaggtgtat atagtgaacc ccgccccatt ggcaccagat    2160
acctgactcg taatctgtaa ttgcttgtta atcaataaac cgtttaattc gtttcagttg    2220
aactttggtc tctgcgaagg gcgaattcgt ttaaacctgc aggactagag tcctgtatta    2280
gaggtcacgt gagtgttttg cgacattttg cgacaccatg tggtcacgct gggtatttaa    2340
gcccgagtga gcacgcaggg tctccatttt gaagcgggag gtttgaacgc gcagccgcca    2400
agccgaattc tgcagatatc catcacactg gcggccgctc gactagagcg gccgccaccg    2460
cggtggagct ccagcttttg ttccctttag tgagggttaa ttgcgcgctt ggcgtaatca    2520
tggtcatagc tgtttcctgt gtgaaattgt tatccgctca caattccaca acatacga    2580 gccgaagca taaagtgtaa agcctggggt gcctaatgag tgagctaact cacattaatt    2640
gcgttgcgct cactgcccgc tttccagtcg ggaaacctgt cgtgccagct gcattaatga    2700
atcggccaac gcgcggggag aggcggtttg cgtattgggc gctcttccgc ttcctcgctc    2760
actgactcgc tgcgctcggt cgttcggctg cggcgagcgg tatcagctca ctcaaaggcg    2820
gtaatacggt tatccacaga atcaggggat aacgcaggaa agaacatgtg agcaaaaggc    2880
cagcaaaagg ccaggaaccg taaaaaggcc gcgttgctgg cgtttttcca taggctccgc    2940 cccccctgacg agcatcacaa aaatcgacgc tcaagtcaga ggtggcgaaa cccgacagga    3000
ctataaagat accaggcgtt tccccctgga agctccctcg tgcgctctcc tgttccgacc    3060
ctgccgctta ccggatacct gtccgccttt ctcccttcgg gaagcgtggc gctttctcat    3120
agctcacgct gtaggtatct cagttcggtg taggtcgttc gctccaagct gggctgtgtg    3180
cacgaacccc ccgttcagcc cgaccgctgc gccttatccg gtaactatcg tcttgagtcc    3240
aacccggtaa gacacgactt atcgccactg gcagcagcca ctggtaacag gattagcaga    3300
gcgaggtatg taggcggtgc tacagagttc ttgaagtggt ggcctaacta cggctacact    3360
agaaggacag tatttggtat ctgcgctctg ctgaagccag ttaccttcgg aaaaagagtt    3420
ggtagctctt gatccggcaa acaaaccacc gctggtagcg gtggtttttt tgtttgcaag    3480
cagcagatta cgcgcagaaa aaaaggatct caagaagatc ctttgatctt ttctacgggg    3540
```

```
tctgacgctc agtggaacga aaactcacgt taagggattt tggtcatgag attatcaaaa    3600
aggatcttca cctagatcct tttaaattaa aaatgaagtt ttaaatcaat ctaaagtata    3660
tatgagtaaa cttggtctga cagttaccaa tgcttaatca gtgaggcacc tatctcagcg    3720
atctgtctat ttcgttcatc catagttgcc tgactcccg tcgtgtagat aactacgata    3780
cgggagggct taccatctgg ccccagtgct gcaatgatac cgcgagaccc acgctcaccg    3840
gctccagatt tatcagcaat aaaccagcca gccggaaggg ccgagcgcag aagtggtcct    3900
gcaactttat ccgcctccat ccagtctatt aattgttgcc gggaagctag agtaagtagt    3960
tcgccagtta atagtttgcg caacgttgtt gccattgcta caggcatcgt ggtgtcacgc    4020
tcgtcgtttg gtatggcttc attcagctcc ggttcccaac gatcaaggcg agttacatga    4080
tcccccatgt tgtgcaaaaa agcggttagc tccttcggtc ctccgatcgt tgtcagaagt    4140
aagttggccg cagtgttatc actcatggtt atggcagcac tgcataattc tcttactgtc    4200
atgccatccg taagatgctt tctgtgactg gtgagtactc aaccaagtca ttctgagaat    4260
agtgtatgcg gcgaccgagt tgctcttgcc cggcgtcaat acgggataat accgcgccac    4320
atagcagaac tttaaaagtg ctcatcattg gaaaacgttc ttcggggcga aaactctcaa    4380
ggatcttacc gctgttgaga tccagttcga tgtaacccac tcgtgcaccc aactgatctt    4440
cagcatcttt tactttcacc agcgtttctg ggtgagcaaa aacaggaagg caaaatgccg    4500
caaaaaaggg aataagggcg acacggaaat gttgaatact catactcttc ctttttcaat    4560
attattgaag catttatcag ggttattgtc tcatgagcgg atacatattt gaatgtattt    4620
agaaaaataa acaaataggg gttccgcgca catttccccg aaaagtgcca cctaaattgt    4680
aagcgttaat attttgttaa aattcgcgtt aaattttgt taaatcagct cattttttaa    4740
ccaataggcc gaaatcggca aaatccctta taaatcaaaa gaatagaccg agatagggtt    4800
gagtgttgtt ccagtttgga acaagagtcc actattaaag aacgtggact ccaacgtcaa    4860
agggcgaaaa accgtctatc agggcgatgg cccactacgt gaaccatcac cctaatcaag    4920
ttttttgggg tcgaggtgcc gtaaagcact aaatcggaac cctaaaggga gcccccgatt    4980
tagagcttga cggggaaagc cggcgaacgt ggcgagaaag gaagggaaga agcgaaagg    5040
agcgggcgct agggcgctgg caagtgtagc ggtcacgctg cgcgtaacca ccacacccgc    5100
cgcgcttaat gcgccgctac agggcgcgtc ccattcgcca ttcaggctgc gcaactgttg    5160
ggaagggcga tcggtgcggg cctcttcgct attacgccag ctggcgaaag ggggatgtgc    5220
tgcaaggcga ttaagttggg taacgccagg gttttcccag tcacgacgtt gtaaaacgac    5280
ggccagtgag cgcgcgtaat acgactcact atagggcgaa ttgggtaccg gccccccct    5340
cgatcgaggt cgacggtatc gggggagctc ggatccacta gtaacggccg ccagtgtgct    5400
ggattcggct ttatttaagc ccgagtgagc acgcagggtc tccattttga agcgggaggt    5460
ttgaacgcgc agccgccatg ccgggggtttt acgagattgt gattaaggtc cccagcgacc    5520
ttgacgggca tctgcccggc atttctgaca gctttgtgaa ctgggtggcc gagaaggaat    5580
gggagttgcc gccagattct gacatggatc tgaatctgat tgagcaggca ccctgaccg    5640
tggccgagaa gctgcagcgc gactttctga cggaatggcg ccgtgtgagt aaggcccgg    5700
aggcccttt ctttgtgcaa tttgagaagg gagagagcta cttccacatg cacgtgctcg    5760
tggaaaccac cggggtgaaa tccatggttt tgggacgttt cctgagtcag attcgcgaaa    5820
aactgattca gagaatttac cgcgggatcg agccgacttt gccaaactgg ttcgcggtca    5880
caaagaccag aaatggcgcc ggaggcggga acaaggtggt ggatgagtgc tacatcccca    5940
```

-continued

```
attacttgct cccaaaacc cagcctgagc tccagtgggc gtggactaat atggaacagt    6000
atttaagcgc ctgtttgaat ctcacggagc gtaaacggtt ggtggcgcag catctgacgc    6060
acgtgtcgca gacgcaggag cagaacaaag agaatcagaa tcccaattct gatgcgccgg    6120
tgatcagatc aaaaacttca gccaggtaca tggagctggt cgggtggctc gtggacaagg    6180
ggattacctc ggagaagcag tggatccagg aggaccaggc ctcatacatc tccttcaatg    6240
cggcctccaa ctcgcggtcc caaatcaagg tgccttggac aatgcgggaa agattatgag    6300
cctgactaaa accgccccg actacctggt gggccagcag cccgtggagg acatttccag    6360
caatcggatt tataaaattt tggaactaaa cgggtacgat ccccaatatg cggcttccgt    6420
ctttctggga tgggccacga aaaagttcgg caagaggaac accatctggc tgtttgggcc    6480
tgcaactacc gggaagacca acatcgcgga ggccatagcc cacactgtgc ccttctacgg    6540
gtgcgtaaac tggaccaatg agaactttcc cttcaacgac tgtgtcgaca agatggtgat    6600
ctggtgggag gaggggaaga tgaccgccaa ggtcgtggag tcggccaaag ccattctcgg    6660
aggaagcaag gtgcgcgtgg accagaaatg caagtcctcg gcccagatag acccgactcc    6720
cgtgatcgtc acctccaaca ccaacatgtg cgccgtgatt gacgggaact caacgacctt    6780
cgaacaccag cagccgttgc aagaccggat gttcaaattt gaactcaccc gccgtctgga    6840
tcatgacttt gggaaggtca ccaagcagga agtcaaagac tttttccggt gggcaaagga    6900
tcacgtggtt gaggtggagc atgaattcta cgtcaaaaag ggtggagcca agaaaagacc    6960
cgccccagt gacgcagata taagtgagcc caaacgggtg cgcgagtcag ttgcgcagcc    7020
atcgacgtca gacgcggaag cttcgatcaa ctacgcggac aggtaccaaa acaaatgttc    7080
tcgtcacgtg ggcatgaatc tgatgctgtt cccctgcaga caatgcgaga gactgaatca    7140
gaattcaaat atctgcttca ctcacggtgt caaagactgt ttagagtgct ttcccgtgtc    7200
agaatctcaa cccgtttctg tcgtcaaaaa ggcgtatcag aaactgtgct acattcatca    7260
catcatggga aaggtgccag acgcttgcac tgcttgcgac ctggtcaatg tggacttgga    7320
tgactgtgtt tctgaacaat aaatgactta aaccaggtat ggctgccgat ggttatcttc    7380
cagattggc                                                             7389
```

COMPOSITIONS AND METHODS FOR PURIFYING RECOMBINANT ADENO-ASSOCIATED VIRUS

CROSS-REFERENCE TO RELATED APPLICATIONS

This application is a national stage filing under 35 U.S.C. § 371 of International PCT application PCT/US2015/039005, filed Jul. 2, 2015, which claims the benefit under 35 U.S.C. § 119(e) of U.S. provisional application No. 62/020,315, filed Jul. 2, 2014, which is incorporated by reference herein in its entirety.

FEDERALLY SPONSORED RESEARCH OR DEVELOPMENT

This invention was made with government support under HL097088 and HL059412 awarded by the National Institutes of Health. The government has certain rights in the invention.

BACKGROUND OF THE INVENTION

Recombinant Adeno-associated virus (rAAV) vectors (also referred to as rAAV particles herein) have emerged as one of the most versatile and successful gene therapy delivery vehicles. A number of clinical trials successfully commenced recently (Mueller and Flotte, 2008; High, 2011; High and Aubourg, 2011; Mingozzi and High, 2011; Nathwani et al., 2011; Asokan et al., 2012) and patients diagnosed with lipoprotein lipase deficiency will now have an option to be treated with Glybera®, the first rAAV-based drug to win the regulatory approval of the European Commission. However, even though the industry is poised for the expansion into several application areas represented by orphan diseases, a simple and scalable rAAV production technology is still lacking.

SUMMARY OF THE INVENTION

Aspects of the disclosure are based, in part, on the development of a method of purifying rAAV particles that is rapid, cost-effective, and results in an unexpectedly more highly purified rAAV product compared to previous methods.

Accordingly, aspects of the disclosure relate to methods of purifying rAAV particles. As described herein, it was found that rAAV particles remained in suspension under low pH conditions that caused flocculation of the majority of cellular components in a cell lysate. These low pH conditions also did not significantly damage the rAAV particles. Accordingly, aspects of the disclosure relate to a simple technique of enriching a sample for rAAV particles. In some embodiments, the method comprises reducing the pH of a cell lysate comprising rAAV particles to less than or equal to 5 to produce a flocculate and a supernatant comprising the rAAV particles and isolating the supernatant comprising the rAAV particles from the flocculate. In some embodiments, a further purification technique can be used to purify the rAAV particles from the supernatant, such as a purification technique known in the art or described herein. Exemplary purification techniques include iodixanol step gradient, CsCl gradient, chromatography, or polyethylene glycol (PEG) precipitation.

In some embodiments, also as described herein, it was found that the rAAV particles contained within the supernatant after flocculation by low pH could be purified using cation exchange chromatography to produce a preparation of rAAV particles with high purity. Accordingly, in some embodiments, the method comprises reducing the pH of a cell lysate comprising rAAV particles to less than or equal to 5 to produce a flocculate and a supernatant comprising the rAAV particles, isolating the supernatant comprising the rAAV particles from the flocculate, and purifying the rAAV particles from the supernatant using cation exchange chromatography, thereby producing purified rAAV particles.

In some embodiments, also as described herein, it was found that rAAV particles purified from the supernatant could be further purified in order to produce high titer and GMP-quality rAAV preparations. Accordingly, in some embodiments, the method comprises reducing the pH of a cell lysate comprising rAAV particles to less than or equal to 5 to produce a flocculate and a supernatant comprising the rAAV particles, isolating the supernatant comprising the rAAV particles from the flocculate, and purifying the rAAV particles from the supernatant using cation exchange chromatography, thereby producing purified rAAV particles, and further purifying and/or concentrating the purified rAAV particles. The further purification and/or concentration may be performed using any method known in the art or described herein. In some embodiments, further purifying and/or concentrating the purified rAAV particles comprises tangential flow filtration and/or centrifugation.

In some embodiments, the method comprises:
a) providing a cell lysate having a pH of between 6 and 9 and comprising rAAV particles;
b) reducing the pH of the cell lysate to less than or equal to 5 to produce a flocculate and a supernatant comprising the rAAV particles;
c) isolating the supernatant comprising the rAAV particles from the flocculate; and
d) purifying the rAAV particles from the supernatant using cation exchange chromatography, thereby producing purified rAAV particles.

In some embodiments of any one of the methods provided herein, reducing the pH comprises contacting the cell lysate comprising the rAAV particles with a triprotic acid. In some embodiments of any one of the methods provided herein, the triprotic acid is citric acid. In some embodiments of any one of the methods provided herein, reducing the pH comprises contacting the cell lysate comprising the rAAV particles with 100 mM citric acid.

In some embodiments of any one of the methods provided herein, the cell lysate further comprises sodium citrate. In some embodiments of any one of the methods provided herein, the cell lysate further comprises an endonuclease. In some embodiments of any one of the methods provided herein, the cell lysate further comprises $Mg^{2+}$ and benzonase. In some embodiments of any one of the methods provided herein, the sodium citrate is 16 mM sodium citrate.

In some embodiments of any one of the methods provided herein, isolating the supernatant comprising the rAAV particles from the flocculate comprises isolating the supernatant comprising the rAAV particles from the flocculate by centrifugation or filtration. In some embodiments of any one of the methods provided herein, isolating the supernatant comprising the rAAV particles from the flocculate comprises isolating the supernatant comprising the rAAV particles from the flocculate by centrifugation.

In some embodiments of any one of the methods provided herein, the cell lysate is a mammalian or insect cell lysate. In some embodiments of any one of the methods provided herein, the cell lysate is HEK293 or Sf9 producer cell lysate.

In some embodiments of any one of the methods provided herein, the cation exchange chromatography is sulfopropyl column chromatography.

In some embodiments of any one of the methods provided herein, the method further comprises:

further purifying and/or concentrating the purified rAAV particles by tangential flow filtration and/or centrifugation, thereby producing further purified and/or concentrated rAAV particles.

In some embodiments of any one of the methods provided herein, the cell lysate is produced by microfluidization, sonication, freeze/thawing, or hypotonic lysis of cells comprising the rAAV particles. In some embodiments of any one of the methods provided herein, the cell lysate is produced by hypotonic lysis of cells comprising the rAAV particles. In some embodiments of any one of the methods provided herein, the cell lysate is produced by microfluidization.

In some embodiments of any one of the methods provided herein, reducing the pH of the cell lysate to less than or equal to 5 to produce a flocculate and a supernatant comprising the rAAV particles comprises reducing the pH of the cell lysate comprising the rAAV particles to between pH 3 and 5. In some embodiments of any one of the methods provided herein, reducing the pH of the cell lysate to less than or equal to 5 to produce a flocculate and a supernatant comprising the rAAV particles comprises reducing the pH of the cell lysate comprising the rAAV particles to between pH 3 and 4.

In some embodiments of any one of the methods provided herein, the rAAV particles are rAAV2, rAAV8 or rAAV9 particles. In some embodiments of any one of the methods provided herein, the rAAV particles are rAAV8 or rAAV9 particles. In some embodiments of any one of the methods provided herein, the rAAV particles are rAAV9 particles.

In some embodiments of any one of the methods provided herein, the purified rAAV particles or the further purified and/or concentrated rAAV particles are added to a pharmaceutical composition. In some embodiments, the pharmaceutical composition comprises a pharmaceutically acceptable carrier. In some embodiments, the pharmaceutical composition is administered to a subject in need thereof.

Other aspects of the disclosure relate to compositions comprising rAAV particles. In some embodiments, the composition comprises rAAV particles having a purity of above 90%. In some embodiments, the composition comprises purified rAAV particles or further purified and/or concentrated rAAV particles produced by or obtainable by any one of the methods described herein.

Yet other aspects of the disclosure relate to a method, comprising administering a composition described herein (e.g., a composition comprising rAAV particles having a purity of above 90% or a composition comprising purified rAAV particles or further purified and/or concentrated rAAV particles produced by or obtainable by any one of the methods described herein) to a subject in need thereof.

Other aspects of the disclosure relate to kits, e.g., kits for performing a method described herein. In some embodiments, the kit comprises water for injection (WFI), sodium citrate and citric acid. In some embodiments, the kit further comprises a sulfopropyl (SP) resin chromatography column. In some embodiments, the kit further comprises a filtration concentrator.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 3A—SP column chromatography profile of rAAV9 purification. Solid line indicates $OD_{280}$ (mAU), dashed line—measured electric conductance (mS/cm). FIG. 3B—Silver-stain SDS protein gel analysis of rAAV9 purification steps. Fractions are: "Benzo"—crude lysate treated with benzonase; "SP load"—supernatant after flocculation/centrifugation step; "SP FT"—SP column flowthrough; "SP 50% B"—fraction containing rAAV9 eluted from the column with the buffer mixture containing 50% buffer B; "TFF"—tangential flow filtration fraction (final purified rAAV9 stock); "293 iodixanol"—positive control, rAAV9 purified by 'conventional' iodixanol buoyant density gradient. FIG. 3C—Western blotting analysis of the final purified rAAV9 fraction (TFF), side-by-side with positive control; left panel—adjusted gel load sample volumes; right panel—same sample volumes as in FIG. 3B. Higher sample loads allow visualizing VP-derived, B1-immunoreactive peptides but result in "burnt out" effect in the X-ray film for some peptides (e.g., VP3). FIG. 3D, E—Electron microscopy. Negative stain images of rAAV9 purified using the sodium citrate method (FIG. 3D), or using discontinuous step gradient of iodixanol (FIG. 3E)[ref. 8]. The inserts in the lower right hand corner are close-up images of the virus capsids. Filled arrowheads point at the DNA-containing particles; empty arrowheads—at the empty capsids; black asterisk indicates proteasome; white asterisk—deformed AAV particle. FIG. 3F—Graphical representation of the rAAV9-GFP yields at all purification steps, as titered for the genome-containing particles (dot-blot assay, black bars, or PCR assay, grey bars); and infectious particles (green cell assay, GCA, white bars). The missing bars for some steps indicate the titers below 10E4, the Y-axis plotting scale.

FIGS. 4A-D are a series of graphs and photographs showing an exemplary rAAV2 purification. FIG. 4A—SP column chromatography profile of rAAV2 purification.

Solid line indicates OD$_{280}$ (mAU), dashed line—measured electric conductance (mS/cm). FIG. 4B—Silver-stain SDS protein gel analysis of rAAV2 purification steps. Fractions are as following: "Benzo"—crude lysate treated with benzonase; "SP load"—supernatant after flocculation/centrifugation step; "SP FT"—SP column flowthrough; "SP 10% B"—fraction containing rAAV2 eluted from the column with the buffer mixture containing 10% buffer B; "SP 20% B"—20% buffer B; "TFF"—tangential flow filtration fraction (final purified rAAV2 stock); "293 iodixanol"—positive control, rAAV2 purified by 'conventional' iodixanol buoyant density gradient. FIG. 4C—Western blotting analysis of the final purified rAAV2 fraction (TFF), side-by-side with positive control; left panel—adjusted gel load sample volumes; right panel—same sample volumes as in FIG. 4B. FIG. 4D—Graphical representation of the rAAV2-GFP yields at all purification steps, as titered for the genome-containing particles (dot-blot assay, black bars, or PCR assay, grey bars); and infectious particles (green cell assay, GCA, white bars).

FIG. 5A—SP column chromatography profile of HEK 293-derived rAAV8 purification. Solid line indicates OD$_{280}$ (mAU), dashed line—measured electric conductance (MS/CM). FIG. 5B—SP column chromatography profile of Sf9-derived rAAV8 purification. FIG. 5C—Silver-stain SDS protein gel analysis of rAAV8 purification steps. Fractions are as following: "293"—sample derived from chromatography shown in Panel A; "Sf9"—sample derived from chromatography shown in Panel B; "Benzo"—crude lysate treated with benzonase; "SP load"—supernatant after flocculation/centrifugation step; "SP FT"—SP column flowthrough; "SP 50% B"—fraction containing rAAV8 eluted from the column with the buffer mixture containing 50% buffer B (see the Methods section for details); "TFF"—tangential flow filtration fraction (final purified rAAV8 stock); "293 iodixanol"—positive control, rAAV8 purified by 'conventional' iodixanol buoyant density gradient. FIG. 5D—Western blotting analysis of the final purified rAAV8 fraction (TFF), side-by-side with positive control; left panel—adjusted gel load sample volumes; right panel—same sample volumes as in FIG. 5C. FIG. 5E, F—Graphical representation of the rAAV8-GFP yields from HEK 293 cells (FIG. 5E), or from Sf9 cells (FIG. 5F) at all purification steps, as titered for the genome-containing particles (dot-blot assay, black bars, or PCR assay, grey bars); and infectious particles (green cell assay, GCA, white bars). The missing bars for some steps indicate the titers below 10E4, the Y-axis plotting scale.

DETAILED DESCRIPTION OF THE INVENTION

Figure 1:
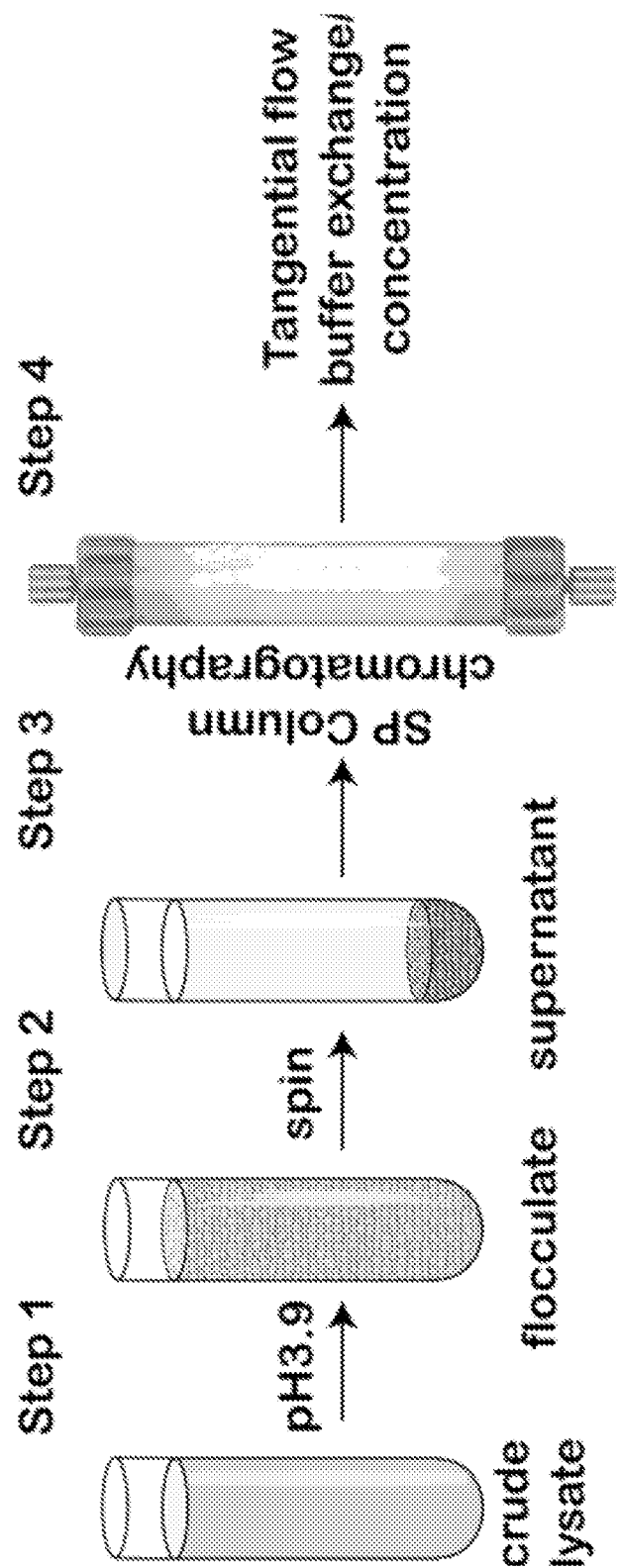
FIG. 1 depicts a schematic flowchart of an exemplary AAV purification protocol. A crude cell lysate is acidified by the addition of citric acid (Step 1). A heavy flocculate is precipitated by a low spin centrifugation (Step 2). A supernatant is subjected to a one-step cation-exchange chromatography (Step 3). Eluted virus is dialyzed/concentrated using tangential flow filtration (Step 4).

The ever growing rAAV vector toolbox, in addition to many natural AAV serotypes, now includes numerous AAV capsid mutants derived from combinatorial libraries or through rational engineering (Zhong et al., 2008; Asokan et al., 2012). To purify all these divergent AAV variants, buoyant density gradients such as CsCl, or iso-osmotic medium iodixanol discontinuous gradients (Zolotukhin et al., 1999) are routinely used. Although quite useful in a laboratory setting, these procedures are not easily adapted for Good Manufacturing Practice (GMP) protocols. In this regard, the most promising approach incorporates chromatography steps, either affinity, hydrophobic, or ion-exchange, depending on the biochemical properties of a particular serotype. For example, heparin affinity chromatography based on interaction with heparan sulfate proteoglycan has been successfully applied to rAAV2 (Clark et al., 1999; Zolotukhin et al., 1999), while mucin affinity chromatography was used for rAAV5 purification (Auricchio et al., 2001). Many successful examples of one- or two-step ion-exchange chromatography purification have been reported for rAAV serotypes 1, 2, 4, 5, and 8 (Brument et al., 2002; Kaludov et al., 2002; Zolotukhin et al., 2002; Davidoff et al., 2004; Okada et al., 2009). More recently, an affinity media incorporating anti-AAV VHH ligand, a single-domain camelid antibody derivative, was utilized to purify serotypes 1, 2, 3, and 5 (Hellstrom et al., 2009). In spite of these documented successful examples, some AAV serotypes, such as rAAV9, were refractory to conventional chromatography procedures and required significant effort and exceptional laboratory skills for the purification (Zhou et al., 2011).

As described herein, a rapid and reproducible protocol for rAAV particle purification has been developed based on a partial purification of an initial crude lysate by flocculation of cell debris under low pH conditions, which can be followed by, e.g., one-step cation-exchange chromatography. The flocculation step eliminates the bulk of the contaminating protein and DNA allowing for rAAV particle binding to, and subsequent elution from a resin, e.g., by cation exchange chromatography. Exposure of the rAAV particles to low pH conditions does not damage the rAAV particles. Methods described herein are contemplated for application to many serotypes, and in particular rAAV9 particles, and for rAAV particles purified from both mammalian and insect cell production systems.

Accordingly, aspects of the disclosure relate to methods of purifying rAAV particles, as well as compositions comprising the purified rAAV particles and uses thereof.

Methods

Aspects of the disclosure relate to methods of purifying recombinant adeno-associated virus (rAAV) particles.

In some embodiments, the method comprises: (a) providing a cell lysate comprising rAAV particles; (b) reducing the pH of the cell lysate to produce a flocculate and a supernatant comprising the rAAV particles; and (c) isolating the supernatant comprising the rAAV particles from the flocculate. In some embodiments, rAAV particles may be purified by from the supernatant, e.g., by a method known in the art or described herein. In some embodiments, rAAV particles may be purified from the supernatant by chromatography, such as cation exchange chromatography.

Accordingly, in some embodiments, the method comprises: (a) providing a cell lysate comprising rAAV particles; (b) reducing the pH of the cell lysate to produce a flocculate and a supernatant comprising the rAAV particles; (c) isolating the supernatant comprising the rAAV particles from the flocculate; and (d) purifying the rAAV particles from the supernatant using cation exchange chromatography, thereby producing purified rAAV particles. In some embodiments, the purified rAAV particles may be further purified and/or concentrated, e.g., by a method known in the art or described herein. In some embodiments, the further purification and/or concentration comprises TFF and/or centrifugation.

Accordingly, in some embodiments, the method comprises: (a) providing a cell lysate comprising rAAV particles; (b) reducing the pH of the cell lysate to produce a flocculate and a supernatant comprising the rAAV particles; (c) isolating the supernatant comprising the rAAV particles from the flocculate; (d) purifying the rAAV particles from the supernatant using cation exchange chromatography, thereby producing purified rAAV particles; and (e) further purifying and/or concentrating the purified rAAV particles, e.g., by TFF and/or centrifugation.

In some embodiments, reducing the pH in (b) in any one of the methods described herein comprises reducing the pH of the cell lysate to less than or equal to 5 to produce a flocculate and a supernatant comprising the rAAV particles. In some embodiments, reducing the pH in (b) in any one of the methods described herein comprises reducing the pH of the cell lysate to less than or equal to 4 (e.g., less than 4, less or equal to than 3.5, less than or equal to 3, less than or equal to 2.5, or less than or equal to 2) to produce a flocculate and a supernatant comprising the rAAV particles. In some embodiments, (b) in any one of the methods described herein comprises reducing the pH of the cell lysate comprising the rAAV particles to between pH 2 and 5 (e.g., 2 to 5, 2 to 4.5, 2 to 4, 2 to 3, 2.5 to 5, 2.5 to 4, 3 to 5, 3 to 4, 3.5 to 5, 3.5 to 4, or 4 to 5). In some embodiments, (b) in any one of the methods described herein comprises reducing the pH of the cell lysate comprising the rAAV particles to between pH 3 and 5. In some embodiments, (b) in any one of the methods described herein comprises reducing the pH of the cell lysate comprising the rAAV particles to between pH 2 and 4. In some embodiments, (b) in any one of the methods described herein comprises reducing the pH of the cell lysate comprising the rAAV particles to between pH 3 and 4. In some embodiments, (b) in any one of the methods described herein comprises reducing the pH of the cell lysate comprising the rAAV particles to between pH 3.5 and 4. In some embodiments, (b) in any one of the methods described herein comprises reducing the pH of the cell lysate comprising the rAAV particles to pH 3.9. pH can be measured or determined using any method known in the art or using a commercially available pH measuring device, e.g., a pH meter which may comprise a hydrogen-electrode, a quinhydron-electrode, or a glass electrode (see, e.g., products available from Hanna Instruments and Thermoscientific such as the Orion Star™ A111, A211 or A214 pH Benchtop Meter) or a pH indicator, e.g., a halochromic chemical compound, such as those listed in the table below. In some embodiments, the pH is measured using a pH meter with a glass electrode. In some embodiments, the pH may be determined based on a calculation, instead of a direct measurement. For example, compositions of acids and bases having a known pH may be mixed in a ratio that has been previously calculated to result in a particular pH.

| Indicator | Low pH color | Transition low end | Transition high end | High pH color |
|---|---|---|---|---|
| Gentian violet | yellow | 0.0 | 2.0 | blue-violet |
| Malachite green (first transition) | yellow | 0.0 | 2.0 | green |
| Malachite green (second transition) | | 11.6 | 14.0 | colorless |
| Thymol blue (first transition) | red | 1.2 | 2.8 | yellow |
| Thymol blue (second transition) | yellow | 8.0 | 9.6 | blue |
| Methyl yellow | red | 2.9 | 4.0 | yellow |
| Bromophenol blue | yellow | 3.0 | 4.6 | purple |
| Congo red | | 3.0 | 5.0 | red |
| Methyl orange | red | 3.1 | 4.4 | yellow |
| Screened methyl orange (first transition) | red | 0.0 | 3.2 | grey |
| Screened methyl orange (second transition) | grey | 3.2 | 4.2 | green |
| Bromocresol green | yellow | 3.8 | 5.4 | blue |
| Methyl red | red | 4.4 | 6.2 | yellow |
| Azolitmin | red | 4.5 | 8.3 | blue |
| Bromocresol purple | yellow | 5.2 | 6.8 | purple |
| Bromothymol blue | yellow | 6.0 | 7.6 | blue |
| Phenol red | yellow | 6.4 | 8.0 | red |
| Neutral red | red | 6.8 | 8.0 | yellow |
| Naphtholphthalein | colorless to reddish | 7.3 | 8.7 | greenish to blue |
| Cresol Red | yellow | 7.2 | 8.8 | reddish-purple |
| Cresolphthalein | colorless | 8.2 | 9.8 | purple |
| Phenolphthalein | colorless | 8.3 | 10.0 | fuchsia |
| Thymolphthalein | colorless | 9.3 | 10.5 | Blue |
| Alizarine Yellow R | yellow | 10.2 | 12.0 | Red |

In some embodiments, reducing the pH in (b) in any one of the methods described herein comprises contacting the cell lysate comprising the rAAV particles with an acid.

In some embodiments, the acid is provided as a liquid, suspension, emulsion, solid, or a combination of two or more thereof. In some embodiments, a liquid is an anhydrous liquid. In some embodiments, a liquid is a solution (e.g., an aqueous solution). Accordingly, in some embodiments an acid is provided in a solution (e.g., in an acid solution or in a buffer solution). In some embodiments, the acid is provided in a solid form (e.g., in a crystalline form, an amorphous form, a powder form, a salt form, or other solid form).

In some embodiments, an acid is a monoprotic acid, a triprotic acid, or any other suitable acid, or a combination of two or more thereof. In some embodiments, the acid is contained within a composition, e.g., within a solution or a buffer solution also comprising a base (such as sodium citrate or sodium phosphate as described below or elsewhere herein, or any other suitable buffer solution comprising a base). In some embodiments, the monoprotic acid is acetic acid. In some embodiments, the triprotic acid is citric acid (e.g., citric acid monohydrate) or phosphoric acid. In some embodiments, reducing the pH in (b) comprises contacting the cell lysate comprising the rAAV particles with citric acid. In some embodiments, reducing the pH in (b) comprises contacting the cell lysate comprising the rAAV particles with 10 mM-1M citric acid solution (e.g., 10 mM-1M, 10 mM-750 mM, 10 mM-500 mM, 10 mM-250 mM, 10 mM-100 mM, 25 mM-1M, 25 mM-750 mM, 25 mM-500 mM, 25 mM-250 mM, 25 mM-100 mM, 50 mM-1M, 50 mM-750 mM, 50 mM-500 mM, 50 mM-250 mM, 50 mM-100 mM, 75 mM-1M, 75 mM-750 mM, 75 mM-500 mM, 75 mM-250 mM, or 75 mM-100 mM) and 10 mM-1M sodium citrate solution (e.g., 10 mM-1M, 10 mM-750 mM, 10 mM-500 mM, 10 mM-250 mM, 10 mM-100 mM, 25 mM-1M, 25 mM-750 mM, 25 mM-500 mM, 25 mM-250 mM, 25 mM-100 mM, 50 mM-1M, 50 mM-750 mM, 50 mM-500 mM, 50 mM-250 mM, 50 mM-100 mM, 75 mM-1M, 75 mM-750 mM, 75 mM-500 mM, 75 mM-250 mM, or 75 mM-100 mM). It is to be appreciated that in different embodiments, different acids may be used. In some embodiments, if the cell lysate comprises sodium citrate, then the acid used is citric acid. In some embodiments, if the cell lysate comprises sodium phosphate, then the acid used is citric acid.

In some embodiments, a method is provided, wherein the method comprises: reducing the pH of a composition comprising cells containing rAAV particles to lyse the cells, thereby producing a flocculate and a supernatant comprising the rAAV particles; isolating the supernatant comprising the rAAV particles from the flocculate; and purifying the rAAV particles from the supernatant using cation exchange chromatography, thereby producing purified rAAV particles. In some embodiments, the pH of the composition is reduced to less than or equal to 5 (e.g., less than or equal to 5, less than or equal to 4.5, less than or equal to 4, less or equal to than 3.5, less than or equal to 3, less than or equal to 2.5, or less than or equal to 2). In some embodiments, the pH of the composition is reduced to between pH 2 and 5 (e.g., 2 to 5, 2 to 4.5, 2 to 4, 2 to 3, 2.5 to 5, 2.5 to 4, 3 to 5, 3 to 4, 3.5 to 5, 3.5 to 4, or 4 to 5).

In some embodiments, reducing the pH of the composition comprises contacting the composition with a buffer solution comprising a triprotic acid, e.g., citric acid, and citrate (e.g., sodium citrate such as trisodium citrate). In some embodiments, reducing the pH of the composition comprises contacting the composition with a buffer solution comprising a triprotic acid, e.g., citric acid, and phosphate (e.g., sodium phosphate such as dibasic sodium phosphate). In some embodiments, reducing the pH of the composition comprises contacting the composition with a buffer comprising 10 mM-1M citric acid (e.g., 10 mM-1M, 10 mM-750 mM, 10 mM-500 mM, 10 mM-250 mM, 10 mM-100 mM, 25 mM-1M, 25 mM-750 mM, 25 mM-500 mM, 25 mM-250 mM, 25 mM-100 mM, 50 mM-1M, 50 mM-750 mM, 50 mM-500 mM, 50 mM-250 mM, 50 mM-100 mM, 75 mM-1M, 75 mM-750 mM, 75 mM-500 mM, 75 mM-250 mM, or 75 mM-100 mM) and 10 mM-1M mM sodium citrate (e.g., 10 mM-1M, 10 mM-750 mM, 10 mM-500 mM, 10 mM-250 mM, 10 mM-100 mM, 25 mM-1M, 25 mM-750 mM, 25 mM-500 mM, 25 mM-250 mM, 25 mM-100 mM, 50 mM-1M, 50 mM-750 mM, 50 mM-500 mM, 50 mM-250 mM, 50 mM-100 mM, 75 mM-1M, 75 mM-750 mM, 75 mM-500 mM, 75 mM-250 mM, or 75 mM-100 mM). In some embodiments, reducing the pH of the composition comprises contacting the composition with a buffer comprising 10-50 mM citric acid (e.g., 10-50 mM, 20-40 mM, 30-40 mM or 34 mM citric acid) and 5-30 mM sodium citrate (e.g., 5-30 mM, 10-20 mM, or 16 mM sodium citrate). In some embodiments, the reducing the pH of the composition comprises contacting the composition with a buffer comprising sodium citrate and citric acid in a ratio of 16 to 34 sodium citrate to citric acid (Volume/Volume, v/v). Non-limiting, exemplary buffer solutions at non-limiting, exemplary pH ranges are provided in the tables below.

Exemplary Citric Acid—Sodium Citrate Buffer Solutions (x mL of 0.1M Solution of Citric Acid+y mL of 0.1 M Solution of Sodium Citrate)

| pH | x mL of 0.1M solution of citric acid* | y mL of 0.1M solution of sodium citrate** |
|---|---|---|
| 3.0 | 46.5 | 3.5 |
| 3.2 | 43.7 | 6.3 |
| 3.4 | 40.0 | 10.0 |
| 3.6 | 37.0 | 13.0 |
| 3.8 | 35.0 | 15.0 |
| 4.0 | 33.0 | 17.0 |
| 4.2 | 31.5 | 18.5 |
| 4.4 | 28.0 | 22.0 |
| 4.6 | 25.5 | 24.5 |
| 4.8 | 23.0 | 27.0 |
| 5.0 | 20.5 | 29.5 |
| 5.2 | 18.0 | 32.0 |
| 5.4 | 16.0 | 34.0 |
| 5.6 | 13.7 | 36.3 |
| 5.8 | 11.8 | 38.2 |
| 6.0 | 9.5 | 41.5 |
| 6.2 | 7.2 | 42.8 |

*Citric acid monohydrate, $C_6H_8O_7 \cdot H_2O$, Molecular weight = 210.14; 0.1M-solution contains 21.01 g/l.
**Trisodium citrate dihydrate, $C_6H_5O_7Na_3 \cdot 2H_2O$, Molecular weight = 294.12; 0.1M-solution contains 29.41 g/l.

Exemplary Citric Acid—Sodium Phosphate Buffer Solutions

Add the following to create 100 ml of phosphate/citrate buffer solution. Stock solutions are 0.2 M dibasic sodium phosphate; 0.1 M citric acid

| pH | 0.2M $Na_2HPO_4$ (ml)* | 0.1M citric acid (ml)** |
|---|---|---|
| 2.6 | 5.4 | 44.6 |
| 2.8 | 7.8 | 42.2 |
| 3.0 | 10.2 | 39.8 |
| 3.2 | 12.3 | 37.7 |
| 3.4 | 14.1 | 35.9 |
| 3.6 | 16.1 | 33.9 |
| 3.8 | 17.7 | 32.3 |
| 4.0 | 19.3 | 30.7 |
| 4.2 | 20.6 | 29.4 |
| 4.4 | 22.2 | 27.8 |
| 4.6 | 23.3 | 26.7 |
| 4.8 | 24.8 | 25.2 |
| 5.0 | 25.7 | 24.3 |
| 5.2 | 26.7 | 23.3 |
| 5.4 | 27.8 | 22.2 |
| 5.6 | 29.0 | 21.0 |
| 5.8 | 30.3 | 19.7 |
| 6.0 | 32.1 | 17.9 |
| 6.2 | 33.1 | 16.9 |
| 6.4 | 34.6 | 15.4 |
| 6.6 | 36.4 | 13.6 |
| 6.8 | 40.9 | 9.1 |
| 7.0 | 43.6 | 6.5 |

*$Na_2HPO_4$, Molecular weight = 141.98; 0.2M-solution contains 28.40 g/l, or $Na_2HPO_4 \cdot 2H_2O$, Molecular weight = 178.05; 0.2M-solution contains 35.61 g/l.
**Citric acid monohydrate, $C_6H_8O_7 \cdot H_2O$, Molecular weight 210.14; 0.1M-solution contains 21.01 g/l.

In some embodiments of any one of the methods provided herein, the cell lysate comprising the rAAV particles is at a particular pH range prior to the pH reduction step. In some embodiments, the cell lysate in a method provided herein has a pH of between 6 and 9 (e.g., 6 to 9, 6.5 to 9, 6 to 8, 6.5 to 8, or 7 to 9). In some embodiments, the cell lysate has a pH of between 6 and 8. In some embodiments, the cell lysate comprises sodium citrate (e.g., in solution). In some embodiments, the cell lysate comprises sodium phosphate (e.g., in solution). In some embodiments, the cell lysate comprises 25 mM to 1M sodium citrate (e.g., 25 mM to 1M, 25 mM to 500 mM. 25 mM to 250 mM, 25 mM to 100 mM, 50 mM to 1M, 50 mM to 500 mM. 50 mM to 250 mM, 50 mM to 100 mM, 75 mM to 1M, 75 mM to 500 mM. 75 mM to 250 mM, or 75 mM to 100 mM sodium citrate). In some embodiments, the cell lysate comprises 100 mM (millimolar) sodium citrate. In some embodiments, the cell lysate further comprises $Mg^{2+}$. In some embodiments, the $Mg^{2+}$ is present in an amount of between 0.5 mM to 2 mM (e.g., 0.5 mM to 1.5 mM, 0.8 mM to 1.2 mM, 1 mM to 2 mM, such as 0.984 mM or 1.6 mM). In some embodiments, the cell lysate further comprises an endonuclease, e.g., Benzonase® (commercially available, e.g., from SigmaAldrich and EMDMillpore). In some embodiments, the Benzonase® is present in an amount of between 100 to 300 units/gram of wet cell weight (e.g., 200 units/g wet cell weight). Wet cell weight may be determined by any method known in the art. In some embodiments, wet cell weight is determined by centrifugation of a cell suspension from harvested cells, pelleting the cells, removing the supernatant and weighing the pelleted cells.

In some embodiments of any one of the methods provided herein, the cell lysate is contacted with a composition comprising sodium citrate (such as a solution), e.g., 25 mM to 1M sodium citrate (e.g., 25 mM to 1M, 25 mM to 500 mM. 25 mM to 250 mM, 25 mM to 100 mM, 50 mM to 1M, 50 mM to 500 mM. 50 mM to 250 mM, 50 mM to 100 mM, 75 mM to 1M, 75 mM to 500 mM. 75 mM to 250 mM, or 75 mM to 100 mM sodium citrate) in order to produce the cell lysate comprising sodium citrate (e.g., in a solution). In some embodiments, the cell lysate is contacted with a composition comprising sodium phosphate (such as a solution) in order to produce the cell lysate comprising sodium phosphate (e.g., in a solution). In some embodiments, the cell lysate is contacted with $Mg^{2+}$, e.g., as $MgCl_2$, to produce the cell lysate comprising $Mg^{2+}$. In some embodiments, the cell lysate is contacted with an endonuclease, e.g., Benzonase®, in order to produce the cell lysate comprising the endonuclease. In some embodiments, the cell lysate is contacted with sodium citrate, $Mg^{2+}$, and an endonuclease to produce a cell lysate comprising sodium citrate, $Mg^{2+}$, and an endonuclease. In some embodiments, in addition to or alternatively to contacting the cell lysate with the endonuclease, the cell lysate may be spun down (e.g., by centrifugation) in order to produce a partially clarified supernatant.

In some embodiments of any one of the methods provided herein, the flocculate comprises proteins, nucleic acids and/or lipids of the cell lysate that are derived from the cells. In some embodiments, the flocculate comprises at least 90% (e.g., at least 90%, at least 91%, at least 92%, at least 93%, at least 94%, at least 95%, at least 96%, at least 97%, at least 98%, at least 99% or more) of the proteins of the cell lysate that are derived from the cells. In some embodiments, the flocculate comprises 90%-99% (e.g., 90%-99%, 91%-98%, 92%-98%, 93%-98%, 94%-98%, 95%-98%, or 95%-99%) of the proteins of the cell lysate that are derived from the cells. In some embodiments, the supernatant comprises no more than 10% (e.g., no more than 10%, no more than 9%, no more than 8%, no more than 7%, no more than 6%, no more than 5%, no more than 4%, no more than 3%, no more than 2%, no more than 1%, or less) of the proteins of the cell lysate that are derived from the cells. In some embodiments, the flocculate comprises 0.01%-10% (e.g., 0.01%-10%, 0.1%-10%, 1%-10%, 0.1%-9%, 1%-9%, 0.1%-8%, 1%-8%, 0.1%-7%, 1%-7%, 0.1%-6%, 1%-6%, 0.1%-5%, 1%-5%, 0.1%-4%, 1%-4%, 0.1%-3%, 1%-3, 0.1%-2%, 1%-2%, or 2%-5%) of the proteins of the cell lysate that are derived from the cells. The percentage of protein content of the flocculate or supernatant may be determined by any method known in the art, e.g., by Coomassie stain, silver stain, or a Bradford assay.

In some embodiments, the cell lysate is a mammalian or insect cell lysate. Exemplary mammalian cells from which the lysate may be produced include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells from which the lysate may be produced include, but are not limited to Sf9 cells (see, e.g., ATCC® CRL-1711™). The Sf9 cells may be Sf9 producer cells that comprise rep and/or cap genes from one or more AAV serotypes or pseudotypes for producing rAAV particles (see, e.g., Mietzsch et al. OneBac: platform for scalable and high-titer production of adeno-associated virus serotype 1-12 vectors for gene therapy. Hum Gene Ther. 2014 March; 25(3):212-22; and Aslanidi et al. An inducible system for highly efficient production of recombinant adeno-associated virus (rAAV) vectors in insect Sf9 cells. Proc Natl Acad Sci USA 2009 106: 5059-5064). The cell lysate may be produced using any method known in the art, e.g., by microfluidization, sonication, freeze/thawing, or hypotonic lysis of cells comprising the rAAV particles. The cells comprising the rAAV particles may be in pellet form, either frozen or thawed. In some embodiments, insect cell lysate is produced by microfluidization of insect cells comprising the rAAV particles. An exemplary microfluidization method is provided in Example 1. In some embodiments, mammalian cell lysate is produced by hypotonic lysis of mammalian cells comprising the rAAV particles.

Isolating the supernatant from the flocculate in a method described herein may be accomplished using any method known in the art, e.g., by centrifugation or filtration. In some embodiments, isolating the supernatant comprising the rAAV particles from the flocculate comprises centrifugation.

Purifying the rAAV particles from the supernatant using cation exchange chromatography in a method described herein may be accomplished using any method known in the art, e.g., sulfopropyl (SP) column chromatography or carboxymethyl (CM) chromatography (see, e.g., HiPrep™ Sp Fast Flow 16/10, HiPrep™ CM FF 16/10, and HiPrep™ SP XL 16/10 available from GE Healthcare). In some embodiments, the cation exchange chromatography comprises applying the supernatant to a column, washing with a low pH (e.g., pH between 2-5, 3-5, or 3-4) buffer (e.g., sodium citrate buffer), and eluting in a higher pH (e.g., pH 5-8, 5-7, 5-6 or 6-7) buffer (e.g., sodium citrate buffer).

In some embodiments of any one of the methods described herein, the method further comprises further purifying and/or concentrating the purified rAAV particles. The purified rAAV particles may be further purified and/or concentrated using any method known in the art, e.g., by tangential flow filtration (TFF), dialysis membrane filtration, and/or centrifugation (e.g., using centrifugation filtration devices, e.g., at 150 kD Molecular weight cut-off (MWCO) membrane filter devices, see, e.g., products from Orbital Bioscience and Millipore). Exemplary commercially available TFF systems and cartridges include products from GE Healthcare Life Sciences (see, e.g., the Midgee products) and Pall Corporation (see, e.g., Minimate™ TFF System).

The rAAV particles of the disclosure may be of any serotype or any combination of serotypes (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV2, rAAV8 or rAAV9 particles. In some embodiments, the rAAV particles are pseudotyped rAAV particles. In some embodiments the rAAV2, rAAV8 or rAAV9 particles are pseudotyped rAAV2, rAAV8 or rAAV9 particles. Pseudotyped particles are described herein. In some embodiments, the rAAV2, rAAV8 or rAAV9 particles are rAAV2/2, rAAV2/8 or rAAV2/9 pseudotyped particles. In some embodiments, the rAAV particles are rAAV8 or rAAV9 particles (e.g., rAAV2/8 or rAAV2/9 particles). In some embodiments, the rAAV particles are rAAV9 particles (e.g., rAAV2/9 particles).

In some embodiments, of a method described herein, the method may further comprise measuring the purity and/or the amount of intact rAAV particles in the purified rAAV particles. Measuring the purity and/or the amount of intact rAAV particles in the purified rAAV particles may be accomplished using any method known in the art or described herein. In some embodiments, measuring the purity and/or the amount of intact rAAV particles comprises an immunoassay, a nucleic acid hybridization-based assay (e.g., a dot-blot assay), SDS-PAGE followed by either Coomassie blue or silver staining, visualization with an electron microscope, a PCR assay, an infectious center assay (e.g., green fluorescent cell assay), or combinations thereof. In some embodiments, measuring the purity and/or the amount of intact rAAV particles comprises an immunoassay that includes antibodies specific for intact capsids (e.g., an antibody described herein or an anti-AAV2-clone A20 or anti-AAV1-clone ADK1a, both available from PROGEN Biotechnik GmbH, Catalog number 61055 and 610150, Heidelberg, Germany, or anti-AAV-8-clone ADK8 or anti-AAV9-clone ADK9, both avaiable from American Research Products, Inc. Catalog number 03-651160 and 03-651162, Waltham, Mass.), antibodies for denatured capsids (e.g., Anti-AAV, VP1/VP2/VP3 clone B1 available from American Research Products, Inc. Catalog number 03-61058, Waltham, Mass.; Wistuba A, et al. (1995), J. Virol, 69: 5311-5319), and/or antibodies specific for VP1u externalization (e.g., Anti-AAV, VP1 clone A1 available from American Research Products, Inc. Catalog number 03-61056; Wistuba, A. et al. (1997) J. of Virology 71: 1341-1352; Wobus, C E. et al. (2000) J. Virol 74 (19): 9281-9292).

Other aspects of the disclosure relate to methods of preparing rAAV particles for further purification. In some embodiments, the method comprises: (a) providing a cell lysate comprising rAAV particles and (b) reducing the pH of the cell lysate to produce a flocculate and a supernatant comprising the rAAV particles. Providing the cell lysate and reducing the pH of the cell lysate may further include any one or more of the embodiments described above. In some embodiments, the method further comprises purifying the rAAV particles. The rAAV particles may be purified by any method known in the art or described herein.

rAAV Particles and Methods of Producing rAAV Particles

Aspects of the disclosure relate to recombinant AAV (rAAV) particles and methods of purifying the rAAV particles. The purified rAAV particles have many uses, e.g., in methods and pharmaceutical compositions for treating a disease in a subject in need thereof (e.g., a subject having a disease involving reduced protein expression that may be treated with gene therapy), in rAAV particle-derived vaccines, for infecting cells to screen rAAV particles for a desired phenotype (e.g., upregulation of a protein or polypeptide of interest in the cell), or for infecting animals to screen for pharmakinetics and/or therapeutic efficacy of an rAAV.

In some embodiments, recombinant rAAV particles comprise a nucleic acid vector. In some embodiments, the nucleic acid vector contains a construct comprising (a) one or more heterologous nucleic acid regions comprising a sequence encoding a protein or polypeptide of interest or encoding an RNA of interest (e.g., a microRNA or a small hairpin RNA) and (b) one or more regions comprising inverted terminal repeat (ITR) sequences (e.g., wild-type ITR sequences or engineered ITR sequences) flanking the one or more heterologous nucleic acid regions. In some embodiments, the nucleic acid vector is encapsidated by a viral capsid. In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

Accordingly, in some embodiments, a rAAV particle comprises a viral capsid and a nucleic acid vector as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively. In some embodiments, the nucleic acid vector comprises a construct comprising (1) one or more heterologous nucleic acid regions comprising a sequence encoding a protein or polypeptide of interest, (2) one or more nucleic acid regions comprising a sequence that facilitates expression of the heterologous nucleic acid region (e.g., a promoter and/or enhancer), and (3) one or more nucleic acid regions comprising a sequence that facilitate integration of the heterologous nucleic acid region (optionally with the one or more nucleic acid regions comprising a sequence that facilitates expression) into the genome of the subject. In some embodiments, viral sequences that facilitate integration comprise Inverted Terminal Repeat (ITR) sequences. In some embodiments, the nucleic acid vector comprises one or more heterologous nucleic acid regions comprising a sequence encoding a protein or polypeptide of interest or an RNA of interest operably linked to a promoter, wherein the one or more heterologous nucleic acid regions are flanked on each side with an ITR sequence. The ITR sequences can be derived from any AAV serotype (e.g., 1, 2, 3, 4, 5, 6, 7, 8, 9, 10) or can be derived from more than one serotype. In some embodiments, the ITR sequences are derived from AAV2. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

In some embodiments, the construct (e.g., comprising one or more heterologous nucleic acid regions comprising a sequence encoding a protein or polypeptide of interest and optionally the one or more nucleic acid regions comprising a sequence that facilitates expression of the heterologous nucleic acid region) is no more than 6 kilobases, no more than 5 kilobases, no more than 4 kilobases, or no more than 3 kilobases in size. In some embodiments, the construct (e.g., comprising one or more heterologous nucleic acid regions comprising a sequence encoding a protein or polypeptide of interest and optionally the one or more nucleic acid regions comprising a sequence that facilitates expression of the heterologous nucleic acid region) is between 4 and 6 kilobases in size, e.g., 4-6 kilobases, 4-5 kilobases, or 4.2-4.7 kilobases.

In some embodiments, the nucleic acid vector comprises a pTR-UF-11 plasmid backbone, which is a plasmid that contains AAV2 ITRs, or a nucleic acid region of the pTR-UF-11 plasmid that comprises the ITRs. This plasmid is commercially available from the American Type Culture Collection (ATCC MBA-331). The sequence of pTR-UF-11 is provided in SEQ ID NO: 1.

In some embodiments, the construct comprises one or more regions comprising a sequence that facilitates expression of the heterologous nucleic acid, e.g., expression control sequences operatively linked to the heterologous nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is completed herein (e.g., a promoter and an enhancer).

To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter. For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting examples of such promoters that may be used include (1) desmin, creatine kinase, myogenin, alpha myosin heavy chain, human brain and natriuretic peptide, specific for muscle cells, and (2) albumin, alpha-1-antitrypsin, hepatitis B virus core protein promoters, specific for liver cells.

Synthetic promoters are also contemplated herein. A synthetic promoter may comprise, for example, regions of known promoters, regulatory elements, transcription factor binding sites, enhancer elements, repressor elements, and the like.

In some embodiments, a construct described herein may also contain marker or reporter genes, e.g., LacZ or a fluroscent protein.

In some embodiments, the construct comprises one or more heterologous nucleic acid regions comprising a sequence encoding a protein or polypeptide of interest. The protein or polypeptide of interest may be, e.g., a polypeptide or protein of interest provided in Table 1. The sequences of the polypeptide or protein of interest may be obtained, e.g., using the non-limiting National Center for Biotechnology Information (NCBI) Protein IDs or SEQ ID NOs from patent applications provided in Table 1.

TABLE 1

Non-limiting examples of proteins or polypeptides of interest and associated diseases

| Protein or Polypeptide | Non-limiting Exemplary diseases | Non-limiting NCBI Protein IDs or Patent SEQ ID Nos |
|---|---|---|
| acid alpha-glucosidase (GAA) | Pompe | NP_000143.2, NP_001073271.1, NP_001073272.1 |
| Methyl CpG binding protein 2 (MECP2) | Rett syndrome | NP_001104262.1, NP_004983.1 |
| Aromatic L-amino acid decarboxylase (AADC) | Parkinson's disease | NP_000781.1, NP_001076440.1, NP_001229815.1, NP_001229816.1, NP_001229817.1, NP_001229818.1, NP_001229819.1 |

TABLE 1-continued

Non-limiting examples of proteins or polypeptides of interest and associated diseases

| Protein or Polypeptide | Non-limiting Exemplary diseases | Non-limiting NCBI Protein IDs or Patent SEQ ID Nos |
|---|---|---|
| Glial cell-derived neurotrophic factor (GDNF) | Parkinson's disease | NP_000505.1, NP_001177397.1, NP_001177398.1, NP_001265027.1, NP_954701.1 |
| Cystic fibrosis transmembrane conductance regulator (CFTR) | Cystic fibrosis | NP_000483.3 |
| Tumor necrosis factor receptor fused to an antibody Fc (TNFR:Fc) | Arthritis, Rheumatoid arthritis | SEQ ID NO. 1 of WO2013025079 |
| HIV-1 gag-proΔrt (tgAAC09) | HIV infection | SEQ ID NOs. 1-5 of WO2006073496 |
| Sarcoglycan alpha, beta, gamma, delta, epsilon, or zeta (SGCA, SGCB, SGCG, SGCD, SGCE, or SGCZ) | Muscular dystrophy | SGCA NP_000014.1, NP_001129169.1 SGCB NP_000223.1 SGCG NP_000222.1 SGCD NP_000328.2, NP_001121681.1, NP_758447.1 SGCE NP_001092870.1, NP_001092871.1, NP_003910.1 SGCZ NP_631906.2 |
| Alpha-1-antitrypsin (AAT) | Hereditary emphysema or Alpha-1-antitrypsin Deficiency | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 |
| Glutamate decarboxylase 1 (GAD1) | Parkinson's disease | NP_000808.2, NP_038473.2 |
| Glutamate decarboxylase 2 (GAD2) | Parkinson's disease | NP_000809.1, NP_001127838.1 |
| Aspartoacylase (ASPA) | Canavan's disease | NP_000040.1, NP_001121557.1 |
| Nerve growth factor (NGF) | Alzheimer's disease | NP_002497.2 |
| Granulocyte-macrophage colonystimulating factory (GM-CSF) | Prostate cancer | NP_000749.2 |
| Cluster of Differentiation 86 (CD86 or B7-2) | Malignant melanoma | NP_001193853.1, NP_001193854.1, NP_008820.3, NP_787058.4, NP_795711.1 |
| Interleukin 12 (IL-12) | Malignant melanoma | NP_000873.2, NP_002178.2 |
| neuropeptide Y (NPY) | Parkinson's disease, epilepsy | NP_000896.1 |
| ATPase, Ca++ transporting, cardiac muscle, slow twitch 2 (SERCA2) | Chronic heart failure | NP_001672.1, NP_733765.1 |
| Dystrophin or Minidystrophin | Muscular dystrophy | NP_000100.2, NP_003997.1, NP_004000.1, NP_004001.1, NP_004002.2, NP_004003.1, NP_004004.1, NP_004005.1, NP_004006.1, NP_004007.1, NP_004008.1, NP_004009.1, |

TABLE 1-continued

Non-limiting examples of proteins or polypeptides of interest and associated diseases

| Protein or Polypeptide | Non-limiting Exemplary diseases | Non-limiting NCBI Protein IDs or Patent SEQ ID Nos |
|---|---|---|
| | | NP_004010.1, NP_004011.2, NP_004012.1, NP_004013.1, NP_004014.1 |
| Ceroid lipofuscinosis neuronal 2 (CLN2) | Late infantile neuronal ceroidlipofuscinosis or Batten's disease | NP_000382.3 |
| Neurturin (NRTN) | Parkinson's disease | NP_004549.1 |
| N-acetylglucosaminidase, alpha (NAGLU) | Sanfilippo syndrome (MPSIIIB) | NP_000254.2 |
| Iduronidase, alpha-1 (IDUA) | MPSI-Hurler | NP_000194.2 |
| Iduronate 2-sulfatase (IDS) | MPSII-Hunter | NP_000193.1, NP_001160022.1, NP_006114.1 |
| Glucuronidase, beta (GUSB) | MPSVII-Sly | NP_000172.2, NP_001271219.1 |
| Hexosaminidase A, α polypeptide (HEXA) | Tay-Sachs | NP_000511.2 |
| Hexosaminidase B, β polypeptide (HEXB) | Tay-Sachs | NP_000512.1, NP_001278933.1 |
| Retinal pigment epithelium-specific protein 65 kDa (RPE65) | Leber congenital amaurosis | NP_000320.1 |
| Factor IX (FIX) | Hemophilia B | NP_000124.1 |
| Adenine nucleotide translocator (ANT-1) | progressive external ophthalmoplegia | NP_001142.2 |
| ApaLI | mitochondrial heteroplasmy, myoclonic epilepsy with ragged red fibers (MERRF) or mitochondrial encephalomyopathy, lactic acidosis, and stroke-like episodes (MELAS) | YP_007161330.1 |
| NADH ubiquinone oxidoreductase subunit 4 (ND4) | Leber hereditary Optic | YP_003024035.1 |
| very long-acyl-CoA dehydrogenase (VLCAD) | very long-chain acyl-CoA dehydrogenase (VLCAD) deficiency | NP_000009.1, NP_001029031.1, NP_001257376.1, NP_001257377.1 |
| short-chain acyl-CoA dehydrogenase (SCAD) | short-chain acyl-CoA dehydrogenase (SCAD) deficiency | NP_000008.1 |
| medium-chain acyl-CoA dehydrogenase (MCAD) | medium-chain acyl-CoA dehydrogenase (MCAD) deficiency | NP_000007.1, NP_001120800.1, NP_001272971.1, NP_001272972.1, NP_001272973.1 |
| Myotubularin 1 (MTM1) | X-linked myotubular myopathy | NP_000243.1 |
| Myophosphorylase (PYGM) | McArdle disease (glycogen storage disease type V, myophosphorylase deficiency) | NP_001158188.1, NP_005600.1 |
| Lipoprotein lipase (LPL) | LPL deficiency | NP_000228.1 |
| sFLT01 (VEGF/PlGF (placental growth factor) binding domain of human VEGFR1/Flt-1 (hVEGFR1) fused to the Fc portion of human IgG(1) through a polyglycine linker) | Age-related macular degeneration | SEQ ID NO: 2, 8, 21, 23, or 25 of WO2009105669 |
| Glucocerebrosidase (GC) | Gaucher disease | NP_000148.2, NP_001005741.1, NP_001005742.1, NP_001165282.1, NP_001165283.1 |
| UDP glucuronosyltransferase 1 family, polypeptide A1 (UGT1A1) | Crigler-Najjar syndrome | NP_000454.1 |
| Glucose 6-phosphatase (G6Pase) | GSD-Ia | NP_000142.2, NP_001257326.1 |

TABLE 1-continued

Non-limiting examples of proteins or polypeptides of interest and associated diseases

| Protein or Polypeptide | Non-limiting Exemplary diseases | Non-limiting NCBI Protein IDs or Patent SEQ ID Nos |
|---|---|---|
| Ornithine carbamoyltransferase (OTC) | OTC deficiency | NP_000522.3 |
| Cystathionine-beta-synthase (CBS) | Homocystinuria | NP_000062.1, NP_001171479.1, NP_001171480.1 |
| Factor VIII (F8) | Haemophilia A | NP_000123.1, NP_063916.1 |
| Hemochromatosis (HFE) | Hemochromatosis | NP_000401.1, NP_620572.1, NP_620573.1, NP_620575.1, NP_620576.1, NP_620577.1, NP_620578.1, NP_620579.1, NP_620580.1 |
| Low density lipoprotein receptor (LDLR) | Phenylketonuria (PKU) | NP_000518.1, NP_001182727.1, NP_001182728.1, NP_001182729.1, NP_001182732.1 |
| Galactosidase, alpha (AGA) | Fabry disease | NP_000160.1 |
| Phenylalanine hydroxylase (PAH) | Hypercholesterolaemia or Phenylketonuria (PKU) | NP_000268.1 |
| Propionyl CoA carboxylase, alpha polypeptide (PCCA) | Propionic acidaemias | NP_000273.2, NP_001121164.1, NP_001171475.1 |

The polypeptides and proteins provided in Table 1 are known in the art (see, e.g., Adeno-Associated Virus Vectors in Clinical Trials. Barrie J. Carter. Human Gene Therapy. May 2005, 16(5): 541-550. doi:10.1089/hum.2005.16.541. Published in Volume: 16 Issue 5: May 25, 2005; Neuropharmacology. 2013 June; 69:82-8. doi: 10.1016/j.neuropharm.2012.03.004. Epub 2012 Mar. 17; Adeno-associated virus (AAV) gene therapy for neurological disease. Weinberg MS1, Samulski R J, McCown T J. Gene therapy for lysosomal storage disorders. Yew N S, Cheng S H. Pediatr Endocrinol Rev. 2013 November; 11 Suppl 1:99-109; Directed evolution of novel adeno-associated viruses for therapeutic gene delivery. Bartel M A, Weinstein J R, Schaffer D V. Gene Ther. 2012 June; 19(6):694-700. doi: 10.1038/gt.2012.20. Epub 2012 Mar. 8; Therapeutic in vivo gene transfer for genetic disease using AAV: progress and challenges. Mingozzi F, High K A. Nat Rev Genet. 2011 May; 12(5):341-55. doi: 10.1038/nrg2988). In some embodiments, the polypeptide or protein of interest is a human protein or polypeptide.

In some embodiments, the construct comprises one or more heterologous nucleic acid regions comprising a sequence encoding a RNA of interest (e.g., an shRNA, siRNA or microRNA) and a promoter. Exemplary RNAs of interest and AAV vectors comprising such RNAs include, e.g., AAVsh2.4, AAVsh8.2, AAVsh30.1, AAV-shHD2, shRNAs or siRNAs targeting TGFβ1, TGFβR2, and CTGF, scAAV2-IRE1alpha, XBP1 and ATF6. Such RNAs are known in the art (see, e.g., McBride et al., Artificial miRNAs mitigate shRNA-mediated toxicity in the brain: Implications for the therapeutic development of RNAi. PNAS, 2008. doi: 10.1073/pnas.0801775105; Franich et al., AAV Vector-mediated RNAi of Mutant Huntingtin Expression Is Neuroprotective in a Novel Genetic Rat Model of Huntington's Disease. Mol. Ther., 2008. doi:10.1038/mt.2008.50; Sriram et al., Triple Combination of siRNAs Targeting TGFβ1, TGFβR2, and CTGF Enhances Reduction of Collagen I and Smooth Muscle Actin in Corneal Fibroblasts. IOVS., 2013. doi: 10.1167/iovs.13-12758; and Ruan et al., Development of an anti-angiogenic therapeutic model combining scAAV2-delivered siRNAs and noninvasive photoacoustic imaging of tumor vasculature development. Cancer Letters, 2013. DOI: 10.1016/j.canlet.2012.11.016). Other exemplary RNAs of interest include RNAs (e.g., microRNAs or shRNAs) that target Huntingtin (HTT, see, e.g., NM_002111.7), Ataxin-1 (ATXN1, see, e.g., NM_000332.3 or NM_001128164.1), TGFβ1 (TGFB1, see, e.g., NM_000660.5), TGFβR2 (TGFBR2, see, e.g., NM_001024847.2 or NM_003242.5), connective tissue growth factor (CTGF, see, e.g., NM_001901.2), IRE1alpha (IRE1a, see, e.g., NM_001433.3), X-box binding protein 1 (XBP1, see, e.g., NM_001079539.1 or NM_005080.3) and activating transcription factor 6 (ATF6, see, e.g., NM_007348.3). Such RNAs of interest may be used to treat, e.g., Huntington's disease, cancer, hypervascularization, and spinocerebellar ataxia type 1.

The rAAV particle may be of any AAV serotype, including any derivative or pseudotype (e.g., 1, 2, 3, 4, 5, 6, 7, 8, 9, or 10, or pseudotypes/derivatives thereof). Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):

699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle. In some embodiments, the pseudotyped rAAV particle which comprises (a) a nucleic acid vector comprising AAV2 ITRs and (b) a capsid comprised of capsid proteins derived from AAVx (e.g., AAV1, AAV3, AAV4, AAV5, AAV6, AAV7, AAV8, AAV9, or AAV10). Exemplary rAAV pseudotyped particles include, but are not limited to rAAV2/1, rAAV2/5, rAAV2/8, and rAAV2/9 particles. Methods for producing and using pseudotyped rAAV particles are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the one or more helper plasmids is a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV2 and the cap gene is derived from AAV9. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). A sequence of exemplary helper plasmid pXX6 is provided in SEQ ID NO: 2. A sequence of exemplary helper plasmid rep2cap9 is provided in SEQ ID NO: 3.

An exemplary, non-limiting rAAV particle production method is described in Example 1. Another exemplary, non-limiting, rAAV particle production method is described next. One or more helper plasmids are produced or obtained, which comprise rep and cap ORFs for the desired AAV serotype or pseudotype (e.g., rep2cap9 plasmid) and the adenoviral VA, E2A (DBP), and E4 genes under the transcriptional control of their native promoters (e.g., pXX6 plasmid). HEK293 cells (available from ATCC®) are transfected via $CaPO_4$-mediated transfection, lipids or polymeric molecules such as Polyethylenimine (PEI) with the helper plasmid(s) and a nucleic acid vector described herein (e.g., containing a construction comprising one or more heterologous sequences that encode a protein or polypeptide of interest or an RNA of interest and ITRs flanking the heterologous sequences, e.g., a pTR-UF11 plasmid comprising one or more heterologous sequences that encode a protein or polypeptide of interest or an RNA of interest). The HEK293 cells are then incubated for at least 60 hours to allow for rAAV particle production. Alternatively, in another example Sf9-based producer stable cell lines are infected with a single recombinant baculovirus containing the rAAV expression cassette. As a further alternative, in another example HEK293 or BHK cell lines are infected with a HSV containing the rAAV expression cassette and optionally one or more helper HSVs containing rep and cap ORFs for the desired AAV serotype or pseudotype and the adenoviral VA, E2A (DBP), and E4 genes under the transcriptional control of their native promoters. The Sf9 cells are then incubated for at least 60 hours to allow for rAAV particle production. The rAAV particles can then be purified from the HEK293 or SF9 cells using a method described herein.

Other methods for obtaining, producing, making and using rAAV particles are known in the art and discussed herein (see, e.g., Kessler et al. (1996). Gene delivery to skeletal muscle results in sustained expression and systemic delivery of a therapeutic protein. Proceedings of the National Academy of Sciences of the United States of America 93: 14082-14087; Pauly et al. (1998). Complete correction of acid alpha-glucosidase deficiency in Pompe disease fibroblasts in vitro, and lysosomally targeted expression in neonatal rat cardiac and skeletal muscle. Gene therapy 5: 473-480; Song et al. (1998). Sustained secretion of human alpha-1-antitrypsin from murine muscle transduced with adeno-associated virus vectors. Proceedings of the National Academy of Sciences of the United States of America 95: 14384-14388; Conway et al. (1999). High-titer recombinant adeno-associated virus production utilizing a recombinant herpes simplex virus type I vector expressing AAV-2 Rep and Cap. Gene therapy 6: 986-993; Xu et al. (2001). CMV-beta-actin promoter directs higher expression from an adeno-associated viral vector in the liver than the cytomegalovirus or elongation factor 1 alpha promoter and results in therapeutic levels of human factor X in mice. Human gene therapy 12: 563-573; Asfour et al. (2002). Uniform long-term gene expression using adeno-associated virus (AAV) by ex vivo recirculation in rat-cardiac isografts. The Thoracic and cardiovascular surgeon 50: 347-350; Fraites et al. (2002). Correction of the enzymatic and functional deficits in a model of Pompe disease using adeno-associated virus vectors. Molecular therapy: the journal of the American Society of Gene Therapy 5: 571-578; Mah et al. (2002). Virus-based gene delivery systems. Clinical pharmacokinetics 41: 901-911; Mah et al. (2002). Improved method of recombinant AAV2 delivery for systemic targeted gene therapy. Molecular therapy: the journal of the American Society of Gene Therapy 6: 106-112; Sun et al. (2002). Sustained hepatic and renal glucose-6-phosphatase expression corrects glycogen storage disease type Ia in mice. Human molecular genetics 11: 2155-2164; Zolotukhin et al. (2002). Production and purification of serotype 1, 2, and 5 recombinant adeno-associated viral vectors.

Methods 28: 158-167; Mah et al. (2003). Dual vectors expressing murine factor VIII result in sustained correction of hemophilia A mice. Human gene therapy 14: 143-152; Flotte et al. (2004). Phase I trial of intramuscular injection of a recombinant adeno-associated virus alpha 1-antitrypsin (rAAV2-CB-hAAT) gene vector to AAT-deficient adults. Human gene therapy 15: 93-128; Mah et al. (2004). A new method for recombinant adeno-associated virus vector delivery to murine diaphragm. Molecular therapy: the journal of the American Society of Gene Therapy 9: 458-463; Rucker et al. (2004). Rescue of enzyme deficiency in embryonic diaphragm in a mouse model of metabolic myopathy: Pompe disease. Development 131: 3007-3019; Cresawn et al. (2005). Impact of humoral immune response on distribution and efficacy of recombinant adeno-associated virus-derived acid alpha-glucosidase in a model of glycogen storage disease type II. Human gene therapy 16: 68-80; Kohlbrenner et al. (2005). Successful production of pseudotyped rAAV particles using a modified baculovirus expression system. Molecular therapy: the journal of the American Society of Gene Therapy 12: 1217-1225; Mah et al. (2005). Sustained correction of glycogen storage disease type II using adeno-associated virus serotype 1 vectors. Gene therapy 12: 1405-1409; Walker et al. (2005). Expression of erythropoietin in cats treated with a recombinant adeno-associated viral vector. American journal of veterinary research 66: 450-456; Brantly et al. (2006). Phase I trial of intramuscular injection of a recombinant adeno-associated virus serotype 2 alphal-antitrypsin (AAT) vector in AAT-deficient adults. Human gene therapy 17: 1177-1186; Ghosh et al. (2006). Long-term correction of murine glycogen storage disease type Ia by recombinant adeno-associated virus-1-mediated gene transfer. Gene therapy 13: 321-329; Kishnani et al. (2006). Pompe disease diagnosis and management guideline. Genetics in medicine: official journal of the American College of Medical Genetics 8: 267-288; Pacak et al. (2006). Recombinant adeno-associated virus serotype 9 leads to preferential cardiac transduction in vivo. Circ Res 99: e3-9; Flotteet al. (2007). Preclinical characterization of a recombinant adeno-associated virus type 1-pseudotyped vector demonstrates dose-dependent injection site inflammation and dissemination of vector genomes to distant sites. Human gene therapy 18: 245-256; Mah et al. (2007). Physiological correction of Pompe disease by systemic delivery of adeno-associated virus serotype 1 vectors. Molecular therapy: the journal of the American Society of Gene Therapy 15: 501-507; Pacak et al. (2007). Long-term skeletal muscle protection after gene transfer in a mouse model of LGMD-2D. Molecular therapy: the journal of the American Society of Gene Therapy 15: 1775-1781; Cideciyan et al. (2008). Human gene therapy for RPE65 isomerase deficiency activates the retinoid cycle of vision but with slow rod kinetics. Proceedings of the National Academy of Sciences of the United States of America 105: 15112-15117; Flotte et al. (2008). Apparently nonspecific enzyme elevations after portal vein delivery of recombinant adeno-associated virus serotype 2 vector in hepatitis C virus-infected chimpanzees. Human gene therapy 19: 681-689; Hauswirth et al. (2008). Treatment of leber congenital amaurosis due to RPE65 mutations by ocular subretinal injection of adeno-associated virus gene vector: short-term results of a phase I trial. Human gene therapy 19: 979-990; Pacak et al. (2008). Relative persistence of AAV serotype 1 vector genomes in dystrophic muscle. Genetic vaccines and therapy 6: 14; Pacak et al. (2008). Tissue specific promoters improve specificity of AAV9 mediated transgene expression following intra-vascular gene delivery in neonatal mice. Genetic vaccines and therapy 6: 13; Polyak et al. (2008). Gene delivery to intestinal epithelial cells in vitro and in vivo with recombinant adeno-associated virus types 1, 2 and 5. Digestive diseases and sciences 53: 1261-1270; Brantly et al. (2009). Sustained transgene expression despite T lymphocyte responses in a clinical trial of rAAV1-AAT gene therapy. Proceedings of the National Academy of Sciences of the United States of America 106: 16363-16368; Byrne, B J (2009). Innovative vector design: cross-packaged, self-complementary and now trans-splicing AAV vectors. Human gene therapy 20: 1224-1225; Cideciyan et al. (2009). Human RPE65 gene therapy for Leber congenital amaurosis: persistence of early visual improvements and safety at 1 year. Human gene therapy 20: 999-1004; Cideciyan et al. (2009). Vision 1 year after gene therapy for Leber's congenital amaurosis. The New England journal of medicine 361: 725-727; Clement et al. (2009). Large-scale adeno-associated viral vector production using a herpesvirus-based system enables manufacturing for clinical studies. Human gene therapy 20: 796-806; Mendell et al. (2009). Limb-girdle muscular dystrophy type 2D gene therapy restores alpha-sarcoglycan and associated proteins. Annals of neurology 66: 290-297; Lock et al. (2010). Characterization of a recombinant adeno-associated virus type 2 Reference Standard Material. Human gene therapy 21: 1273-1285; Mah et al. (2010). Gel-mediated delivery of AAV1 vectors corrects ventilatory function in Pompe mice with established disease. Molecular therapy: the journal of the American Society of Gene Therapy 18: 502-510; Mendell et al. (2010). Sustained alpha-sarcoglycan gene expression after gene transfer in limb-girdle muscular dystrophy, type 2D. Annals of neurology 68: 629-638; Weinstein et al. (2010). Adeno-associated virus-mediated correction of a canine model of glycogen storage disease type Ia. Human gene therapy 21: 903-910; Byrne et al. (2011). Pompe disease gene therapy. Human molecular genetics 20: R61-68; Mandel et al. (2011). AAV6-mediated gene silencing fALS short. Molecular therapy: the journal of the American Society of Gene Therapy 19: 231-233; Pacak et al. (2011). AAV vectors for cardiac gene transfer: experimental tools and clinical opportunities. Molecular therapy: the journal of the American Society of Gene Therapy 19: 1582-1590; Byrne et al. (2012). Gene therapy approaches for lysosomal storage disease: next-generation treatment. Human gene therapy 23: 808-815; ElMallah et al. (2012). Retrograde gene delivery to hypoglossal motoneurons using adeno-associated virus serotype 9. Human gene therapy methods 23: 148-156; Jacobson et al. (2012). Gene therapy for leber congenital amaurosis caused by RPE65 mutations: safety and efficacy in 15 children and adults followed up to 3 years. Archives of ophthalmology 130: 9-24; Lee et al. (2012). An acidic oligopeptide displayed on AAV2 improves axial muscle tropism after systemic delivery. Genetic vaccines and therapy 10: 3; Qiu et al. (2012). Spinal Delivery of AAV Vector Restores Enzyme Activity and Increases Ventilation in Pompe Mice. Molecular therapy: the journal of the American Society of Gene Therapy 20: 21-27; Stedman et al. (2012). Signs of progress in gene therapy for muscular dystrophy also warrant caution. Molecular therapy: the journal of the American Society of Gene Therapy 20: 249-251; Conlon et al. (2013). Preclinical toxicology and biodistribution studies of recombinant adeno-associated virus 1 human acid alpha-glucosidase. Human gene therapy Clinical development 24: 127-133; Elmallah et al. (2013). Sustained Correction of Motoneuron Histopathology Following Intramuscular Delivery of AAV in Pompe Mice. Molecular therapy: the journal of the American Society of Gene Therapy; Falk et al. (2013). Intrapleural administration of AAV9 improves neural and cardiorespiratory function in Pompe disease. Molecular therapy: the journal of the American Society of Gene Therapy 21: 1661-1667; Lee et al. (2013). Treatment of congenital neurotransmitter deficiencies by intracerebral ventricular injection of an AAV9 vector. Human gene therapy; Mah et al. (2013). Adeno-associated virus-mediated gene therapy for metabolic myopathy. Human gene therapy 24: 928-936; Smith et al. (2013). Phase I/II trial of adeno-associated virus-mediated alpha-glucosidase gene therapy to the diaphragm for chronic respiratory failure in Pompe disease: initial safety and ventilatory outcomes. Human gene therapy 24: 630-640, all of which are incorporated by reference with respect to the disclosure related to obtaining, producing, making, and using rAAV particles).

Compositions

Aspects of the disclosure relate to compositions comprising rAAV particles or further purified and/or concentrated rAAV particles described herein. In some embodiments, the composition is obtainable by or produced by a method described herein.

In some embodiments, purified rAAV particles or further purified and/or concentrated rAAV particles described herein are added to a composition, e.g., a pharmaceutical composition. In some embodiments, the composition comprising rAAV particles has a purity of above 90%, above 91%, above 92%, above 93%, above 94%, above 95%, above 96%, above 97%, above 98%, above 99%, above 99.1%, above 99.2%, above 99.3%, above 99.4%, above 99.5%, above 99.6%, above 99.7%, above 99.8%, above 99.9% or above 99.99%. Purity may be measured using any method known in the art. In some embodiments, purity is measured by determining the amount of capsid proteins, VP1, VP2, and VP3 (which are approximately 87, 72, and 63 kiloDaltons (kD) in size, depending on the serotype) relative to the total protein amount present in the purified rAAV particles or further purified and/or concentrated rAAV particles (e.g., in a pharmaceutical composition). In some embodiments, the amount of capsid proteins is measured using SDS-PAGE followed by a gel stain such as Silver stain or Coomassie Blue stain (e.g., GelCode® Blue reagent from ThermoScientific). The stain may be quantified, e.g., by densitometry or any other method known in the art. In some embodiments, the capsids proteins are present in an amount of at least 90% of the total protein amount (e.g., at least 90% of all bands present in an SDS-PAGE gel as detected by Silver stain or Coomassie stain are capsid protein bands such as at 87, 72, and 63 kiloDaltons). In some embodiments, one or more positive controls are used in a purity measurement or assay, e.g., compositions comprising a known rAAV serotype, optionally at a known concentration.

In some embodiments, the composition comprises a pharmaceutically acceptable carrier. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), pH adjusting agents (such as inorganic and organic acids and bases), sweetening agents, and flavoring agents.

In some embodiments, a composition described herein may be administered to a subject in need thereof. In some embodiments, a method described herein may further comprise administering a composition comprising rAAV particles as described herein to a subject in need thereof. In some embodiments, the subject is a human subject.

In some embodiments, the subject has or is suspected of having a disease that may be treated with gene therapy. Exemplary diseases include, but are not limited to, cystic fibrosis, hemophilia B, San Filippo syndrome, lipoprotein lipase deficiency, alpha-1 antitrypsin deficiency, arthritis, hereditary emphysema, Leber's congenital amaurosis, age-related macular degeneration, muscular dystrophy (duchenne, LGMD2d and 2c), Parkinson's disease, Canavan's disease, Batten's disease, Alzheimer's disease, metachromatic leukodystrophy, alpha-1 antitrypsin deficiency, lipoprotein lipase deficiency, heart failure, rheumatoid arthritis, amyotrophic lateral sclerosis (ALS), spinal muscular atrophy (SMA), ornithine transcarbamylase deficiency, epilepsy, Rett syndrome, lysosomal storage disorders of skeletal muscle or CNS or Pompe disease, or another disease listed in Table 1. These diseases, associated symptoms and signs of the diseases, and methods of diagnosis of the diseases are known in the art and available to the skilled practitioner. Treatment methods involving rAAV particles are also known in the art (see, e.g., Adeno-Associated Virus Vectors in Clinical Trials. Barrie J. Carter. Human Gene Therapy. May 2005, 16(5): 541-550. doi:10.1089/hum.2005.16.541. Published in Volume: 16 Issue 5: May 25, 2005; Neuropharmacology. 2013 June; 69:82-8. doi: 10.1016/j.neuropharm.2012.03.004. Epub 2012 Mar. 17; Adeno-associated virus (AAV) gene therapy for neurological disease. Weinberg MS1, Samulski R J, McCown T J. Gene therapy for lysosomal storage disorders. Yew N S, Cheng S H. Pediatr Endocrinol Rev. 2013 November; 11 Suppl 1:99-109; Directed evolution of novel adeno-associated viruses for therapeutic gene delivery. Bartel M A, Weinstein J R, Schaffer D V. Gene Ther. 2012 June; 19(6):694-700. doi: 10.1038/gt.2012.20. Epub 2012 Mar. 8; Therapeutic in vivo gene transfer for genetic disease using AAV: progress and challenges. Mingozzi F, High K A. Nat Rev Genet. 2011 May; 12(5):341-55. doi: 10.1038/nrg2988).

The compositions described above may be administered to a subject in any suitable formulation by any suitable method. The route of administration of the composition may be oral, parenteral, by inhalation or topical. The term parenteral as used herein includes intravenous, intraarterial, intraperitoneal, intramuscular, intradermal, intrathoracic, intrathecal, and subcutaneous administration. The compositions described above are typically administered to a subject in an effective amount, that is, an amount capable of producing a desirable result. The desirable result will depend upon the active agent being administered. For example, an effective amount of rAAV particles may be an amount of the particles that are capable of transferring a heterologous nucleic acid to a host organ, tissue, or cell. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

In some embodiments, compositions comprising rAAV particles may be directly introduced into a subject, including by intravenous (IV) injection, intraperitoneal (IP) injection, or in situ injection into target tissue (e.g., muscle). For example, a syringe and needle can be used to inject a rAAV particle composition into a subject. Depending on the desired route of administration, injection can be in situ (i.e., to a particular tissue or location on a tissue), intramuscular, IV, IP, or by another parenteral route. Parenteral administration of rAAV particles by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the rAAV particles may be in powder form (e.g., lyophilized) for constitution with a suitable vehicle, for example, sterile pyrogen-free water, before use.

To facilitate delivery of the rAAV particles to a subject, the rAAV particles can be mixed with a carrier or excipient. Carriers and excipients that might be used include saline (e.g., sterilized, pyrogen-free saline) saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects. Methods for making such formulations are well known and can be found in, for example, Remington: The Science and Practice of Pharmacy, $22^{nd}$ edition, Pharmaceutical Press, 2012.

In addition to the formulations described previously, the rAAV particles can also be formulated as a depot preparation. Such long acting formulations may be administered by implantation (for example subcutaneously or intramuscularly) or by intramuscular (IM) injection. Thus, for example, the rAAV particles may be formulated with suitable polymeric or hydrophobic materials (for example as an emulsion in an acceptable oil) or ion exchange resins, or as sparingly soluble derivatives.

Kits

Aspects of the disclosure relate to kits, e.g., a kit for performing a method described herein. In some embodiments, the kit comprises water for injection (WFI), sodium citrate and citric acid. In some embodiments, the sodium citrate and citric acid are in a solution (e.g., at molarity described herein), either together (e.g., as a buffer) or separately.

In some embodiments, the citric acid is provided in a solution at a pH of less than or equal to 5 (e.g., less than 4, less or equal to than 3.5, less than or equal to 3, less than or equal to 2.5, or less than or equal to 2). In some embodiments, the citric acid is provided in a solution at a pH of between 2 and 5 (e.g., 2 to 5, 2 to 4.5, 2 to 4, 2 to 3, 2.5 to 5, 2.5 to 4, 3 to 5, 3 to 4, 3.5 to 5, 3.5 to 4, or 4 to 5). In some embodiments, the sodium citrate is provided in a solution at a pH of between 6 and 9 (e.g., 6 to 9, 6.5 to 9, 6 to 8, 6.5 to 8, or 7 to 9).

In some embodiments, the kit comprises a 10 mM-1M citric acid solution (e.g., 10 mM-1M, 10 mM-750 mM, 10 mM-500 mM, 10 mM-250 mM, 10 mM-100 mM, 25 mM-1M, 25 mM-750 mM, 25 mM-500 mM, 25 mM-250 mM, 25 mM-100 mM, 50 mM-1M, 50 mM-750 mM, 50 mM-500 mM, 50 mM-250 mM, 50 mM-100 mM, 75 mM-1M, 75 mM-750 mM, 75 mM-500 mM, 75 mM-250 mM, or 75 mM-100 mM) and a 10 mM-1M mM sodium citrate solution (e.g., 10 mM-1M, 10 mM-750 mM, 10 mM-500 mM, 10 mM-250 mM, 10 mM-100 mM, 25 mM-1M, 25 mM-750 mM, 25 mM-500 mM, 25 mM-250 mM, 25 mM-100 mM, 50 mM-1M, 50 mM-750 mM, 50 mM-500 mM, 50 mM-250 mM, 50 mM-100 mM, 75 mM-1M, 75 mM-750 mM, 75 mM-500 mM, 75 mM-250 mM, or 75 mM-100 mM). In some embodiments, the kit comprises 100 mM sodium citrate solution and 100 mM citric acid solution.

In some embodiments, the kit comprises water for injection (WFI), sodium citrate (e.g., 100 mM sodium citrate), citric acid (e.g., 100 mM citric acid), and a sulfopropyl (SP) resin chromatography column (e.g., a 1 ml SP FF HiTrap from GE Healthcare Life Sciences). In some embodiments, the kit comprises water for injection (WFI), sodium citrate (e.g., 100 mM sodium citrate), citric acid (e.g., 100 mM citric acid), and a sulfopropyl (SP) resin chromatography column (e.g., a 1 ml SP FF HiTrap from GE Healthcare Life Sciences) and a filtration concentrator, such as an ultrafiltration concentrator (e.g., an Apollo® 150 from Orbital Bioscience).

In some embodiments, the kit comprises sodium citrate (e.g., 100 mM sodium citrate), citric acid (e.g., 25 mM to 1M citric acid, such as 100 mM citric acid), and a sulfopropyl (SP) resin chromatography column (e.g., a 1 ml SP FF HiTrap from GE Healthcare Life Sciences). In some embodiments, the kit comprises sodium citrate (e.g., 100 mM sodium citrate), citric acid (e.g., 100 mM citric acid), and a sulfopropyl (SP) resin chromatography column (e.g., a 1 ml SP FF HiTrap from GE Healthcare Life Sciences) and a filtration concentrator, such as an ultrafiltration concentrator (e.g., an Apollo® 150 from Orbital Bioscience).

In some embodiments, the kit further comprises instructions for use, e.g., instructions for use in a method described herein. In some embodiments, the kit further comprises one or more tubes or other types of containers for cell lysate (e.g., Eppendorf tubes) and/or one or more tubes or other types of containers for waste generated (e.g., 10 mL or 50 mL tubes for collecting flow-through and other wastes that could be produced in a method described herein).

WFI is sterile, nonpyrogenic, distilled water suitable for injection. In some embodiments, WFI is produced by distillation (or optionally by a purification process proven to be equal to or superior to distillation) and has the following properties: conductivity of no greater than 1.3 uS/cm at 25 degrees Celsius (or an equivalent at another temperature), a total organic carbon (TOC) level of less than or equal to 500 parts per billion, a bacteria endotoxin level below 0.25 endotoxin units per milliliter (EU/mL), and a bacterial level of no more than 10 colony-forming units (CFU) per 100 mL. WFI is known in the art and can be produced using routine methods.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Exemplary AAV Purification Protocol

Described below and elsewhere herein is a rapid, low cost, and scalable method for purification of various rAAVs from the lysates of producer cells of either mammalian or insect origin. The method takes advantage of two general biochemical properties of all characterized AAV serotypes:

1) low isoelectric point of a capsid; and 2) relative biological stability of the viral particle in the acidic environment. A simple and rapid clarification of cell lysate to remove the bulk of proteins and DNA is accomplished by utilizing inexpensive off-the-shelf reagents such as sodium citrate and citric acid. After the low-speed centrifugation step, the supernatant is subjected to cation exchange chromatography via SP column. The eluted virus may then be further concentrated by either centrifugal spin devices or tangential flow filtration yielding material of high titer and GMP grade biochemical purity. The protocol was validated for rAAV serotypes 2, 8, and 9. The described method makes rAAV vector technology readily available for the low budget research laboratories and could be easily adapted for a large scale GMP production format.

Recombinant adeno-associated virus (rAAV) vectors have emerged as one of the most versatile and successful gene therapy delivery vehicles. A number of recent clinical trials had impressive clinical outcomes [refs. 1-6] and patients diagnosed with lipoprotein lipase deficiency will now have an option to be treated with Glybera®, the first rAAV-based drug to win the regulatory approval of the European Medicines Agency (EMA). However, even though the industry is poised for the expansion into several application areas represented by orphan diseases, a simple and scalable rAAV production technology is still lacking. The ever growing rAAV vector toolbox, in addition to many natural AAV serotypes, now includes numerous AAV capsid mutants derived from combinatorial libraries or through rational engineering [refs. 5, 7]. To purify all these divergent AAV variants, buoyant density gradients such as CsCl, or iso-osmotic medium iodixanol discontinuous gradients [ref. 8] are routinely used. Although quite useful in a laboratory setting, these procedures are neither scalable nor easily adapted for Good Manufacturing Practice (GMP) protocols. In this regard, the more promising approach incorporates chromatography steps, either affinity, hydrophobic, or ion-exchange, depending on the biochemical properties of a particular serotype. For example, heparin affinity chromatography based on interaction with heparan sulfate proteoglycan has been successfully applied to rAAV2 [refs. 8, 9], while mucin affinity chromatography can be used for rAAV5 purification because it binds to sialic acid [ref. 10]. Many successful examples of one- or two-step ion-exchange chromatography purification have been reported for rAAV serotypes 1, 2, 4, 5, and 8 [refs. 11-15]. More recently, an affinity media incorporating an anti-AAV $V_HH$ ligand, a single-domain camelid antibody derivative, was utilized to purify serotypes 1, 2, 3, and 5 [ref. 16]. In spite of these documented successful examples, some AAV serotypes, such as rAAV9, are refractory to conventional chromatography procedures and require significant effort and exceptional laboratory skills for their purification [ref. 17].

Described herein is an efficient and reproducible protocol based on a partial purification of the initial crude lysate by flocculation of cell debris under low pH conditions, followed by one-step cation-exchange chromatography. The flocculation step eliminates the bulk of the contaminating protein and DNA allowing for quantitative AAV binding to, and subsequent elution from the resin. The method could be applied to several serotypes and for vectors purified from both mammalian and insect cell production systems.

Testing Vector Infectivity and Stability Over pH Range.

Figure 2A:
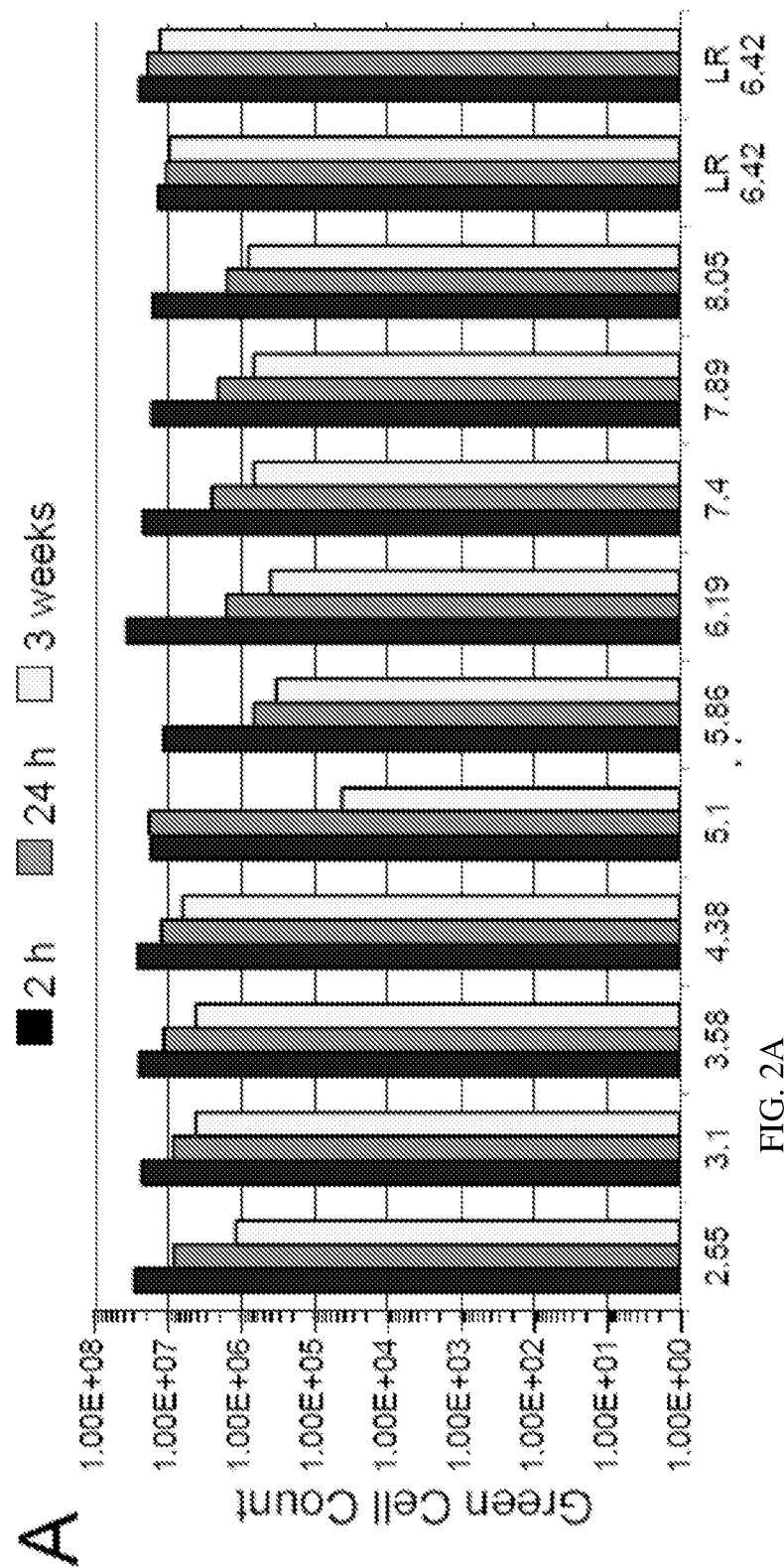
FIGS. 2A and 2B are a graph and a series of photographs showing exemplary results of rAAV9 stability testing. 2A—Infectious titer assay: iodixanol-purified rAAV9-GFP was exposed to sodium citrate/phosphate buffers in the range of pH2.55-8.05, at room temperature for the time period of 2 h, 24 h, or 3 weeks. After incubation, an aliquot was diluted in Lactate Ringer solution and used to infect C12 cells co-infected with Ad5 (multiplicity of infection (MOI) of 5). GFP (+) cells were visually scored at 48 h post infection. 2B—EM studies: viral capsid were visualized after treatment at different temperatures (rows) in buffers of different pHs (columns).

AAV9 was selected for the development of all the experimental steps since AAV9 is one of the most challenging AAV serotypes to purify. It has been observed previously that the unique N-terminus of the AAV capsid viral protein VP1 (VP1u) undergoes a reversible pH-induced unfolding/refolding process, complemented by a loss/gain of α-helical structure which does not disrupt the capsid integrity [ref. 18]. To test whether these pH-induced structural changes affect vector infectivity, we exposed rAAV9 vector to citrate and phosphate buffers with pH ranging from pH2.5 to pH8 for periods of time of up to three weeks followed by an infectivity assay. A physiological solution, Lactated Ringer (LR, pH6.42) was used as a positive control buffer. The in vitro infectivity of the rAAV-GFP was assayed before and after pH exposure for a specified period of time. As shown in FIG. 2A, after a short 2 h exposure, the infectivity of the virus does not change in any of the buffers over the whole pH range tested. After 24 h incubation, however, there was a ten-fold reduction in infectivity which was more pronounced at the range of pH5-6, followed by another log reduction after exposure for three weeks. Surprisingly, however, the lower pH range was less deleterious thus providing experimental validation for the low pH-induced flocculation step. Obviously, other components of the buffer provide structural stability as well because LR appears to better sustain higher virus infectivity over three weeks, the period of time tested.

Figure 6:
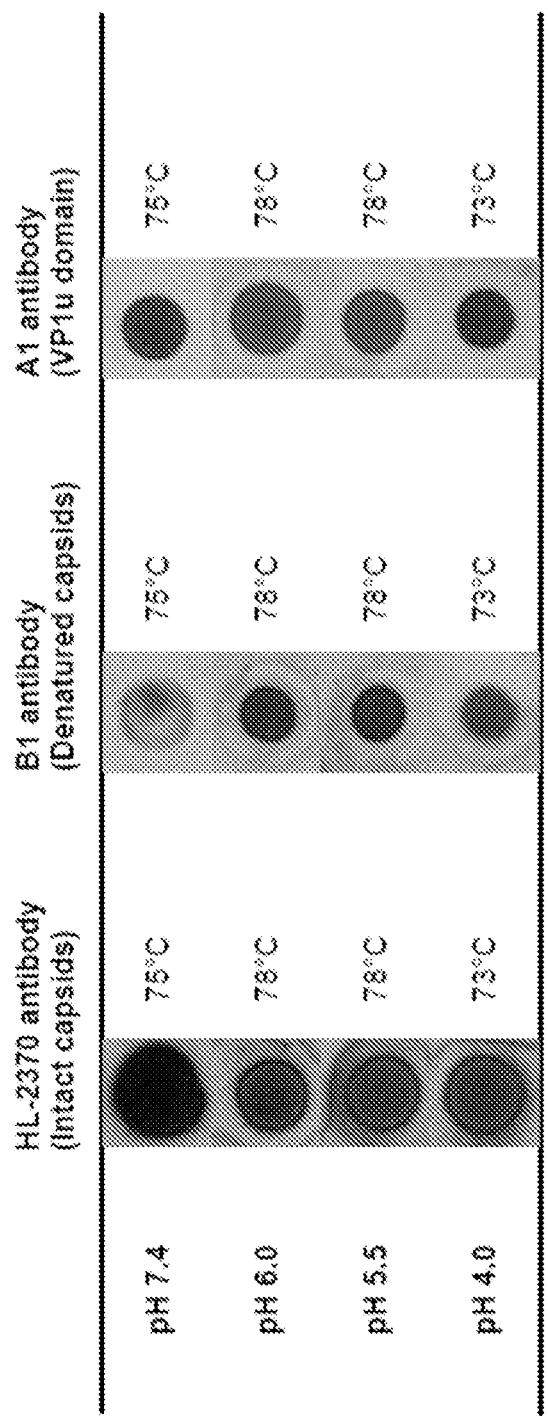
FIG. 6 is a series of photographs of dotblots within a table showing the last temperature at which intact capsids were detected (HL-2370) and the first temperature at which denatured particles were detected (B1 and A1).

Independently, the impact of pH on the structural stability of rAAV9-GFP was tested by a dot-blot immunoassay. Iodixanol-purified rAAV9-GFP, in citrate-phosphate buffer at pH 7.4, 6.0, 5.5, or 4.0, was exposed to the range of temperatures 4-100° C. and blotted for antibodies to detect intact capsids (HL-2370), denatured capsids (B1), and VP1u externalization (A1) (data not shown). Based on the observations, the temperature range was narrowed to 70-80° C. to more accurately determine capsid stability and denaturation temperature. FIG. 6 lists the last temperature at which intact capsids were detected (HL-2370) and the first temperature at which denatured capsids were detected (B1 and A1). At neutral pH (pH 7.4) the capsid was intact at 75° C. but not 78° C. Low pH (pH 4.0) induced a loss in capsid stability since particles were only intact to 73° C. However, intermediate acidity (pH 5.5-6.0) increased the stability of the capsid to 78° C. Interestingly, there appeared to be a reverse correlation between increased capsid stability in the pH 5.5-6.0 range and the reduced infectivity (FIG. 2A) in the same pH range which may be due to slower uncoating of the capsid within a cell.

Figure 2B:
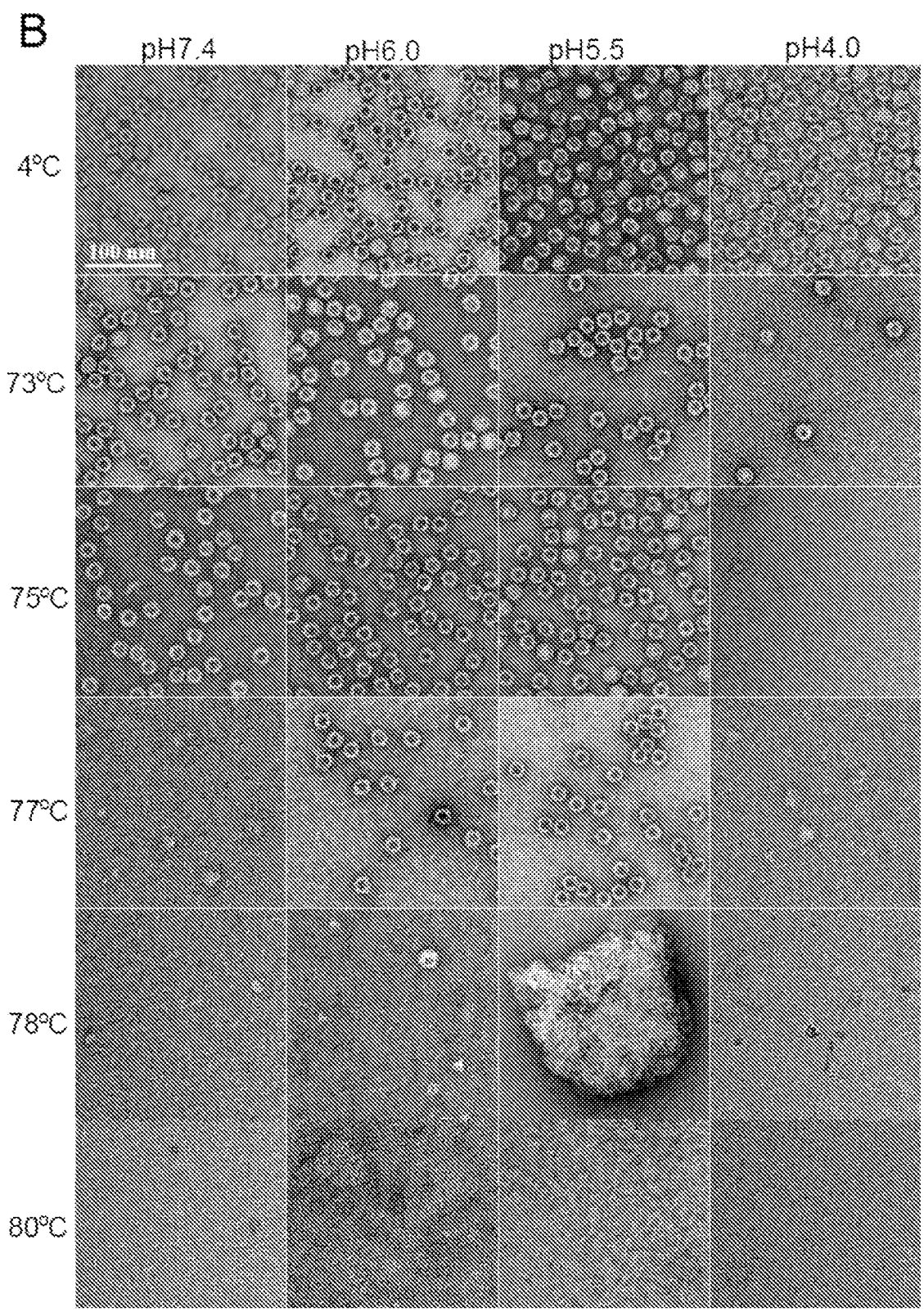

The structural stability of the rAAV9-GFP virus was further validated using electron microscopy. As with the dot-blot assay, capsids in citrate-phosphate buffer at pH 7.4, 6.0, 5.5, or 4.0 were exposed to temperatures between 70-80° C. and visualized using negative-stain EM (FIG. 2B). Intact capsids were detected up to 73° C. for pH 4.0, 75° C. for pH 7.4, and 78° C. for pH 5.5 and 6.0. However, above these respective temperatures the capsids were denatured and no longer visible. Additionally, for capsids at pH 6.0, while stable at 77° C., when heated to 78° C. there was a decrease in the number of intact particles visible and an increase in broken particles indicating the capsids are not stable and are denaturing at this point. These EM results agree with the dot-blot data and together these observations demonstrate a very sharp transition temperature in capsid stability, which is otherwise very high for the rAAV9-GFP capsids.

SP Column Chromatography

AAV9.

Figure 3A:
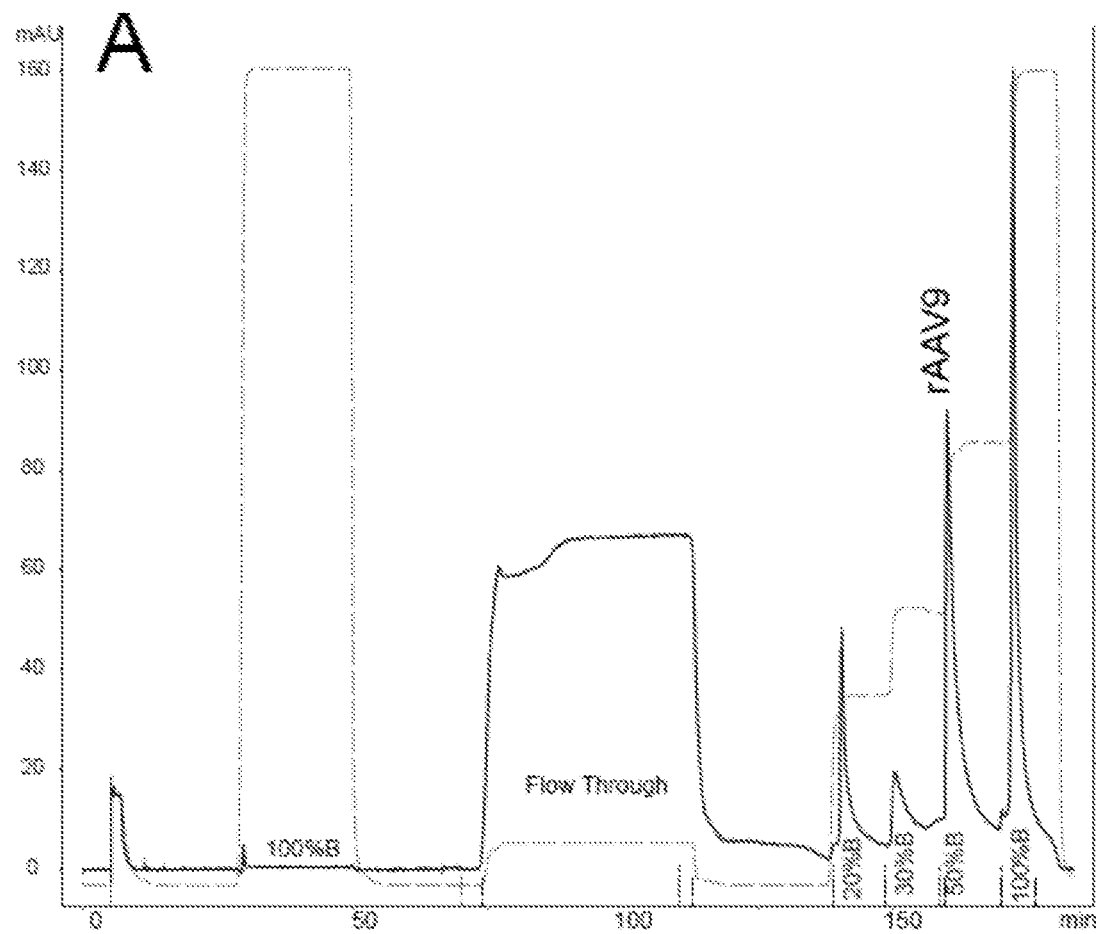
FIGS. 3A-F are a series of graphs and photographs showing an exemplary rAAV9 purification.
Figures 3B, 3C:
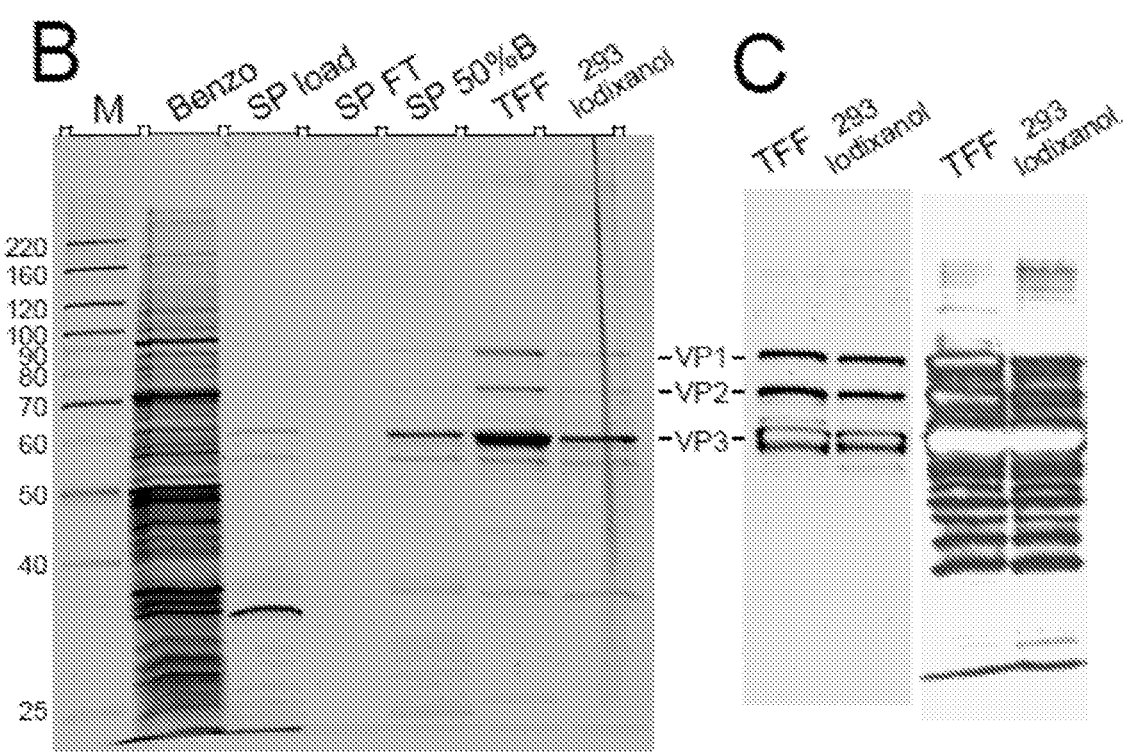
Figure 3D:
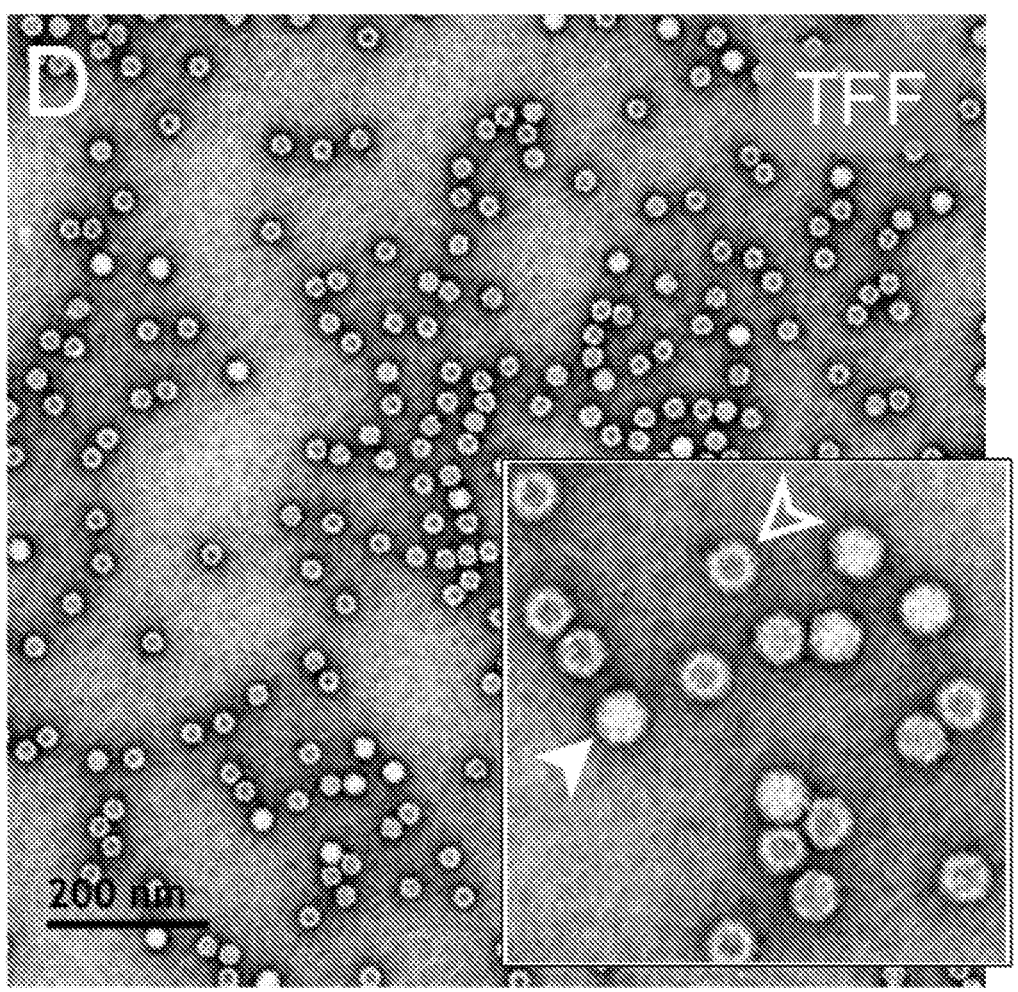
Figure 3E:
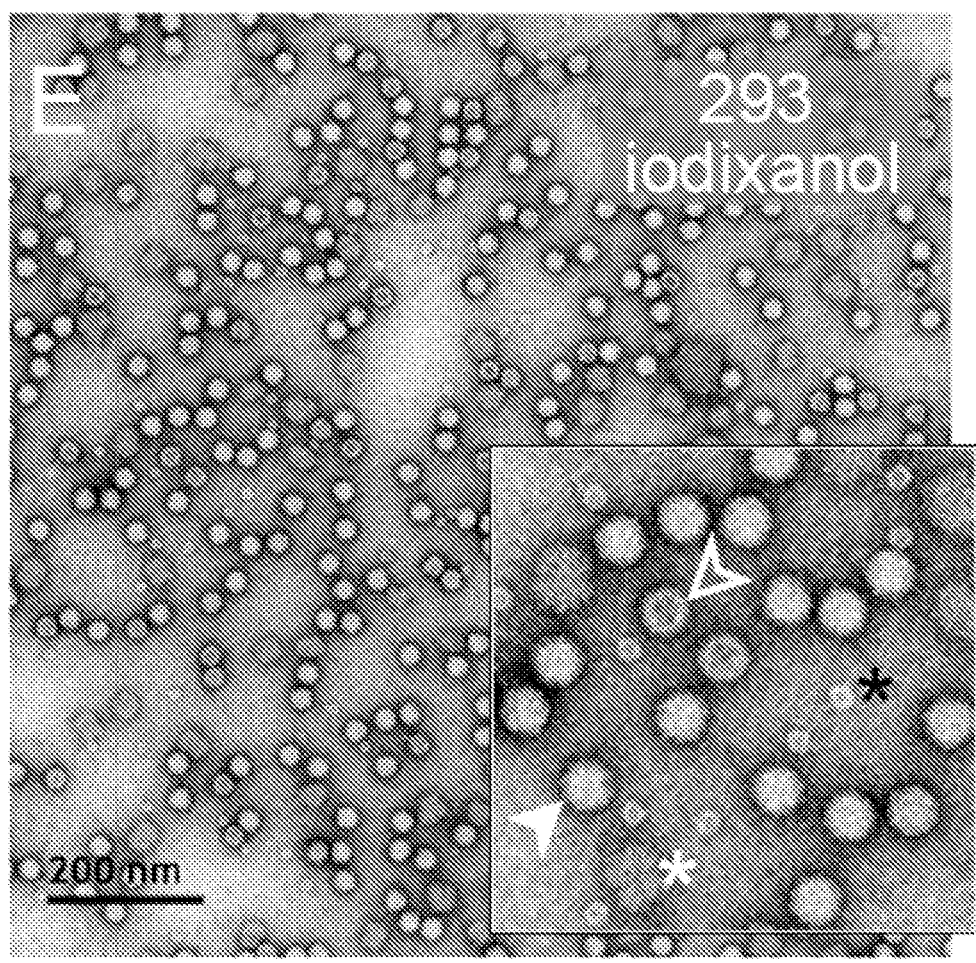
Figure 3F:
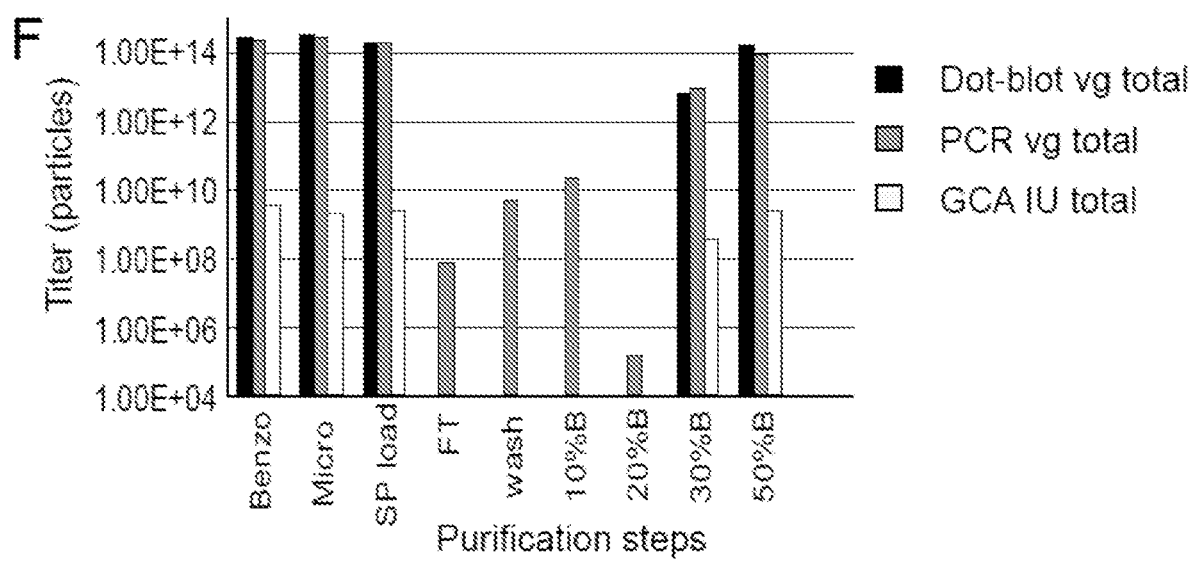

AAV9-based vectors exhibit distinctive properties such as delayed blood clearance, ability to cross blood-brain barrier, and targeting cardiac muscle with a higher tropism. This serotype, however, proved to be challenging to purify using standard chromatography procedures. Followed flocculation step, it was tested as to whether AAV9 remaining in the supernatant was capable of binding to an ion-exchange resin (FIG. 3A). AKTA FPLC (GE Health Care) system had been utilized. After the microfluidization step, the crude lysate contained 1288 mg of protein, the amount of which was reduced down to 14.8 mg of total protein in the supernatant fraction applied to the column. Thus, low pH flocculation followed by low-speed centrifugation disposes of 98.85% of total protein in the crude lysate making AAV9 remaining in the supernatant (FIG. 3B, lane marked "SP load") highly amenable to cation-exchange chromatography. AAV9 quantitatively binds to SP resin (FIG. 3B, lane "SP FT"), and is eluted with higher pH (measured pH4.6) and sodium ion concentration (0.25 M NaCl) with very little contaminating proteins (FIG. 3B, lane "SP 50% B"). These low MW were effectively removed during the subsequent concentration/ultrafiltration step through 150 kDa cut-off TFF concentrator (FIG. 3B, lane "TFF"). There was little difference between the SP-purified/TFF-concentrated fraction and the rAAV9 sample purified by the "standard" protocol using an iodixanol gradient (FIG. 3B, lane "293 iodixanol"). The additional faint bands in the purified sample seen on the silver-stained gel were VP-derived peptides (FIG. 3C, right panel). These peptides appear to be the products of capsid protein auto-cleavage [ref. 19], therefore there was no evidence that AAV vectors purified by the current protocol incorporated higher ratios of the cleaved peptides compared to the "standard" iodixanol method. Electron microscopy examination of rAAV9 capsid purified by SP column chromatography (FIG. 3D) revealed a higher degree of purity and integrity of the sample as compared to the one purified by iodixanol gradient (FIG. 3E). The total yield in the peak SP 50% B fraction constituted 84% of the SP load (by dot blot assay), or 53% (by PCR assay), or 93% (by green cell assay (GCA)) (FIG. 3F). Thus, in several simple steps, rAAV9-GFP was purified to a highest degree of purity while retaining more than 90% yield in a TFF-concentrated final stock.

AAV2.

Figure 4D:
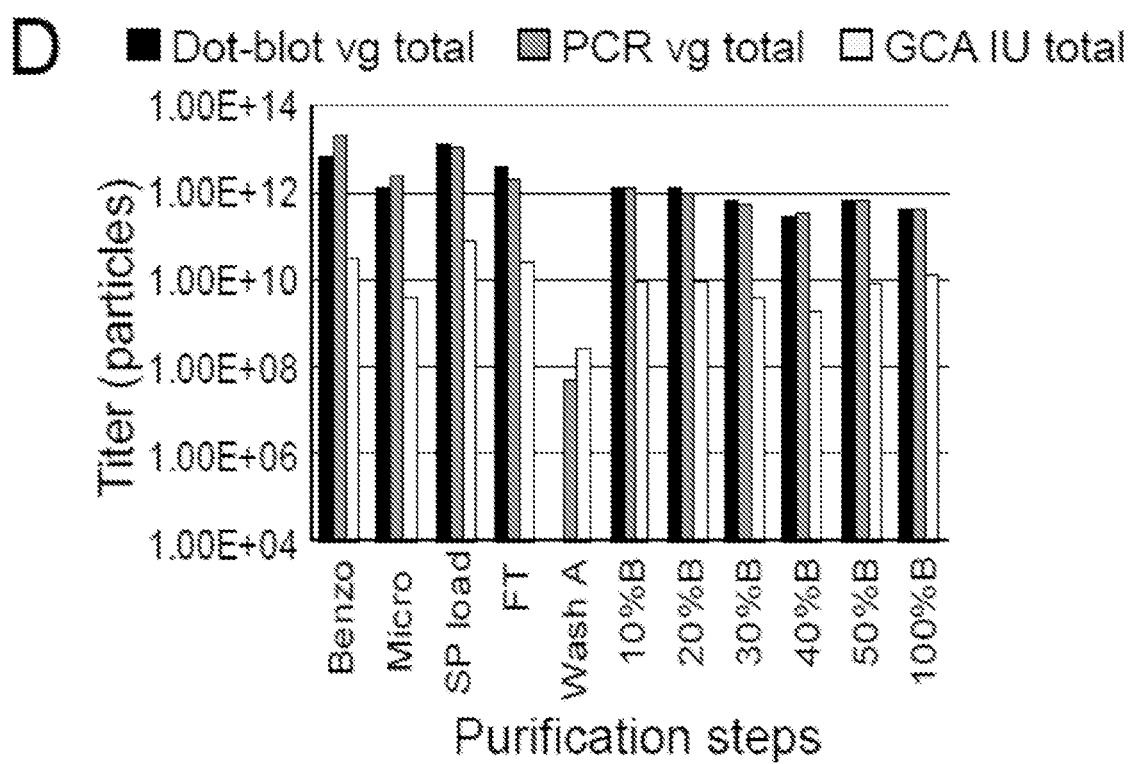

AAV2 is one of the most utilized and studied serotypes providing structural platform for rationally designed vectors and combinatorial capsid libraries. Using similar to AAV9 conditions, we attempted to purify AAV2-GFP produced in HEK 293 cells (FIG. 4A). AAV2 capsid proteins appeared to constitute one of the major protein components of the supernatant after the flocculation/centrifugation steps since VP3 was readily identifiable on a silver stained gel (FIG. 4B, lane "SP load"). However, a significant fraction of the virus was lost in the flow through (FIG. 4B, lane "SP FT"). Consistent with weak binding at this pH condition, the elution of AAV2 was initiated at lower Na$^+$ (50 mM-100 mM). The total yield in the peak SP 20% B fraction constituted 5.2% of the SP load (by dot blot assay), or 6.2% (by PCR assay), or 11.2% (by GCA) (FIG. 4D). The eluted and concentrated vector, however, was remarkably pure (FIG. 4B, lane "TFF"), with no detectable contaminating proteins identified at this sample load, with the exception of B1-immunoreactive peptides, the product of capsid auto-cleavage (FIG. 4C, lane "293 iodixanol").

AAV8.

Figure 5A:
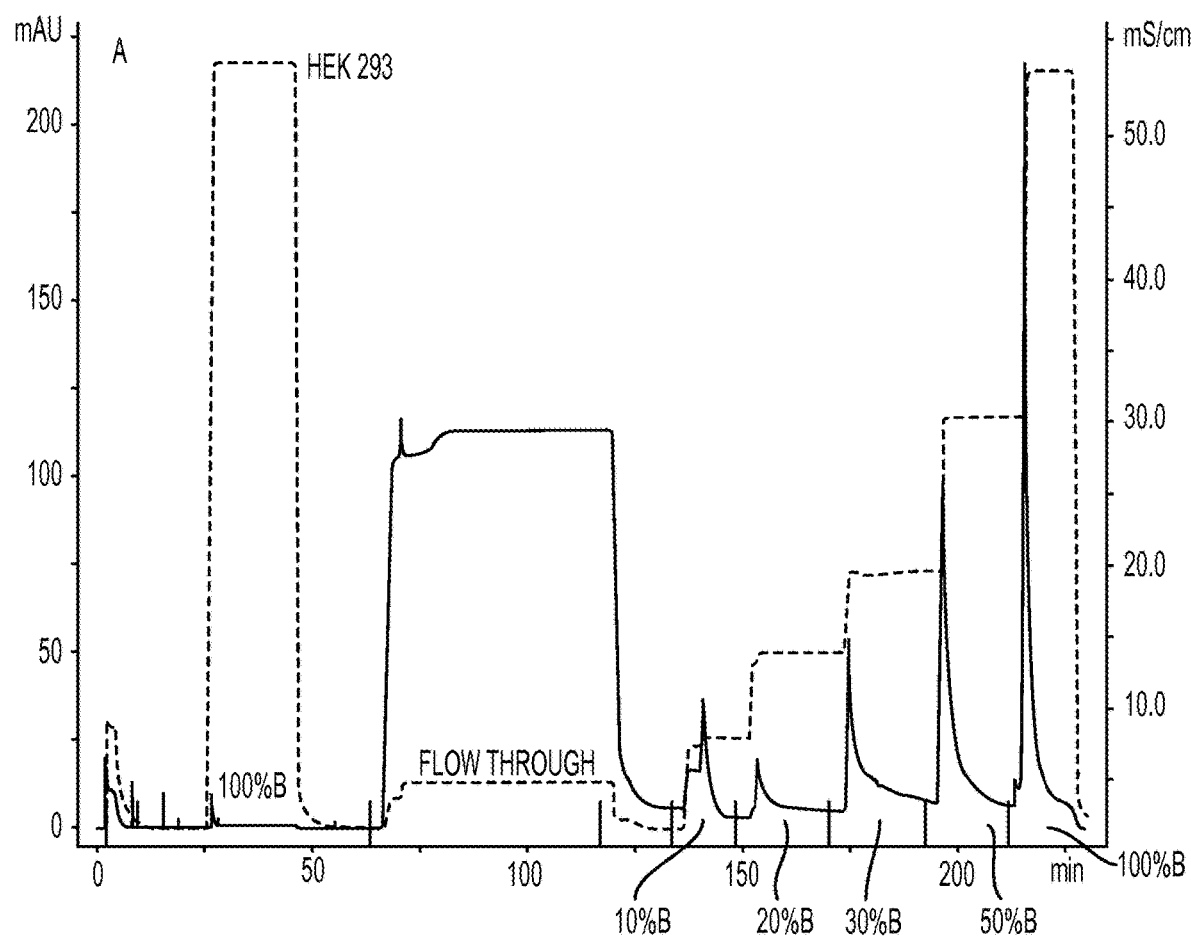
FIGS. 5A-F are a series of graphs and photographs showing an exemplary rAAV8 purification.
Figure 5B:
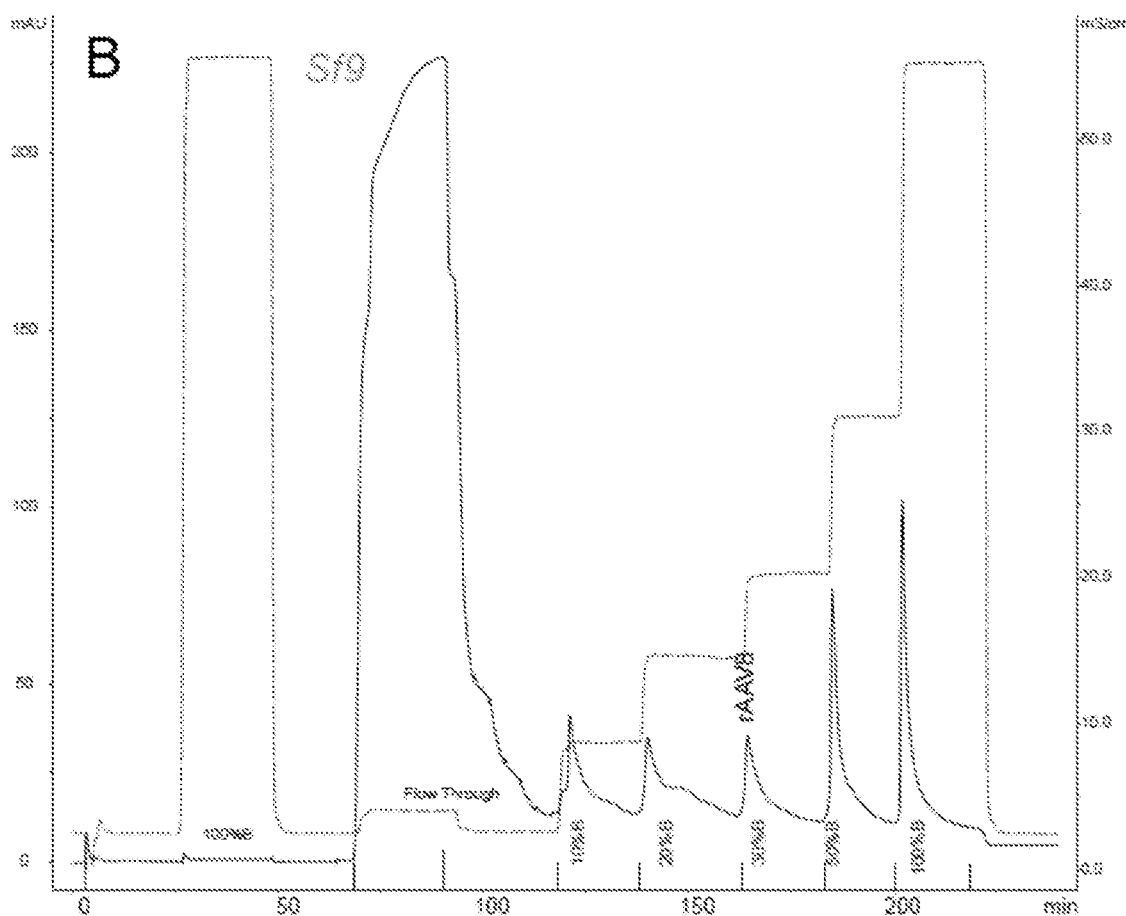
Figure 5C:
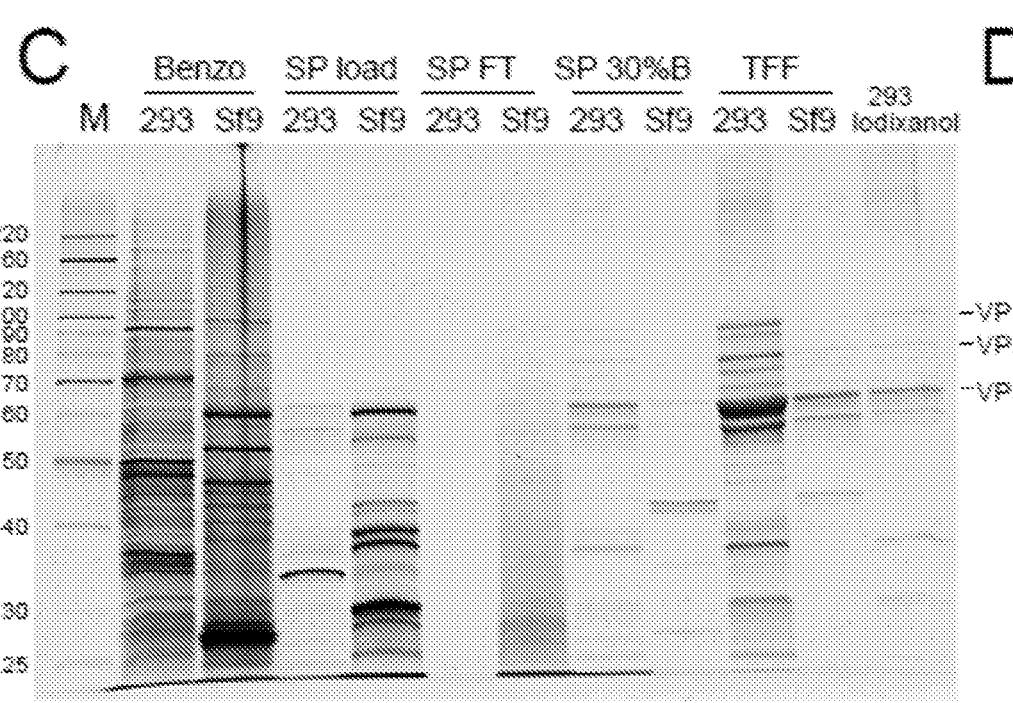
Figure 5D:
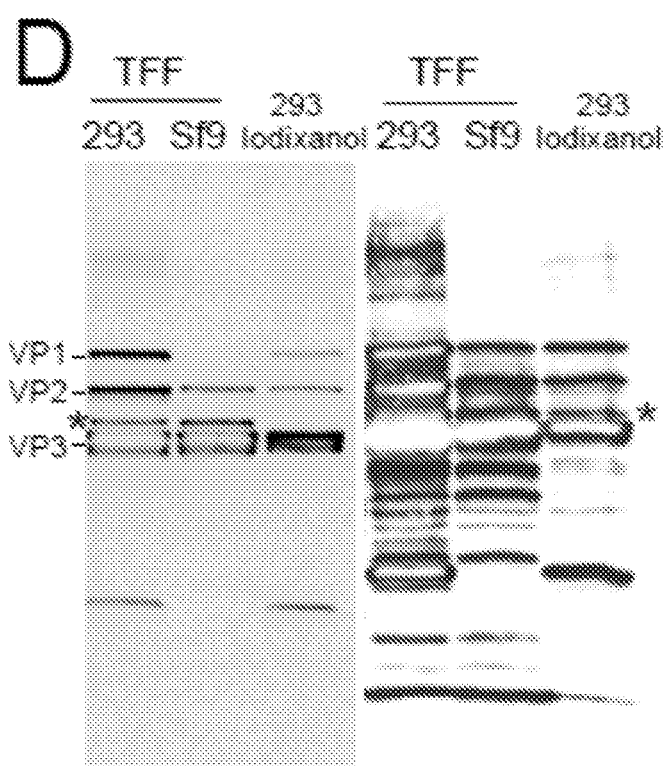
Figures 5E, 5F:
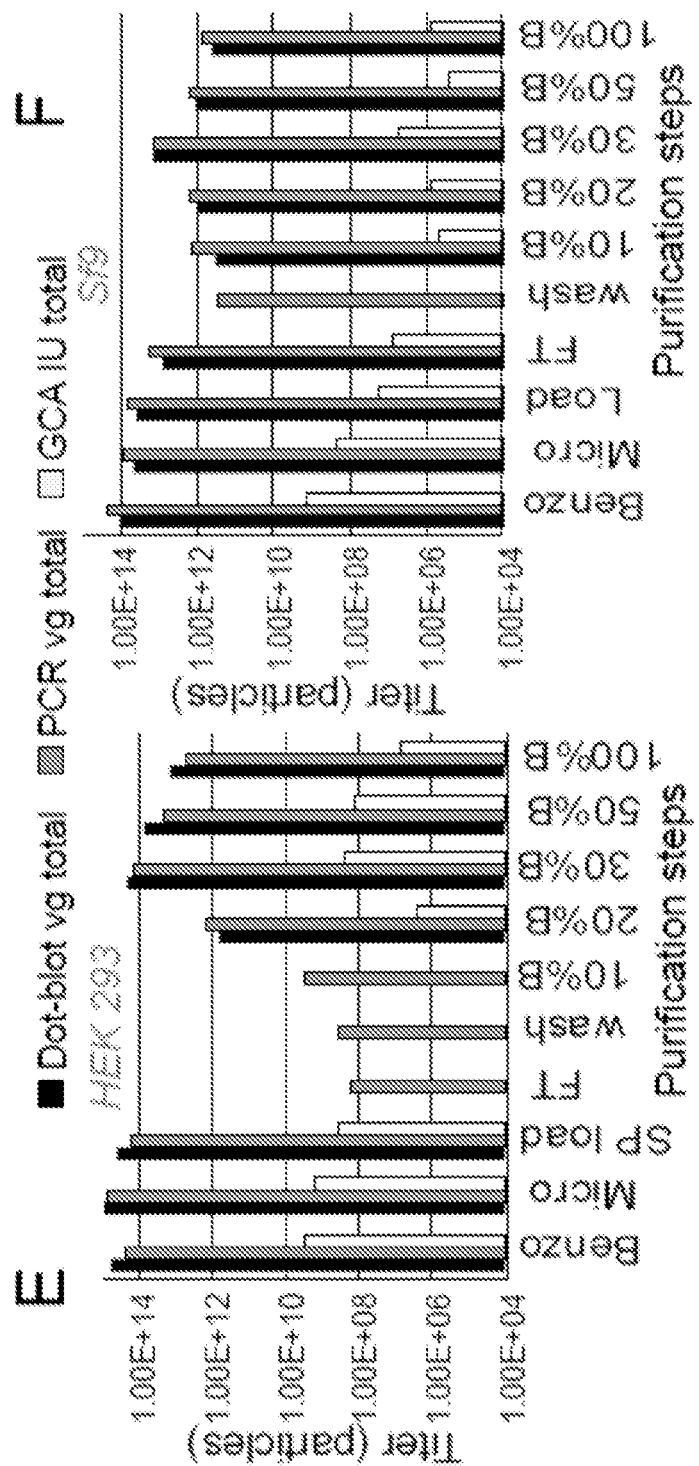

AAV8 serotype-based vectors are among the most efficient vehicles for transducing target tissues in vivo, and they are widely utilized both in the laboratory setting and in clinical trials. Moreover, several laboratories have designed insect cell-based systems to scale up production of rAAV8 vectors [refs. 20, 21]. To investigate whether this method could be extended further to purify AAV8 from mammalian, as well as from the insect cell milieu, a side-by-side purification was conducted using identical conditions for rAAV8 packaged in HEK 293 cells vs Sf9 cells (FIG. 5A, B). As expected, the respective crude lysates showed divergent protein patterns (FIG. 5C, lanes "Benzo, 293 and Sf9"). Even after flocculation/centrifugation, the SP loads were very much distinct for both samples, although already at this point, VP3 could be easily identified in both samples. The Sf9-derived rAAV8 vector had a lower VP1/VP2 capsid protein content (FIG. 5D), consistent with previous reports [refs. 20, 22]. This is a characteristic of the AAV8 produced in Baculovirus expression system and in no way is related to the purification protocol. An extra B1-immunoreactive minor band present in both 293- and Sf9-derived TFF samples (FIG. 5D, marked by the * asterisk) was also identified in the iodixanol sample, although only at 10-fold higher load. If this peptide is a product of capsid autocleavage, then perhaps it happens at a somewhat higher rate under the low pH conditions used in this protocol. There was no evidence, however, that these minor alterations affect the vector's infectivity. The total yield in the peak SP 30% B fraction constituted 56% of the SP load (by dot blot assay), or 22% (by PCR assay), or 62.8% (by GCA) for 293-derived rAAV8 (FIG. 5E), with comparable yields for Sf9-derived vector (FIG. 5F).

In some aspects, a purpose of the current project was to develop a simple and reproducible purification method applicable to many, if not all, AAV serotypes and variants. In addition, the method should be applicable to AAV vectors produced from either mammalian or Sf9 insect cell cultures, i.e. from very different cellular protein milieus. Previously, an in-depth study of methods for the recovery of rAAV from bulk cell lysates was conducted, establishing that no satisfactory method existed among those tested at the time [ref. 8]. In the current project, a less explored method of low pH-induced flocculation of colloidal suspensions in a crude cell lysate was used [ref. 23]. The relative stability of AAV under low pH conditions has been taken into consideration [refs. 18, 24], as well as reports that rAAVs can be purified under low pH conditions by AVB Sepharose HP affinity chromatography [refs. 16, 25]. Target flocculation pH was selected in the range of pH3-pH4 [ref. 23], and the sodium citrate buffer pH3.9 was found to be the most consistent in forming the flocculate without AAV virus loss. Moreover, sodium citrate buffer was selected for the subsequent chromatography step because of its working pH range of 3.0-6.2, $pK_A$=6.4 [ref. 26]. The analysis of the calculated isoelectric points (pI) mean values of capsids of all characterized AAV serotypes 1-12 showed their slightly acidic character (pI=6.3) [ref. 18]. This meant that at lower pH, the capsids will be protonated and thus capable of binding to a strong cation exchanger containing, for example, a bonded sulfonic acid group, such as sulfopropyl (SP). At the buffer pH values approaching the isoelectric target point (pI=6.3), capsids become zwitterionic (charge-neutral), which would enable their dissociation and elution from the resin. Thus, the flocculation and subsequent binding to SP resin could be carried at pH3.9, while elution from the resin could be conducted at higher pH approaching pH6.2. It was also anticipated that because of the relative uniformity of the capsids' pI across all characterized serotypes, the purification procedure would be applicable to many AAVs.

Prior to the method development it was determined whether exposing virus to low pH modified its structure, rendering it non-infectious. Consistent with previous observations [ref. 18], acidification of the virus for 2 h resulted in little if any reduction of the infectivity. Although longer incubations were somewhat unfavorable, the actual time of the purification (flocculation followed by column chromatography) is compatible with short low pH exposure times.

Described herein is a simplified purification protocol which, regardless of the upstream production method, yields exceptionally pure vector preparations. The protocol was tested using three serotypes (AAV2, AAV8, and AAV9) from three different clades (Clade B, E, and F, respectively) [ref. 27] thus validating its potential applicability to many AAV serotypes and mutants. The yield of the purified virus was significantly different for three serotypes tested ranging from to 11% (AAV2), to 63% (AAV8), to 93% (AAV9) suggesting that for each serotype, optimization of chromatography step may be needed. Shown herein is the protocol's utility in the context of rAAV vectors produced by triple transfection in mammalian HEK 293 cells and in insect Sf9 cells produced by infection with baculovirus, providing evidence of the protocol's potential usefulness in an industrial scale-up production environment. It is believed that this is one of the most inexpensive protocols utilizing simple off-the-shelf reagents such as sodium citrate and citric acid. Moreover, substituting SP Sepharose (bulk price —$1/ml) for AVB Sepharose HP ($50/ml) brings the AAV vector methodology within the reach of essentially any research laboratory. The protocol could be simplified even further by substituting microfluidization with sonication, or freeze/thawing of a cell pellet, or even hypotonic lysis in $H_2O$; and tangential flow filtration—with low-speed centrifugation/concentration through 150 kDa cut-off Apollo concentrator. Separating DNA-containing and empty rAAV particles without ultracentrifugation in buoyant density gradients remains a technical challenge. Curiously, the pI value for virions incorporating packaged DNA is different from those for empty capsids [ref. 12]. Perhaps modifying chromatography conditions and/or carriers as previously described [ref. 12] will allow rAAV9 (and other serotypes) preparations to be more enriched for particles incorporating DNA.

In summary, described herein is an affordable protocol for the purification of rAAV using off-the-shelf reagents and easy to follow steps. Because of its overall simplicity, the protocol could be used in a regular research laboratory, as well as further adapted for GMP-grade industrial scale production.

Material and Methods

Production of rAAV from HEK 293 Cells

Typically, rAAV was produced by $CaPO_4$-mediated transfection of plasmid DNA in 293 cells grown in CellStack® format (Corning, seeded area of 6360 cm$^2$ containing ~1×10$^9$ cells at the time of transfection, ~1.5×10$^9$ cells at harvest), as previously described [ref. 14]. Briefly HEK293 cells were seeded at approximately 30% confluence (~4.8E+8 cells) in a single 10 stack "CellStack" (6,360 cm$^2$ growth surface area) 24 hours prior to transfection. Following the 24 hour incubation the confluence of the CellStack increased to 50-60% confluence at the time of transfection. Transfection of the HEK293 cells was accomplished by calcium phosphate precipitation. The transfection consisted of preparing plasmid DNA that was suitable for uptake, copying and expression of some of the genes contained within the plasmids. Helper plasmids pXX6 & rep2cap9 were co-transfected with pTR-UF11 cloning plasmid. The transfection reagents were mixed appropriately and applied to the HEK293 cells in culture. The HEK293 cells were incubated at 37 C degrees, 5% CO2 for 3-5 days after which time either the media, the cells or both were harvested for purification of AAV.

Production of rAAV from Sf9 Producer Cell Lines rAAV was produced from Sf9-based producer stable cell lines upon infection with a single recombinant baculovirus encoding the rAAV expression cassette, as previously described [refs. 21, 28]. Typically, insect cells were grown in 1 L suspension (4×250 ml in 2 L Erlenmeyer flasks each) until their densities reached 2×10$^6$ cells/ml at which point recombinant Bac-rAAV-GFP was added at M.O.I. of 5. Cells were harvested 72 h later and rAAV was purified as described below.

Production of Clarified Crude Lysates

To maintain the reproducibility regardless of the scale of the process the volumes of each of the reagents used in this protocol were based on the approximate wet weight of the harvested cell pellet. An approximation of 1 g cell pellet wet weight being equal to 1 ml was used in lieu of actual weights and volumes that can be determined by direct measure or displacement. FIG. 1 shows an overview of the process: cell pellet was resuspended in an appropriate volume of 100 mM sodium citrate followed by the addition of magnesium and benzonase. Following the digestion an appropriate volume of 100 mM citric acid was added to acidify the slurry and to initiate the formation of a protein flocculate. After low-speed centrifugation, the supernatant was subjected to ion exchange chromatography.

A Citrate Buffer Table [ref. 26] was used to identify ratios of the buffer pair: 100 mM sodium citrate ($Na_3C_6H_5O_7$) and 100 mM citric acid ($C_6H_8O_7$) were mixed at the respective ratio of 16:34 (v/v) to derive a buffer of pH3.9. In practice, frozen cell pellets were resuspended in 100 mM sodium citrate pH8.05, 1.44 ml/g wet cell pellet weight, at approximately 1.9×10$^8$ cells/g wet cell weight. dd$H_2O$ was then added, 2.25 ml/g wet cell weight, followed by $MgCl_2$ to a final concentration of 1.6 mM. DNA contaminants were digested by incubation with Benzonase® (200 units/g wet cell weight) for 1 h at 37° C. Cells were disrupted by one-pass microfluidization (Microfluidics Model 110S Microfluidizer fitted with "Z" type interaction chamber to produce a colloidal suspension of particles of 100 μm or less) and 100 mM citric acid was added (3.06 ml/g wet cell weight), followed by addition of $H_2O$, 2.25 ml/g wet cell weight. Heavy flocculate, which immediately formed at this point, was precipitated by centrifugation at 4,450×g for 10 min at RT. Supernatant (pH~3.6) was collected and subjected to SP cation exchange chromatography.

SP Column Chromatography

HiPrep SP HP 16/10 (20 ml bed volume, GE Healthcare Life Sciences) was equilibrated with 5 column bed volumes (BV) of Buffer A: 25 mM sodium citrate buffer, target pH3.9 (mixed at the ratios as described above and diluted 4-fold), followed by 5 BV of Buffer B: 50 mM sodium citrate buffer, target pH6.2 (sodium citrate to citric acid ratio of 42.8:7.2, diluted 2-fold), containing 0.5 M NaCl, followed by 5 BV of Buffer A. The clarified supernatant was applied to the column at 5 ml/min, washed with Buffer A until the absorption at $A_{280}$ reached background levels, followed by wash with 5 BV of 90% Buffer A—10% Buffer B mixture (target pH4.65). AAV virus was eluted by the buffer mixture of 80% Buffer A—20% Buffer B (for AAV2, target pH4.96), or 70% Buffer A—30% Buffer B (for AAV8, target pH5.22), or 50% Buffer A—50% Buffer B (for AAV9, target pH5.57). Some samples were further purified using a tangential flow filtration system (TFF, "Mid-Gee" system, GE Healthcare Life Sciences, connected to a Watson Marlow 323 pump and a pressure monitor from Amersham).

rAAV Titering

Dot-blot assay, PCR assay, and green cell fluorescent assays (GCA) were described earlier [ref. 14, 29]. For the GCA, 2×10⁴ C12 cells [ref. 30] per well in 96-well plates were infected with serial dilutions of a rAAV-GFP vector and co-infected with Ad5 (M.O.I. of 5) to increase the sensitivity. Forty eight hours later, cells infected with rAAV-GFP were visually scored using a fluorescence microscope and the titer was calculated according to the dilution factor.

Dot-Blot Immunoassay rAAV9-GFP was diluted to 2 ng/µl in citrate-phosphate buffer at pH 7.4, 6.0, 5.5, or 4.0 containing 150 mM NaCl. Samples were incubated in a BioRad C1000 Touch Thermal Cycler at a temperature range of 4-100° C. for initial experiments to broadly determine capsid stability (data not shown) then a narrower temperature range of 70-80° C. for subsequent experiments to more accurately assess capsid stability, for 5 min, then cooled to 4° C. Twenty ng of a treated sample was immobilized onto a nitrocellulose membrane using a dot-blot apparatus (Bio-Rad). Blots were blocked in 5% milk in 0.05% Tween-PBS and probed for intact capsids, denatured capsids, or VP1u externalization using anti-AAV9 capsid monoclonal antibodies HL-2370 at 1:1000, B1 (American Research Products) at 1:3000, or A1 (American Research Products) at 1:20, respectively. Detection was carried out using HRP-linked anti-mouse monoclonal antibody at 1:5000 (GE Healthcare) and Immobilon chemiluminescent substrate (Millipore).

Electron Microscopy (EM)

rAAV9-GFP was diluted to 50 ng/µl in citrate-phosphate buffer at pH 7.4, 6.0, 5.5, or 4.0 containing 150 mM NaCl and heated to 73° C., 75° C., 77° C., 78° C., or 80° C. for 5 min then cooled to 4° C. using a BioRad C1000 Touch Thermal Cycler. Samples were adhered to glow-discharged carbon-coated copper grids (TED Pella) and stained with 2% uranyl acetate. Images were collected using a Tecnai G2 Spirit transmission electron microscope (FEI Co., Eindhoven, Netherlands).

REFERENCES

1. Mueller, C & Flotte, T R. (2008). Clinical gene therapy using recombinant adeno-associated virus vectors. Gene Ther 15: 858-863.
2. High, K A & Aubourg, P. (2011). rAAV human trial experience. Methods Mol Biol 807: 429-457.
3. High, K A. (2011). Gene therapy for haemophilia: a long and winding road. J Thromb Haemost 9 Suppl 1: 2-11.
4. Mingozzi, F & High, K A. (2011). Immune responses to AAV in clinical trials. Curr Gene Ther 11: 321-330.
5. Asokan, A, Schaffer, D V & Samulski, R J. (2012). The AAV vector toolkit: poised at the clinical crossroads. Mol Ther 20: 699-708.
6. Nathwani, A C, Tuddenham, E G, Rangarajan, S, Rosales, C, McIntosh, J, Linch, D C et al. (2011). Adenovirus-associated virus vector-mediated gene transfer in hemophilia B. N Engl J Med 365: 2357-2365.
7. Zhong, L, Li, B, Mah, C S, Govindasamy, L, Agbandje-McKenna, M, Cooper, M et al. (2008). Next generation of adeno-associated virus 2 vectors: point mutations in tyrosines lead to high-efficiency transduction at lower doses. Proc Natl Acad Sci USA 105: 7827-7832.
8. Zolotukhin, S, Byrne, B J, Mason, E, Zolotukhin, I, Potter, M, Chesnut, K et al. (1999). Recombinant adeno-associated virus purification using novel methods improves infectious titer and yield. Gene Ther 6: 973-985.
9. Clark, K R, Liu, X, McGrath, J P & Johnson, P R. (1999). Highly purified recombinant adeno-associated virus vectors are biologically active and free of detectable helper and wild-type viruses. Hum Gene Ther 10: 1031-1039.
10. Auricchio, A, O'Connor, E, Hildinger, M & Wilson, J M. (2001). A single-step affinity column for purification of serotype-5 based adeno-associated viral vectors. Mol Ther 4: 372-374.
11. Brument, N, Morenweiser, R, Blouin, V, Toublanc, E, Raimbaud, I, Cherel, Y et al. (2002). A versatile and scalable two-step ion-exchange chromatography process for the purification of recombinant adeno-associated virus serotypes-2 and -5. Mol Ther 6: 678-686.
12. Okada, T, Nonaka-Sarukawa, M, Uchibori, R, Kinoshita, K, Hayashita-Kinoh, H, Nitahara-Kasahara, Y et al. (2009). Scalable purification of adeno-associated virus serotype 1 (AAV1) and AAV8 vectors, using dual ion-exchange adsorptive membranes. Hum Gene Ther 20: 1013-1021.
13. Kaludov, N, Handelman, B & Chiorini, J A. (2002). Scalable purification of adeno-associated virus type 2, 4, or 5 using ion-exchange chromatography. Hum Gene Ther 13: 1235-1243.
14. Zolotukhin, S, Potter, M, Zolotukhin, I, Sakai, Y, Loiler, S, Fraites, T J, Jr. et al. (2002). Production and purification of serotype 1, 2, and 5 recombinant adeno-associated viral vectors. Methods 28: 158-167.
15. Davidoff, A M, Ng, C Y, Sleep, S, Gray, J, Azam, S, Zhao, Y et al. (2004). Purification of recombinant adeno-associated virus type 8 vectors by ion exchange chromatography generates clinical grade vector stock. J Virol Methods 121: 209-215.
16. Hellstrom, M, Ruitenberg, M J, Pollett, M A, Ehlert, E M, Twisk, J, Verhaagen, J et al. (2009). Cellular tropism and transduction properties of seven adeno-associated viral vector serotypes in adult retina after intravitreal injection. Gene Ther 16: 521-532.
17. Zhou, J, Yang, X, Wright, J F, High, K A, Couto, L & Qu, G. (2011). PEG-modulated column chromatography for purification of recombinant adeno-associated virus serotype 9. J Virol Methods 173: 99-107.
18. Venkatakrishnan, B, Yarbrough, J, Domsic, J, Bennett, A, Bothner, B, Kozyreva, O G et al. (2013). Structure and dynamics of Adeno-Associated Virus serotype 1 VP1-unique N-terminal domain and its role in capsid trafficking. J Virol 87: 4974-4984.
19. Salganik, M, Venkatakrishnan, B, Bennett, A, Lins, B, Yarbrough, J, Muzyczka, N et al. (2012). Evidence for pH-dependent protease activity in the adeno-associated virus capsid. J Virol 86: 11877-11885.
20. Kohlbrenner, E, Aslanidi, G, Nash, K, Shklyaev, S, Campbell-Thompson, M, Byrne, B J et al. (2005). Successful production of pseudotyped rAAV vectors using a modified baculovirus expression system. Mol Ther 12: 1217-1225.
21. Mietzsch, M, Grasse, S, Zurawski, C, Weger, S, Bennett, A, Agbandje-McKenna, M et al. (2014). OneBac: Platform for Scalable and High-Titer Production of Adeno-Associated Virus Serotype 1-12 Vectors for Gene Therapy. Hum Gene Ther.
22. Grimm, D, Streetz, K L, Jopling, C L, Storm, T A, Pandey, K, Davis, C R et al. (2006). Fatality in mice due to oversaturation of cellular microRNA/short hairpin RNA pathways. Nature 441: 537-541.
23. Gellan, E, Martin, G F & Cumming, R H. (1991). Flocculation of cell debris from ultrasonicated *Escherichia coli*. Biotechnol Bioeng 37: 697-702.
24. Nam, H J, Gurda, B L, McKenna, R, Potter, M, Byrne, B, Salganik, M et al. (2011). Structural studies of adeno-associated virus serotype 8 capsid transitions associated with endosomal trafficking. J Virol 85: 11791-11799.

25. Smith, R H, Levy, J R & Kotin, R M. (2009). A simplified baculovirus-AAV expression vector system coupled with one-step affinity purification yields high-titer rAAV stocks from insect cells. Mol Ther 17: 1888-1896.
26. Gomori, G (ed.) Preparation of buffers for use in enzyme studies, Vol. 1. (Academic Press, New York; 1955).
27. Gao, G, Vandenberghe, L H, Alvira, M R, Lu, Y, Calcedo, R, Zhou, X et al. (2004). Clades of Adeno-associated viruses are widely disseminated in human tissues. J Virol 78: 6381-6388.
28. Aslanidi, G, Lamb, K & Zolotukhin, S. (2009). An inducible system for highly efficient production of recombinant adeno-associated virus (rAAV) vectors in insect Sf9 cells. Proc Natl Acad Sci USA 106: 5059-5064.
29. Zeltner, N, Kohlbrenner, E, Clement, N, Weber, T & Linden, R M. (2010). Near-perfect infectivity of wild-type AAV as benchmark for infectivity of recombinant AAV vectors. Gene Ther 17: 872-879.
30. Clark, K R, Voulgaropoulou, F & Johnson, P R. (1996). A stable cell line carrying adenovirus-inducible rep and cap genes allows for infectivity titration of adeno-associated virus vectors. Gene Ther 3: 1124-1132.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of purifying recombinant adeno-associated virus (rAAV) particles from a cell culture comprising the rAAV particles, the method comprising:
   a) providing a crude cell lysate from the cell culture having a pH of between 6 and 9 and comprising the rAAV particles;
   b) reducing the pH of the crude cell lysate of a) to less than or equal to 5 to produce a flocculate and a supernatant comprising the rAAV particles;
   c) isolating the supernatant comprising the rAAV particles from the flocculate; and
   d) contacting the isolated supernatant of c) with a cation exchange chromatography, thereby purifying the rAAV particles.

2. The method of claim 1, wherein reducing the pH in b) comprises contacting the cell lysate comprising the rAAV particles with a triprotic acid.

3. The method of claim 2, wherein the triprotic acid is citric acid.

4. The method of claim 1, wherein the cell lysate of a) further comprises sodium citrate.

5. The method of claim 4, wherein the cell lysate further comprises an endonuclease.

6. The method of claim 4, wherein the cell lysate further comprises $Mg^{2+}$ and benzonase.

7. The method of claim 1, wherein in step c) the isolating the supernatant comprising the rAAV particles from the flocculate comprises centrifugation or filtration.

8. The method of claim 1, wherein the cell lysate of a) is a mammalian or an insect cell lysate.

9. The method of claim 1, wherein the cation exchange chromatography is sulfopropyl column chromatography.

10. The method of claim 1, wherein the method further comprises: e) at least one of further purifying and concentrating the purified rAAV particles of d) by at least one of tangential flow filtration and centrifugation, thereby producing the further purified, concentrated, or purified concentrated rAAV particles.

11. The method of claim 1, wherein the cell lysate in a) is produced by microfluidization, sonication, freeze/thawing, or hypotonic lysis of cells comprising the rAAV particles.

12. The method of claim 1, wherein in step b) the reducing the pH of the cell lysate comprising the rAAV particles is to between pH 3 and 5.

13. The method of claim 1, wherein the rAAV particles are rAAV3, rAAV8, rAAV9 or rAAV10 particles.

14. The method of claim 1, wherein the rAAV particles of (d) are added to a pharmaceutical composition.

15. The method of claim 14, wherein the pharmaceutical composition comprises a pharmaceutically acceptable carrier.

* * * * *